US009657303B2

(12) United States Patent
Davenport et al.

(10) Patent No.: US 9,657,303 B2
(45) Date of Patent: May 23, 2017

(54) DECREASING NITRITE CONTENT IN TOBACCO VIA EXPRESSION OF A NITRITE REDUCTASE

(71) Applicant: British American Tobacco (Investments) Limited, London (GB)

(72) Inventors: Susie Davenport, Cambridge (GB); Martin Maunders, Cambridge (GB)

(73) Assignee: British American Tobacco (Investments) Limited, London (GB)

( * ) Notice: Subject to any disclaimer, the term of this patent is extended or adjusted under 35 U.S.C. 154(b) by 0 days.

(21) Appl. No.: 14/601,186

(22) Filed: Jan. 20, 2015

(65) Prior Publication Data

US 2015/0203858 A1   Jul. 23, 2015

Related U.S. Application Data

(63) Continuation-in-part of application No. 12/673,385, filed as application No. PCT/GB2008/050707 on Aug. 14, 2008, now abandoned.

(30) Foreign Application Priority Data

Aug. 15, 2007 (GB) .................................. 0715916.3

(51) Int. Cl.
    *C12N 15/82* (2006.01)
    *C12N 5/14* (2006.01)
    *A01H 1/06* (2006.01)
    *A01H 1/04* (2006.01)
    *C12N 9/06* (2006.01)

(52) U.S. Cl.
    CPC ........... *C12N 15/8243* (2013.01); *A01H 1/04* (2013.01); *A01H 1/06* (2013.01); *C12N 5/14* (2013.01); *C12N 9/0044* (2013.01); *C12Y 107/02001* (2013.01)

(58) Field of Classification Search
    None
    See application file for complete search history.

(56) References Cited

U.S. PATENT DOCUMENTS

2006/0225751 A1* 10/2006 Koga et al. .......... A24B 15/245
                                                                131/290
2010/0205689 A1   8/2010 Hatzfeld

FOREIGN PATENT DOCUMENTS

WO      2006076423 A2   7/2006

OTHER PUBLICATIONS

Davenport et al ("Increased Nitrite Reductase Activity in Tobacco Reveals a Stay-Green Phenotype", poster presented during the International Symposium on Nitrogen Nutrition in Plants held at Lancaster University, UK from Jul. 27, 2007 to Jul. 31, 2007).*
Tanaka et al 1994 (DNA Sequence 5: p. 57-61).*
Holmberg et al 2002 (Plant Physiology 130: p. 303-311).*
Bendahmane, A., et al. (2000) "Agrobacterium transient expression system as a tool for the isolation of disease resistant genes . . . " The Plant Journal, 21(1), p. 73-81.
Benfey, P.N., Chua, N-H. (1989) "Regulated genes in transgenic plants." Science 244, p. 174-181.
Cataldo, D.A., et al. (1975) "Rapid calorimetric determination of nitrate in plant tissue by nitration of salicylic acid." Community Soil Science & Plant Analysis, 6(1), 71-80.
Cornejo, D.A., et al. (1993) "Activity of a maize ubiquitin promoter in transgenic rice." Plant Molecular Biology 23, 567-581.
Crawford, N.M. (1995) "Nitrate: nutrient and signal for plant growth," The Plant Cell 7, p. 859-868.
Crété, P., et al. (1997) "Nitrite reductase expresion is regulated at the post transcriptional level by the nitrogen source in . . . " The Plant Journal 11(4), p. 625-634.
Crété, P., Vaucheret, H. (1999) "Expression and sequence requirement of nitrite reductase co-suppression." Plant Molecular Biology, 41, p. 105-114.
Datta and Sharma (1999) "Temporal and spatial regulation of nitrate reductase and nitrite reductase in greening maize leaves." Plant Science 144(2), p. 77-83.
Davenport (2007) "Increased Nitrite Reductase Activity in Tobacco Reveals a Stay-Green Phenotype", Abstract of presentation, programme for the International Symposium on Nitrogen Nutrition in Plants held at Lancaster University, UK from Jul. 27, 2007 to Jul. 31, 2007.
Davenport et al., (2007) "Increased Nitrite Reductase Activity in Tobacco Reveals a Stay-Green Phenotype", poster presented during the International Symposium on Nitrogen Nutrition in Plants held at Lancaster University, UK from Jul. 27, 2007 to Jul. 31, 2007.
Devereux, J., et al. (1984) "A comprehensive set of sequence anlysis programs for the VAX." Nucleic Acids Res. 12, p. 387-395.
Djennane, Samia, et al. (2004) "Expression of a deregulated tobacco nitrate reductase gene in potato increases biomass . . . " PLANTA (Berlin) vol. 219, No. 5.
Dorbe, M.F., et al. (1998) "Deletion analysis of the tobacco Nii1 promoter in Arabidopsis thaliana." Plant Science 139, p. 71-82.
Edwards, K., et al. (1991) "A simple and rapid method for the preparation of plant genomic DNS for PCR analysis." Nucleic Acid Research 19(6) p. 1349.
Ellis, G., et al. (1998) "Nitrite nd Nitrate Analyses: A Clinical Biochemistry Perspective." Clinical Biochemistry 31(4), p. 195-220.

(Continued)

*Primary Examiner* — Matthew Keogh
(74) *Attorney, Agent, or Firm* — McKee, Voorhees & Sease, PLC

(57) ABSTRACT

The present invention relates in one aspect to a method for producing a transgenic plant, comprising introducing into an unmodified plant an exogenous gene encoding a nitrite reductase, wherein expression of the nitrite reductase encoded by the exogenous gene reduces nitrite content in the transgenic plant relative to the unmodified plant. Also provided are transgenic plants and plant cells comprising an exogenous gene encoding a nitrite reductase, as well as associated uses, chimaeric genes and plant transformation vectors.

11 Claims, 22 Drawing Sheets

(56) References Cited

OTHER PUBLICATIONS

Gatz, C. (1995) "Novel inducible/repressible gene expression systems." Methods in Cell Biology 50, p. 411-424.
German, M.A., et al. (2003) "A rapid method for the analysis of zgosity in transgenic plants," Plant Science 164, p. 183-187.
Glevaree, G., et al. (2004) "Respective roles of the glutamine synthetase/glutamate synthase cycle and glutamate dehydrogenase in ammonium and amino . . . " Plata 219, p. 286-297.
Greer, F.R., et al. (2005) "Infant Methemoglobinemia: The role of dietary nitrate in food and water: A clinical report," American Academy of Paediatrics 116(3), p. 784-786.
Han, Y., et al. (2004) "The effect of endogenous mRNA levels on co-suppression in tomato." FEBS Letters 563, p. 123-128.
Hansen, G., et al. (1994) "Constitutive expression of the virulence genes improves . . . ," Proceedings of the National Academy of Science, USA—Plant Biology 91, p. 7603-7607.
Hansen, G., et al. (1999) "Recent advances in the transformation of plants," Trends in Plant Science 4, p. 226-231.
Hare, P.D., et al. (1999) "Proline synthesis and degradation: a model system for elucidating stress-related signal . . . " Journal of Experimental Botany 50(333), p. 413-434.
Hesse, H., et al. (2004) "Molecular analysis and control of cysteine biosynthesis: integration of nitrogen and sulphur . . . " Journal of Experimental Botany 55(401), p. 1283-1292.
Hodges, M. (2002) "Enzyme redundancy and the importance of 2-oxoglutarate in plant ammonium assimilation," Journal of Experimental Botany 53(370), p. 905-916.
Hoekema, A., et al. (1983) "A binary plant vector strategy based on separation of vir and T-DNA region of the Agrobacterium tumefaciens Ti-plasmid," Nature 303, p. 179-180.
Holmberg et al., (2002) "Sterol C-24 Methyltransferase Type 1 Controls the Flux of Carbon into Sterol Biosynthesis in Tobacco Seed", Plant Physiology, 130:303-311.
Hull, R., et al. (1986) "The sequence of carnation etched ring virus DNA: comparison with cauliflower mosaic virus and retroviruses," EMBO Journal 5(2), p. 3083-3090.
Ioslovich, I., et al. (2002) "Acceptable nitrate concentration of greenhouse lettuce: Tow optimal control policies," Biosystems Engineering 83(2), p. 199-215.
Isaacson, C. (2005) "The change of the staple diet of black South Africans from sorghum to maize (corn) is the cause of the epidemic . . . " Medical Hypotheses 64(3), p. 658-660.
Kaiser, W.M., et al. (2001) "Post translational regulation of nitrate reductase mechanism, physiological relevance . . . " Journal of Experimental Botany 52(363), p. 1981-1989.
Kaiser, W.M., et al. (2002) "Modulation of nitrate reductase: some new insights, an unusual case and a potentially . . . " Journal of Experimental Botany 53(370), p. 875-882.
Kato, C., et al. (2004) "Differentail expression of the nitrite reductase gene family in tobacco as revealed by . . . " Journal of Experimental Botany 55(403), p. 1761-1763.
Klimyuk, V., et al. (1993) "Alkali treatment for rapid preparation of plant material for reliable PCR analysis," The Plant Journal 3(3), p. 493-494.
Kronenberger, J., et al. (1993) "Cloning and expression of distinct nitrite reductases in tobacco leaves and roots," Molecular and General Genetics 236, p. 203-208.
Kruse, J., et al. (2002) "Elevated pCO2 favours nitrate reduction in the roots of wild-type tobacco (Nicotiana tabacum . . . " Journal of Experimental Botany 53(379), p. 2351-2367.
Lea, P.J., et al. (1974) "Alternative route for nitrogen assimilation in higher plants," Nature 251, p. 614-616.
Lea, P.J., et al. (2003) "Glutamate synthase and the synthesis of glutamate in plants," Plant Physiology and Biochemistry 41, p. 555-564.
Lea, U.S., et al. (2004) "Mutation of the regulatory phosphorylation site of the tobacco nitrate reductase results in high nitrite excretion and . . . " Planta 219, p. 59-65.
Lea, U.S., et al. (2006) "Posttranslational Regulation of Nitrate Reductase Strongly Affects the Levels of Free Amino Acids and Nitrate . . . " Plant Physiology 140, p. 1085-1094.
Lee, S., et al. (2006) "The reaction of flavanols with nitrous acid protects against N-nitrosamine formation and leads to . . . " Free Radical Biology and Medicine 40, p. 323-334.
Lillo, C., et al. (2003) "Mutation of the regulatory phosphorylation site of tobacco nitrate reductase results in constitutive activation . . . " The Plant Journal 35, p. 566-573.
Lillo, C., et al. (2004) "Mechanisms and importance of post-translational regulation of nitrate reductase," Journal of Experimental Botnay 55(401), p. 1275-1282.
Martin, A., et al. (2005) "Nitrogen management and senescence in two maize hybrids difefreing in the persistence of leaf greenness . . . " New Phytologist 167, p. 483-492.
Masclaux, C., et al. (2000) "Characterization of the sink-source transition in tobacco (Nicotiana tabacum L.) shoots in relation to nitrogen . . . " Planta 211, p. 510-518.
Matt, P., et al. (2001) "The immediate cause of the diurnal changes of nitrogen metabolism in leaves of nitrate replete . . . " The Plant, Cell and Environment 24, p. 177-190.
Miflin, B., et al. (2002) "The role of glutamine synthetase and glutamate dehydrogenase in nitrogen assimilation . . . " Journal of Experimental Botany 53(370), p. 979-987.
Mohr, H., et al. (1994) Plant Physiology. Springer. p. 181-184.
Morikawa, H., et al. (2004) "Formation of unidentified nitrogen in plants: an implication for a novel nitrogen metabolism," Planta 219, p. 14-22.
Morot-Gaudry-Talarmain, Y., et al. (2002) "Nitrite accumulation and nitric oxide emission in relation to cellular signalling in nitrie reductase . . . " Planta 215, p. 708-715.
Needleman, S.B., et al. (1970) "A general method applicable to the search for similarities in the amino acid sequence of . . . " Journal of Molecular Biology 48, p. 443-453.
Odell, J.T., et al. (1985) "Identification of DNA sequences required for activity of the cauliflower mosaic virus 35S promoter," Nature 313, p. 810-812.
Ozawa, K., et al. (2005) "Positional cloning of the nitrite reductase gene associated with good growth and regeneration ability of calli . . . " Plant Science 170, p. 384-393.
Paine, J., et al. (2005) "Improving the nutritional value of golden rice through increased pro-vitamin A content," Nature Biotechnology 23, p. 482-487.
Palauqui et al., (1996) "Frequencies, Timing, and Spatial Patterns of Co-Suppression of Nitrate Reductase and Nitrite Reductase in Transgenic Tobacco Plants", Plant Physiol., 112:1447-1456.
PCT/GB2008/050707, International Preliminary Report on Patentability, dated Feb. 15, 2010.
PCT/GB2008/050707, International Search Report and Written Opinion, dated Nov. 27, 2008.
PCT/GB2008/050707, Written Opinion of the International Searching Authority, dated Feb. 15, 2010.
Rockel, P., et al. (2002) "Regulation of nitric oxide (NO) production by plant nitrate reductase in vivo and in vitro," Journal of Experimental Botany 53(366), p. 103-110.
Rothstein, S.J., et al. (1998) "Nitrate inducibility of gene expression using the ntirate reductase gene . . . " Inducible Gene Expression in Plants CABI Publishing, p. 83-97.
Solomonson, L. P., et al. (1990) "Assimilatory nitrate reductase: functional properties . . . " Annual Review of Plant Physiology and Plant Molecular Biology 41, p. 225-253.
Staaf, M., et al. (2005) "Formation of tobacco-specific nitrosamines (TSNA) during air-curing: Condition and control." Contributions to Tobacco Research 21(6), p. 321-330.
Stitt, M., et al. (1999) "Lateral root frequency decreases when nitrate accumulates in tobacco transformants with low nitrate reductase . . . " Plant and Soil 215, p. 143-153.
Stohr, C. (1999) "Relationship of ntirate supply with growth rate, plasma membrane-bound and cytosolic nitrate reductase . . . " Plant, Cell and Environment 22, p. 169-177.
Stohr, C., et al. (2001) "Diurnal changes in nitrogen assimilation of tobacco roots," Journal of Experimental Botany 52(359), p. 1283-1289.

(56) References Cited

OTHER PUBLICATIONS

Swamy, U., et al. (2005) "Structure of spinach nitrite reductase: Implications for multi-electron reactions by the iron-sulfur:siroheme . . . " Biochemistry 44, p. 16054-16063.

Takahashi, Misa, et al., (2001) "Nitrite reductase gene enrichment improves assimilation of NO2 in Arabidopsis," Plant Physiology (Rockville), vol. 126, No. 2.

Tanaka et al., (1994) "Nucleotide sequence of a gene for nitrite reductase from Arabidopsis thaliana", DNA Sequence—The Journal of Sequencing and Mapping, vol. 5, pp. 57-61.

Tischner, T. (2000) "Nitrate uptake review in higher and lower plants," Plant, Cell and Environment 23, p. 1005-1024.

Tobin, A.K., et al. (2005) "Nitrogen and carbon metabolism in plastids: Evolution, integration, and coordination . . . " Advances in Botanical Research 42, p. 114-165.

Turano, F.J., et al. (1996) "Purification of mitochondrial glutamate dehydrogenase from dark-grown soybean seedlings," Plant Phsiology 112, p. 1357-1364.

Van Engelen, F.A., et al. (1995) "pBINPLUS: An improved plant transformation vector based on pBIN19," Transgenic Research 4, p. 288-290.

Vaucheret, H., et al. (1995) "Molecular and genetic analysis of nitrite reductase co-suppression in transgenic tobacco plants," Molecular and General Genetics 248, p. 311-317.

Vaucheret, H., et al. (1998) "Transgene-induced gene silencing in plants," The Plant Journal 16(6), p. 651-659.

Vaucheret, H., et al., (1992) "Inhibition of tobacco nitrite reductase activity by expression of antisense RNA," The Plant Journal: For Cell and Molecular Biology 2 (4) Jul. 1992.

Vaucheret, Nerve, et al., (1997) "Nitrate reductase and nitrite reductase as targets to study gene silencing phenomena in transgenic plants," Euphytica, vol. 93, No. 2.

Wang, R., et al. (2003) "Microarray analysis of the nitrate response in Arabidopsis roots and shoots reveals over 1000 rapidly responding . . . " Plant Physiology 132, p. 556-567.

Warner, S.A., et al. (1993) "isolation of an asparagus intracellular PR gene (AoPR1) wound-responsive promoter by the inverse polymerase . . . " Plant J. 3, p. 191-201.

Warning, H.O., et al. (2000) "Functional analysis of a Nitrite Reductase promoter from birch in transgenic tobacco," Plant Science 1551, p. 41-151.

Wendehenne, D., et al. (2004) "Nitric oxide: a new player in plant signalling and defence responses," Current Opinion in Plant Biology 7, p. 449-455.

Weng, H., et al. (2004) "Estiamting number of transgene copes in transgenic rapeseed by real-time PCR assay with HMG I/Y . . . " Plant Molecular Biology Reporter 22, p. 289-300.

Zhang, W., et al. (1991) "Analysis of rice Act1 5' region activity in transgenic rice plants," Plant Cell 3, p. 1155-1165.

Angenon et al. Antibiotic resistance markers for plant transformation. Plant Molecular Biology Manual C1. 1994. p. 125-137. Kluwer Academic Publishers. Belgium.

Ferrario-Mery et al. Overexpression of Nitrate Reductase in Tobacco Delays Drought-Induced Decreases in Nitrate Reductase Activity and mRNA. Plant Physiology. 1998. 117(1):293-302.

NCBI Reference Sequence: NP 179164, "Nitrite Reductase 1", 3 pages, Mar. 20, 2017.

Patent CN1842591, Monsanto Technology LLC, "Method for Elevation of Oil Levels in Plants", 27 pages, Oct. 4, 2006.

* cited by examiner

Figure 1
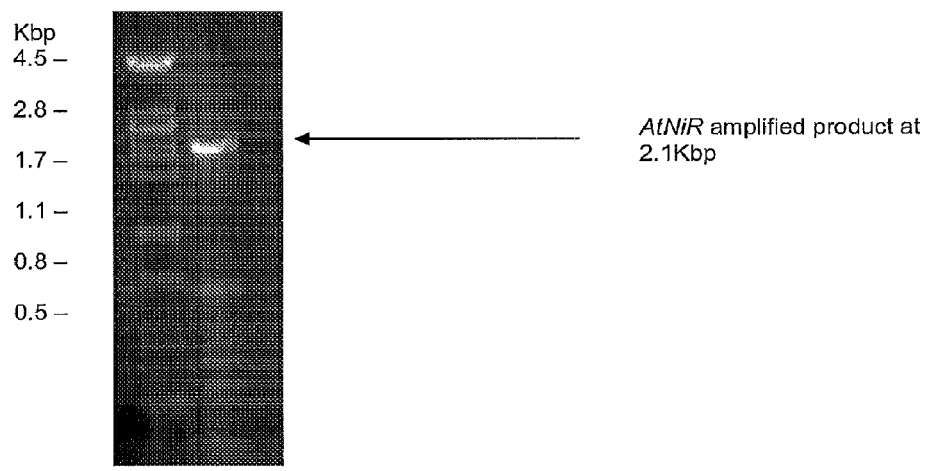
AtNiR amplified product at 2.1Kbp
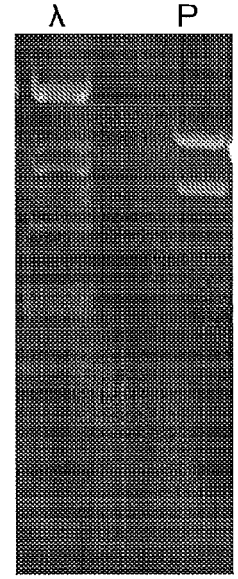
Figure 2 a)

SEQ ID NO:1

| | | | | | |
|---|---|---|---|---|---|
| atgacttctt | tctctctcac | tttcacatct | cctctcctcc | cttcctcctc | caccaaaccc | 60 |
| aaaagatccg | tccttgtcgc | cgccgctcag | accacagctc | cggccgaatc | caccgcctct | 120 |
| gttgacgcag | atcgtctcga | gccaagagtt | gagttgaaag | atggtttttt | tattctcaag | 180 |
| gagaagtttc | gaaaagggat | caatcctcag | gagaaggtta | agatcgagag | agagcccatg | 240 |
| aagttgttta | tggagaatgg | tattgaagag | cttgctaaga | aatctatgga | agagcttgat | 300 |
| agtgaaaagt | cttctaaaga | tgatattgat | gttagactca | agtggcttgg | tctctttcac | 360 |
| cgtagaaagc | atcagtatgg | gaagtttatg | atgaggttga | agttaccaaa | tggtgtgact | 420 |
| acaagtgcac | agactcggta | tttagcgagt | gtgattagga | agtatggtga | agatgggtgt | 480 |
| gctgatgtga | ctactagaca | gaattggcag | atccgtggtg | ttgtgttgcc | tgatgtgcct | 540 |
| gagatcttga | aaggtcttgc | ttctgttggt | taacgagtc | ttcaaagtgg | tatggataac | 600 |
| gtgaggaacc | cggttgggaa | tcctatagct | gggattgatc | cggaggagat | tgttgacacg | 660 |
| aggccttaca | cgaatctcct | ttcgcagttt | atcaccgcta | attcacaagg | aaacccgat | 720 |
| ttcaccaact | tgccaagaaa | gtggaatgtg | tgtgtggtgg | ggactcatga | tctctatgag | 780 |
| catccacata | tcaatgattt | ggcctacatg | cctgctaata | aagatggacg | gtttggattc | 840 |
| aatttgcttg | tgggaggatt | ctttagtccc | aaaagatgtg | aagaagcgat | tcctcttgat | 900 |
| gcttgggtcc | ctgctgatga | cgttcttcca | ctctgcaaag | ctgttctaga | ggcttacaga | 960 |
| gatcttggaa | ctcgaggaaa | ccgacagaag | acaagaatga | tgtggcttat | cgacgaactt | 1020 |
| ggtgttgaag | gatttagaac | tgaggtagaa | aagagaatgc | caaatgggaa | actcgagaga | 1080 |
| ggatcttcag | aggatcttgt | gaacaaacag | tgggagagga | gagactattt | cggagtcaac | 1140 |
| cctcagaaac | aagaaggtct | tagcttcgtg | gggcttcacg | ttccggttgg | taggctacaa | 1200 |
| gctgatgaca | tggatgagct | tgctcggtta | gctgatacct | acgggtcagg | tgagctaaga | 1260 |
| ctcacagtag | agcaaaacat | catcatccca | aatgtagaaa | cctcgaaaac | cgaagctttg | 1320 |
| cttcaagagc | cgtttctcaa | gaaccgtttc | tcccctgaac | catctatcct | aatgaaaggc | 1380 |
| ttagttgctt | gtaccggtag | ccagttctgc | ggacaagcga | taatcgagac | taagctaaga | 1440 |
| gctttaaaag | tgacagaaga | agtagagaga | cttgtatctg | tgccaagacc | gataaggatg | 1500 |
| cattggacag | gatgtcccaa | cacttgcgga | caagtccaag | tagcagatat | cggattcatg | 1560 |
| ggatgcttaa | cacgaggcga | ggaaggaaag | ccagtcgagg | gtgctgacgt | gtacgtcggg | 1620 |
| ggacgaaatag | gaagtgactc | gcatatcgga | gagatctata | agaaaggtgt | tcgtgtcacg | 1680 |
| gagttggttc | cattggtggc | tgagattctg | atcaaagaat | ttggtgctgt | gcctagagaa | 1740 |
| agagaagaga | atgaagattg | a | | | | 1761 |

SEQ ID NO:3

```
  1 MTSFSLTFTS PLLPSSSTKP KRSVLVAAAQ TTAPAESTAS VDADRLEPRV ELKDGFFILK
 61 EKFRKGINPQ EKVKIEREPM KLFMENGIEE LAKKSMEELD SEKSSKDDID VRLKWLGLFH
121 RRKHQYGKFM MRLKLPNGVT TSAQTRYLAS VIRKYGEDGC ADVTTRQNWQ IRGVVLPDVP
181 EILKGLASVG LTSLQSGMDN VRNPVGNPIA GIDPEEIVDT RPYTNLLSQF ITANSQGNPD
241 FTNLPRKWNV CVVGTHDLYE HPHINDLAYM PANKDGRFGF NLLVGGFFSP KRCEEAIPLD
301 AWVPADDVLP LCKAVLEAYR DLGTRGNRQK TRMMWLIDEL GVEGFRTEVE KRMPNGKLER
361 GSSEDLVNKQ WERRDYFGVN PQKQEGLSFV GLHVPVGRLQ ADDMDELARL ADTYGSGELR
421 LTVEQNIIIP NVETSKTEAL LQEPFLKNRF SPEPSILMKG LVACTGSQFC GQAIIETKLR
481 ALKVTEEVER LVSVPRPIRM HWTGCPNTCG QVQVADIGFM GCLTRGEEGK PVEGADVYVG
541 GRIGSDSHIG EIYKKGVRVT ELVPLVAEIL IKEFGAVPRE REENED
```

Figure 18

SEQ ID NO:2, 1-3720

```
   1 tctagaataa cgctaaagaa cacctatggc tctgataaca tattattaat atttacattt
  61 attttattta aagtagtcca ttcataattg cacacgacta aatgctacac aacttgtctt
 121 agttgtttaa tcaagatatt tttaccttat gatattttgt gaaaaatgat acctataaaa
 181 tccctaatga gcacatcaac ctttttacc ttattatatt ttgtgaaaaa tgatatctat
 241 aaaatcccta atgaccacat caaccttgaa tcttctctaa taaaccttt ttccaaacac
 301 gcactaaacc aaaaattaac atctcaagag gaaaccattt aaaaaaaaaa cagagttaga
 361 ttaagatcaa caaatatagt tgaaaagaac atatgttaag caacattacc ataaattcat
 421 aattagtagt gattaaaact taagaatact aaagtatgaa tatgaaaatt gttgtatttt
 481 tttgtagtat gtaatatgcg gaaacttgga tgttatccta ttcattgaaa ttcatatatg
 541 tatgtagtta tcattttta aatatattaa aaaattaaaa agtaataata ctataaacat
 601 tcaaattatg aaataaaat ctcatactaa tcactgctaa ttttttttcc aatgtttctc
 661 tttagtattt ctctttagta tgggagtgac aaacttaata tgaaatctat ctccctacat
 721 gcaaaaatcg aatctcttt attattaatg aagtgtatgg tcggtgtcaa taactaatat
 781 gtcatatttt ttacagactg ttcagatatg ataaaaatag tttttttcca accaaatggt
 841 tggtcttctg agtgtatttg aaaacgacat tgaagaatta atatatttt ttttaatttt
 901 agtttttat agtacaaata ttaaaacaaa caatcctacc atatcataac atttgtaaat
 961 aacattttaa gttttgtttt gagtttaat taatttcta tgacaaaaaa atgaagtcaa
1021 tagactaagt gaatcatata gtataaataa acacaattta aatagtttca aataaattta
1081 gaaagaataa aacaaataga aatcagaagg tgtctgtttc ctcctcgcaa catacgatca
1141 aagagaaaca acttgaccct ttacattgct caagagctca tctcttccct ctacaaaaat
1201 ggccgcacgt ctccaacctc ctcccaactg cttcttccgc catcatcatg acttctttct
1261 ctctcacttt cacatctcct ctcctcctt cctcctccac caaacccaaa agatccgtcc
1321 ttgtcgccgc cgctcagacc acagctccgg ccgaatccac cgcctctgtt gacgcagatc
1381 gtctcgagcc aagagttgag ttgaaagatg gtttttttat tctcaaggag aagtttcgaa
1441 aagggatcaa tcctcaggag aaggttaaga tcgagagaga gcccatgaag ttgtttatgg
1501 agaatggtat tgaagagctt gctaagaaat ctatggaaga gcttgatagt gaaaagtctt
1561 ctaaagatga tattgatgtt agactcaagt ggcttggtct ctttcaccgt agaaagcatc
1621 agtgtatgtt cctcctctct atcctcttcc attgacttgt gattgaactg tgtaaaggtt
1681 tcgtctttag tcttatgtgt gcttcttca atgacttgtg attaaattgg tgaccagatt
1741 gtgtaaaggt ttagtcttta ctctttatct ttagtacatt ttgatttatg agtgcttgtt
1801 gttgattttg ttgttgtaga tgggaagttt atgatgaggt tgaagttacc aaatggtgtg
1861 actacaagtg cacagactcg gtatttagcg agtgtgatta ggaagtatgg tgaagatggg
1921 tgtgctgatg tgactactag acagaattgg cagatccgtg gtgttgtgtt gcctgatgtg
1981 cctgagatct tgaaaggtct tgcttctgtt ggtttaacga gtcttcaaag tggtatggat
2041 aacgtgagga acccggttgg gaatcctata gctgggattg atccggagga gattgttgac
2101 acgacgcctt acacgaatct cctttcgcag tttatcaccg ctaattcaca aggaaacccc
2161 gatttcacca acttgtgagt tctctttta gattgatgtt gtgtgttggt gagtgaatgg
2221 ttatgctaag atgggttttt gtttgtttgt tgtaggccaa gaaagtggaa tgtgtgtgtg
2281 gtggggactc atgatctcta tgagcatcca catatcaatg atttggccta catgcctgct
2341 aataaagatg gacggttgg attcaatttg cttgtgggag gattctttag tcccaaaaga
2401 tgtgaagaag cgattcctct tgatgcttgg gtccctgctg atgacgttct tccactctgc
2461 aaagctgttc tagaggctta cagagatctt ggaactcgag gaaaccgaca gaagacaaga
2521 atgatgtgc ttatcgacga acttgtaagt acatgcttct tgcaatctta aattcggtat
2581 tgaagttctt ggttgttgat ttgtctgcat gaaatgtata gggtgttgaa ggatttagaa
2641 ctgaggtaga gaagagaatg ccaaatggga aactcgagag aggatcttca gaggatcttg
2701 tgaacaaaca gtgggagagg agagactatt tcggagtcaa ccctcagaaa caagaaggtc
2761 ttagcttcgt ggggcttcac gttccggttg gtaggctaca agctgatgac atggatgagc
2821 ttgctcggtt agctgatacc tacgggtcag gtgagctaag actcacagta gagcaaaaca
2881 tcatcatccc aaatgtagaa acctcgaaaa ccgaagcttt gcttcaagag ccgtttctca
2941 agaaccgttt ctcccctgaa ccatctatcc taatgaaagg cttagttgct tgtaccggta
3001 gccagttctg cggacaagcg ataatcgaga ctaagctaag agctttaaaa gtgacagaag
3061 aagtagagag acttgtatct gtgccaagac cgataaggat gcattggaca ggatgtccca
3121 acacttgcgg acaagtccaa gtagcagata tcggattcat gggatgctta acacgaggcg
3181 aggaaggaaa gccagtcgag ggtgctgacg tgtacgtcgg gggacgaata ggaagtgact
3241 cgcatatcgg agagatctat aagaaaggtg ttcgtgtcac ggagttggtt ccattggtgg
3301 ctgagattct gatcaaagaa tttggtgctg tgcctagaga aagagaagag aatgaagatt
3361 gattcaaaag ctattggatt cttaataagt caagagacct atgaatggtt ctctctctgg
3421 tttcagactt tgatacttga tacttgtatt tgtattgtgc ccataatttt gggttttgta
3481 gctctctcct ttgttgtaac ctgtaactt gtccttggtt gttttgtaat atcttgtttt
3541 ttagtaatag tagtatatg tgatttttc tcatatattg tcttgatttc tctgtgatat
3601 ttataagaaa taaacatttg tttctttta cctccaatat ttttgttttt gatatatcaa
3661 aagttaaggg aatagattt aattaataaa atatattgat aatattctta aaagattatt
```

Figure 19

SEQ ID NO:2, 3721-4380

```
3721 aataaattaa attgttttt tttaacgtc aatttcatta atttttaaga aagagtacat
3781 ggtaaataaa gcccaacaac acaattataa agtccaacta caaacccaat agaaagatta
3841 caacttgaga ttaaactagg tttagaaggg acacgtgttt aattatctgt tcttgcgcat
3901 gttggatgag aaaagatgcc gatatgactc atcaccgcca tcttgagttg aaccgtcgat
3961 cgaaattacc tagtccgtcg ttgaaatttg aaccatcata attattaaac tctggaacac
4021 gcgacatagc aagagggcag atcagttgca aaacacactc tcctgaactg ttctacgccg
4081 gccaccaaag ctccactcaa cacaattcac gatcttaaag aggcaccttc atcgttacca
4141 gattatggtg ccaacatggg aatgaaggct ttattctttt cttactcaga attgagcaac
4201 gaatggtcta caagattctg aattagacac tcagcttcta agatttaaga tatgcaaaag
4261 gtggatcaaa actatacaaa ttaaaaaaaa aagccataaa ggctaacaga agctcgcact
4321 taggcgagaa aacaaaaacc ggacaaagcc aaagacaaaa aatccggagg taaaaagaaa
```

Figure 20

SEQ ID NO:18

```
   1 gaattcggct cgagcccacc tcacccacc ttacgactac aaaaatgatc ttatttcgcc
  61 attttaacca tgaccgccac gatcatcacc accctcaata atcaagaatc aactaaattc
 121 ctcaattcca aatttggcga aatggcatct ttttctgtta aattttcagc aacttcttcg
 181 ctgacaagtt ctaagagatt ttccaagctt catgccactc caccgcagac agtggcagta
 241 cctccatctg gggcagtgga ggtagctgca gagagactag agcctagact ggaggaaaga
 301 gatgggtatt gggtacttaa ggaaaagttc agaaaaggca taaatcctgc tgaaaaggcc
 361 aagattgaaa aggaacctat gaaattgttc actgaaaatg gtattgaaga tattgctaag
 421 atctcacttg aagagatcga aaaatctaag cttgctaagg atgatattga tgttaggctc
 481 aagtggcttg gcctcttcca taggagaaag catcaatatg gacgattcat gatgcgactg
 541 aagcttccaa atgggataac gacgagtgcc caaactcgat atttagcaag tgtgattagg
 601 aaatatggga aagatgggat tgcagatgtg actacaaggc aaaattggca gattcgtggg
 661 gttgtgctac ctgatgtgcc tgagattcta aagggactgg atgaagttgg cttgaccagt
 721 ctgcaaagtg gcatggacaa tgttagaaat cccgtgggga accctctgcg ggggattgat
 781 ccacaagaaa ttgtggacac aaggccttac gctaatttgc tatccaattt gctatcccaa
 841 tatgtcactg ccaatttttcg tggcaatctg tccgtgcata acttgccaag gaagtggaat
 901 gtatgtgtaa tagggtcaca cgatctttat gagcatcccc atatcaatga tcttgcctat
 961 atgcctgcaa cgaaagatgg acgatttgga ttcaacctgc ttgtgggtgg attcttcagt
1021 ccgaagcgat gtgcagaggc aattcctctt gatgcatggg ttccagctga tgatgtagtc
1081 cctgtttgca aaacaatatt agaagcttat agagatcttg gtaccagagg aacaggcag
1141 aaaacaagaa tgatgtggtt aattgacgaa ctggtgtttg aaggattcag ggcagaagtt
1201 gtgaagagaa tgcctcaaaa gaagctagag agagaatcca cagaggattt ggtgcagaaa
1261 caatgggaaa ggagagagta tcttgggggtt aatccacaga aacaggaagg ttacagcttt
1321 gttggtcttc acattccagt gggtcgtgtc caagcagtga acatggatga gcttgctcgt
1381 ttagcagaag agtatggttc aggagagctc cggctgactg ttgagcaaaa catcattatt
1441 ccgaacattg agaactcaaa gattgatgca ttgctcaatg aacctcttct gaaacagatt
1501 tcacccgatc cacctattct catgagaaat ttggtggctt gtactggtaa ccaattctgt
1561 gggcaagcca taatcgagac taaagcacgt tcaatgaaga taactgagga ggttcaacgg
1621 ctagtctctg tgactcagcc cgtgaggatg cactggactg gttgcccaaa ttcatgtgga
1681 caagttcaag ttgcagatat cggatttatg ggatgcctga caagaaagga aggaaagaca
1741 gtggaaggcg ctgatgtttt cttgggtggc agaataggga ctgactcaca cttgggagat
1801 atttataaga agtctgtccc ctgtgaagat ttggtaccaa taattgtgga cttactagtt
1861 aacaactttg gtgctgttcc aagagagaga gaagaacag aagattaatc tcaacatttc
1921 agaatcagct cgtggcttta ctcaacatag taaattggac gttgatggaa tgtgcttacc
1981 atattaagat atttccaagg tacagaactg gtggagctgt tgttggaagt tagtagaata
2041 atcagaacat gagctcttct tgacctgcta tgtgtgacat tccacgatgc aaatacttgt
2101 acttgtttca gaatattcac ccggtgtatt gttttggaaa agagctgatc caaactaaaa
2161 ggtttttgaa ttgtgggatt cctaataata gattttttaa aaatgtaatt taataatcat
2221 acatttcaat ttttacctat tattatattc tttgttaaaa aaaaaaaaa aaaaaa
```

SEQ ID NO:19

```
   1 MASFSVKFSA TSSLTSSKRF SKLHATPPQT VAVPPSGAVE VAAERLEPRL EERDGYWVLK
  61 EKFRKGINPA EKAKIEKEPM KLFTENGIED IAKISLEEIE KSKLAKDDID VRLKWLGLFH
 121 RRKHQYGRFM MRLKLPNGIT TSAQTRYLAS VIRKYGKDGC ADVTTRQNWQ IRGVVLPDVP
 181 EILKGLDEVG LTSLQSGMDN VRNPVGNPLA GIDPQEIVDT RPYANLLSNL LSQYVTANFR
 241 GNLSVHNLPR KWNVCVIGSH DLYEHPHIND LAYMPATKDG RFGFNLLVGG FFSPKRCAEA
 301 IPLDAWVPAD DVVPVCKTIL EAYRDLGTRG NRQKTRMMWL IDELGVEGFR AEVVKRMPQK
 361 KLERESTEDL VQKQWERREY LGVNPQKQEG YSFVGLHIPV GRVQADDMDE LARLAEEYGS
 421 GELRLTVEQN IIIPNIENSK IDALLNEPLL KQISPDPPIL MRNLVACTGN QFCGQAIIET
 481 KARSMKITEE VQRLVSVTQP VRMHWTGCPN SCGQVQVADI GFMGCLTRKE GKTVEGADVF
 541 LGGRIGTDSH LGDIYKKSVP CEDLVPIIVD LLVNNFGAVP REREEAED
```

Figure 21

SEQ ID NO:20

```
   1 caccaccacc accaccacca ccaccaccac cacogtctcc agccatggcc tcctccgcct
  61 ccctgcagcg cttcctcccc ccgtacccca acgcggcagc atcccgctgc cgccctcccg
 121 gcgtccgcgc ccgcccgtg cagtcgtcga cggtgtccgc accgtcctcc tcgactccgg
 181 cggcggacga ggccgtgtcg gcggagcggc tggagccgcg ggtggagcag cgggagggcc
 241 ggtactgggt gctcaaggag aagtaccgga cggggctgaa cccgcaggag aaggtgaagc
 301 tggggaagga gccatgtca ttgttcatgg agggcggcat caaggagctc gccaagatgc
 361 ccatggagga gatcgaggcc gacaagctct ccaaggagga catcgacgtg cggctcaagt
 421 ggctcggcct cttccaccgc cgcaagcatc agtatgggcg gttcatgatg cggctgaagc
 481 tgccaaacgg tgtgacgacg agcgagcaga cgaggtacct ggcgagcgtg atcgaggcgt
 541 acggcaagga gggctgcgcc gacgtgacaa cccgccagaa ctggcagatc cgcggcgtca
 601 cgctcccga cgtgccggcc atcctcgacg ggctcaacgc cgtcggcctc accagcctcc
 661 agagcggcat ggacaacgtc cgcaaccccg tcggcaaccc gctcgccggc atcgacccg
 721 acgagatcgt cgacacgcga tcctacacca acctcctctc ctcctacatc accagcaact
 781 tccagggcaa ccccaccatc accaacctgc cgaggaagtg gaacgtgtgc gtgatcgggt
 841 cgcacgatct gtacgagcac ccacacatca acgacctcgc gtacatgccg gcggtgaagg
 901 gcggcaagtt cgggttcaac ctcctcgtcg gcggggttcat aagccccaag aggtgggagg
 961 aggcgctgcc gctcgacgcc tgggtccccg gcgacgacat catcccggtg tgcaaggccg
1021 ttctcgaggc gtaccgcgac ctcggcacca gggcaaccg ccagaagacc cgcatgatgt
1081 ggctcatcga cgaacttcga atggaggctt tccggtcgga ggtggagaag aggatgccga
1141 acggcgtgct ggagcgccg gcgccggagg acctcatcga caagaaatgc cagaggaggg
1201 actacctcgg cgtgcaccg cagaagcagg aagggatgtc ctacgtcggc ctgcacgtgc
1261 ccgtcggccg ggtgcaggcg gcggacatgt tcgagctcgc acgcctcgcc gacgagtacg
1321 gctccggcga gctccgcctc accgtggagc agaacatcgt gatcccgaac gtcaagaacg
1381 agaaggtgga ggcgctgctc tccgagccgc tgcttcagaa gttctccccg cagccgtcgc
1441 tgctgctcaa gggcctcgtc gcgtgcaccg gcaaccagtt ctgcggccag gccatcatcg
1501 agacgaagca gcgggcgctg ctggtgacgt cgcaggtgga gaagctcgtg tcggtgcccc
1561 gggcggtgcg gatgcactgg accggctgcc caacagctg cggccaggtg caggtcgccg
1621 acatcggctt catgggctgc ctcaccaagg acagcgccgg caagatcgtt gaggcggccg
1681 acatcttcgt cggcggccgc gtcggcagcg actcgcacct cgccggcgcg tacaagaagt
1741 ccgtgccgtg cgacgagctg gcgccgatcg tcgccgacat cctggtcgag cggttcggg
1801 ccgtgcggag ggagagggag gaggacgagg agtaggaaca cagactgggg tgttttgctt
1861 gctccggtga tctctcgccg tccttgtaaa gtagacgaca atatgcctc gccatggca
1921 cgcttgtact gtcacgtttt ggtttgatct tgtagcccaa aagttgtgtt cattctcgtt
1981 acagtcttac agaggatgat tgattgataa ataaagaaga aacagattct gtcaagtttg
2041 gcaccgatgc gaagtacatt gccgtaggtt ctatggatcg taacctacgg atatttgggc
2101 atccggaga agatgatcaa atggacgacg caaagccatc ggaagagtga tgaaaccaat
2161 tgtacttcat tttggcctgcg taaattgctc cctgtttgtg tgttttgacg gtggatgagc
2221 tggctgagat tggaggcaca taacaacggg agacgagaag ttccttgcag gagcaatttg
2281 gtgggctttg gtcgatgtaa acaaatttga cattgttatt gtatttgtag gccttactac
2341 ctaatgagga tacggtttgt tttggagatg aatacaatgc tgaagtgctc gacttgcgga
2401 catgccaaaa
```

SEQ ID NO:21

```
  1 MASSASLQRF LPPYPHAAAS RCRPPGVRAR PVQSSTVSAP SSSTPAADEA VSAERLEPRV
 61 EQREGRYWVL KEKYRTGLNP QEKVKLGKEP MSLFMEGGIK ELAKMPMEEI EADKLSKEDI
121 DVRLKWLGLF HRRKHQYGRF MMRLKLPNGV TTSEQTRYLA SVIEAYGKEG CADVTTRQNW
181 QIRGVTLPDV PAILDGLNAV GLTSLQSGMD NVRNPVGNPL AGIDPDEIVD TRSYTNLLSS
241 YITSNFQGNP TITNLPRKWN VCVIGSHDLY EHPHINDLAY MPAVKGGKFG FNLLVGGFIS
301 PKRWEEALPL DAWVPGDDII PVCKAVLEAY RDLGTRGNRQ KTRMMWLIDE LGMEAFRSEV
361 EKRMPNGVLE RAAPEDLIDK KWQRRDYLGV HPQKQEGMSY VGLHVPVGRV QAADMFELAR
421 LADEYGSGEL RLTVEQNIVI PNVKNEKVEA LLSEPLLQKF SPQPSLLLKG LVACTGNQFC
481 GQAIIETKQR ALLVTSQVEK LVSVPRAVRM HWTGCPNSCG QVQVADIGFM GCLTKDSAGK
541 IVEAADIFVG GRVGSDSHLA GAYKKSVPCD ELAPIVADIL VERFGAVRRE REEDEE
```

Figure 22

SEQ ID NO:22

```
   1 catcatcttc atcttcatct tcatcattca tagttgcaag aaacagagca accaaaaaaa
  61 atggcatcac ttccagtcaa caagatcata ccatcatcaa cgacattact gtcatcgtcg
 121 aacaacaaca gaagaagaaa taactcatca attcgatgcc agaaggcggt ttcacccgcg
 181 gcagaaacgg ctgcagtgtc gccgtctgtg gacgcggcga ggctggagcc gagagtggag
 241 gagagagatg ggttttgggt attgaaggag gaatttagga gtgggattaa cccagctgag
 301 aaagttaaga ttgagaaaga cccaatgaag ttgtttattg aggatgggat tagtgatctt
 361 gctactttgt caatggagga agttgataaa tctaagcata ataaggatga tattgatgtt
 421 agactcaagt ggcttggact tttccatcgc cgtaaacatc actatgggag attcatgatg
 481 aggttgaagc tgccgaatgg ggtaacaacg agtgagcaga cacgtacct agcaagcgtg
 541 atcaagaagt acggaaaaga tggatgtgcg gatgtaacaa caaggcaaaa ctggcaaatt
 601 agaggagttg ttctgcctga tgtgccagag atcatcaaag ggctggaatc cgttggtctt
 661 accagcttac agagtgggat ggacaatgta aggaacccctg taggtaaccc tcttgcagag
 721 attgaccctc atgaaattgt tgacaccga cctttttacca acctaatttc ccaatttgtc
 781 actgccaatt cgcgtggaaa cctttctatt accaatctgc caaggaagtg aatccatgt
 841 gttattgggt cccatgatct ttatgagcat ccacacatca atgaccttgc ttacatgcct
 901 gctacaaaga atgggaaatt cggggtttaat ttgttggttg gaggattctt tagcatcaaa
 961 agatgtgaag aggcaatccc actagacgct tgggtctcag cagaagatgt ggttcctgta
1021 tgcaaagcta tgcttgaagc tttcagggac cttggctta gaggaaacag gcagaagtgc
1081 agaatgatgt ggcttattga tgagcttggt atggaagcat tcagggggaga ggttgagaag
1141 agaatgcctg agcaagttct agaaagagca tcctcagaag agctggttca gaaggactgg
1201 gagagaagag aatacttagg agttcaccct cagaaacaac aaggacttag ctttgtgggt
1261 ctccacattc ctgtgggccg tctgcaagct gatgagatgg aagagttagc ccgtatagct
1321 gatgtgtatg gatcagggga gctccgtctg acagtagagc agaacataat catcccaaat
1381 gttgaaaact caagataga ttcactacta acgagcctc tgttaaaaga gcgttactcc
1441 cctgaaccac ccatcttgat gaaggggctt gtggcctgta cggggagcca attttgtgga
1501 caagccatta tcgagaccaa ggctagggca ctcaaggtga cagaagaggt acaacgacta
1561 gtgtctgtaa cacggcctgt taggatgcat tggaccgggt gtcctaatag ttgtggtcaa
1621 gtacaagtgg ctgatattgg gttcatggt tgcatgacta gggatgagaa cggtaagcct
1681 tgtgaaggag ctgatgtgtt tgtaggagga cgtataggaa gtgactcgca tctaggagac
1741 atttacaaga aggcagtccc atgtaaagat ttggtgcctg ttgttgctga gatattgatc
1801 aaccaattcg gtgctgttcc tagggagagg gaagaggcag agtagtagct agactgtttt
1861 gggtgcctgt tcttgttaac tgttatcggt attcggtaat tacttgtaat atttgcattt
1921 tttttcaagc atataattaa attgcataaa gatcccttgt atgtctgcat aacaagatac
1981 tcagttatgt aatgtcaata gcaggttac tttgtttatt caataggcac tgtgaaaggg
2041 aaagttcatt attcatttct ca
```

SEQ ID NO:23

```
  1 MASLPVNKII PSSTTLLSSS NNNRRRNNSS IRCQKAVSPA AETAAVSPSV DAARLEPRVE
 61 ERDGFWVLKE EFRSGINPAE KVKIEKDPMK LFIEDGISDL ATLSMEEVDK SKHNKDDIDV
121 RLKWLGLFHR RKHHYGRFMM RLKLPNGVTT SEQTRYLASV IKKYGKDGCA DVTTRQNWQI
181 RGVVLPDVPE IIKGLESVGL TSLQSGMDNV RNPVGNPLAG LDPHEIVDTR PFTNLISQFV
241 TANSRGNLSI TNLPRKWNPC VIGSHDLYEH PHINDLAYMP ATKNGKFGFN LLVGGFFSIK
301 RCEEAIPLDA WVSAEDVVPV CKAMLEAFRD LGFRGNRQKC RMMWLIDELG MEAFRGEVEK
361 RMPEQVLERA SSEELVQKDW ERREYLGVHP QKQQGLSFVG LHIPVGRLQA DEMEELARIA
421 DVYGSGELRL TVEQNIIIPN VENSKIDSLL NEPLLKERYS PEPPILMKGL VACTGSQFCG
481 QAIIETKARA LKVTEEVQRL VSVTRPVRMH WTGCPNSCGQ VQVADIGFMG CMTRDENGKP
541 CEGADVFVGG RIGSDSHLGD IYKKAVPCKD LVPVVAEILI NQFGAVPRER EEAE
```

Figure 23

SEQ ID NO:24

```
   1 tttctattaa atttctggca ccttcattgc caaatccagc tagattttcc aagaatgctg
  61 tcaagctcca cgcaactccg ccgtctgtgg cagcgccgcc agctggtgct ccagaggttg
 121 ctgctgagag gctagaaccc agagttgagg aaaaagatgg ttattggata ctcaaggagc
 181 agtttagaaa aggcataaat cctcaagaaa aggtcaagat tgagaagcaa cctatgaagt
 241 tgttcatgga aaatggtatt gaagagcttg ctaagatacc cattgaagag atagatcagt
 301 ccaagcttac taaggatgat attgatgtta ggcttaagtg gcttggcctc ttccatagga
 361 gaaagaacca atatgggcgg ttcatgatga gattgaagct tccaaatgga gtaacaacga
 421 gtgcacagac tcgatacttg gcgagtgtga taaggaaata cgggaaagaa ggatgtgctg
 481 atattacaac gaggcaaaat tggcagattc gtggagttgt actgcctgat gtgcccgaga
 541 tactaaaggg actagcagaa gttgggttga ccagtttgca gagtgcatg gacaatgtca
 601 ggaatccagt aggaaatcct cttgctggaa ttgatccaga agaaatagta gacacagggc
 661 cttacactaa tttgctctcc caatttatca ctggcaattc acgaggcaat cccgcagttt
 721 ctaacttgcc aaggaagtgg aatccgtgcg tagtaggctc tcatgatctt tatgaacatc
 781 cccatatcaa cgatctcgcg tacatgcctg ccacgaaaga tggacgattt ggattcaacc
 841 tgcttgtggg tgggttcttc agcgcaaaaa gatgtgatga ggcaattcct cttgatgcat
 901 gggttccagc tgatgatgtt gttccggttt gcaaagcaat actggaagct tttagagatc
 961 ttggtttcag agggaacaga cagaaatgta aatgatgtg gttaatcgat gaactgggtg
1021 tagaaggatt cagggcagag gtcgagaaga gaatgccaca gcaagagcta gagagagcat
1081 ctccagagga cttggttcag aaacaatggg aagaagaga ttatcttggt gtacatccac
1141 aaaaacaaga aggctacagc tttattggtc ttcacattcc agtgggtcgt gttcaagcag
1201 acgatatgga tgagctagct cgtttagctg atgagtatgg ttcaggagag atccggctta
1261 ctgtgaaaca aacattatt attcccaaca ttgagaactc aaagattgag gcactgctca
1321 aagagcctgt tctgagcaca ttttcacctg atccacctat tctcatgaaa ggtttagtgg
1381 cttgtactgg taaccagttt tgtggacaag ccataatcga gactaaagct cgttccctga
1441 tgataactga agaggttcaa cggcaagttt ctttgacacg gccagtgagg atgcactgga
1501 caggctgccc gaatacgtgt gcacaagttc aagttgcgga cattggattc atgggatgcc
1561 tgactagaga taagaatgga aagactgtgg aaggcgccga tgtttctta ggaggcagaa
1621 tagggagtga ttcacatttg ggagaagtat ataaagaggc tgttcccttgt gatgatttgg
1681 taccacttgt tgtggactta ctagttaaca actttggtgc agttccacga gaaagagaag
1741 aaacagaaga ctaataaaat ttagaatagt tggtgatttt gctgtgttca taacatgtaa
1801 tgtatgataa atcaatgcaa acatttctac ctacgtgag
```

SEQ ID NO:25

```
   1 SIKFLAPSLP NPARFSKNAV KLHATPPSVA APPAGAPEVA AERLEPRVEE KDGYWILKEQ
  61 FRKGINPQEK VKIEKQPMKL FMENGIEELA KIPIEEIDQS KLTKDDIDVR LKWLGLFHRR
 121 KNQYGRFMMR LKLPNGVTTS AQTRYLASVI RKYGKEGCAD ITTRQNWQIR GVVLPDVPEI
 181 LKGLAEVGLT SLQSGMDNVR NPVGNPLAGI DPEEIVDTGP YTNLLSQFIT GNSRGNPAVS
 241 NLPRKWNPCV VGSHDLYEHP HINDLAYMPA TKDGRFGFNL LVGGFFSAKR CDEAIPLDAW
 301 VPADDVVPVC KAILEAFRDL GFRGNRQKCR MMWLIDELGV EGFRAEVEKR MPQQELERAS
 361 PEDLVQKQWE RRDYLGVHPQ KQEGYSFIGL HIPVGRVQAD DMDELARLAD EYGSGEIRLT
 421 VEQNIIIPNI ENSKIEALLK EPVLSTFSPD PPILMKGLVA CTGNQFCGQA IIETKARSLM
 481 ITEEVQRQVS LTRPVRMHWT GCPNTCAQVQ VADIGFMGCL TRDKNGKTVE GADVFLGGRI
 541 GSDSHLGEVY KKAVPCDDLV PLVVDLLVNN FGAVPREREE TED
```

Figure 24

SEQ ID NO:26

```
   1 atggcatctt ttctgttaa attctcagca acttcattgc caaatcctaa cagattttcc
  61 aggactgcta agcttcatgc aacaccgccg cagacggtgg cagtaccacc atctggggag
 121 gcggagatag cttccgagag gctagagcct agagtagagg aaaaagatgg gtattgggta
 181 ctcaaggaaa aattcagaca agggataaat ccagctgaaa aggccaagat tgagaagaa
 241 ccaatgaaat tatttatgga aaatggtatt gaagatcttg ctaagatctc acttgaagag
 301 atcgaagggt ctaagcttac taaagatgat attgatgtta ggctcaagtg gcttggcctt
 361 ttccatagga gaaagcatca ttatggccga ttcatgatgc gattgaagct tccaaatggg
 421 gtaacaacga gtgcccaaac tcgatactta gccagtgtga taaggaaata tggaaaagat
 481 ggatgtggtg atgtgactac aaggcaaaat tggcagattc gcggggttgt actacctgat
 541 gtacccgaga ttctaaaggg actggatgaa gttggcttga ccagtctgca aagtggcatg
 601 gacaacgttc gaaatccggt gggaaatcct ctggcgggga ttgatccaca tgaaattgta
 661 gacacaaggc cttacactaa tttgctctcc caatatgtta ctgccaattc tcgtgccaat
 721 ccggctgtta ctaacttgcc aaggaagtgg aatgtatgtg taataggggtc acatgatctt
 781 tatgagcatc cccatatcaa tgatcttgcc tatatgccgg catcaaaaga tggacgattt
 841 ggattcaacc tgcttgtggg tggattcttc agtccgaagc gatgtgcaga ggcagttcct
 901 ctagatgcat gggttccagc tgatgacgtg gtccctgttt gcaaagcaat attagaagct
 961 tatagagatc ttggtaccag agggaacagg caaaaaacaa gaatgatgtg gttagttgat
1021 gaactgggcg ttgaaggatt cagggcagag gtcgtaaaga gaatgcctca acaaaagcta
1081 gatagagaat caacagagga cttggttcaa aaacaatggg aaaggagaga atacctttggc
1141 gtgcatccgc agaaacaaga aggatacagc tttgttggcc ttcacattcc ggtaggtcgt
1201 gtccaagcag atgacatgga cgagctagct cgtttagcgg ataactatgg ttcaggagag
1261 ctccggttga ctgttgaaca gaacatcatt attcccaacg ttgagaactc aaagatcgag
1321 tcattgctca atgagcctct cttaaagaac agattttcga ccaatccacc tattctcatg
1381 aaaaatctgg tggcttgtac tggtaaccaa ttttgcgggc aagccataat tgagactaaa
1441 gcgcgttcca tgaagataac tgaggaggta caacgactag tttctgtgac aaagccggtg
1501 aggatgcatt ggactggttg cccgaattca tgtgacaag ttcaagtcgc ggatattgga
1561 tttatgggat gcttgacaag aaaagaaggg aaaactgtag aagtgctga tgtttatttg
1621 ggaggcagaa tagggagtga ctcacatttg ggagatgttt ataagaaatc agtaccttgt
1681 gaggatttgg tgccaataat tgtggactta ctagttaaca actttggtgc tgttccaaga
1741 gaaagagaag aagcagaaga ttaa
```

SEQ ID NO:27

```
   1 MASFSVKFSA TSLPNPNRFS RTAKLHATPP QTVAVPPSGE AEIASERLEP RVEEKDGYWV
  61 LKEKFRQGIN PAEKAKIEKE PMKLFMENGI EDLAKISLEE IEGSKLTKDD IDVRLKWLGL
 121 FHRRKHHYGR FMMRLKLPNG VTTSAQTRYL ASVIRKYGKD GCGDVTTRQN WQIRGVVLPD
 181 VPEILKGLDE VGLTSLQSGM DNVRNPVGNP LAGIDPHEIV DTRPYTNLLS QYVTANFRGN
 241 PAVTNLPRKW NVCVIGSHDL YEHPHINDLA YMPASKDGRF GFNLLVGGFF SPKRCAEAVP
 301 LDAWVPADDV VPVCKAILEA YRDLGTRGNR QKTRMMWLVD ELGVEGFRAE VVKRMPQQKL
 361 DRESTEDLVQ KQWERREYLG VHPQKQEGYS FVGLHIPVGR VQADDMDELA RLADNYGSGE
 421 LRLTVEQNII IPNVENSKIE SLLNEPLLKN RFSTNPPILM KNLVACTGNQ FCGQAIIETK
 481 ARSMKITEEV QRLVSVTKPV RMHWTGCPNS CGQVQVADIG FMGCLTRKEG KTVEGADVYL
 541 GGRIGSDSHL GDVYKKSVPC EDLVPIIVDL LVNNFGAVPR EREEAED
```

Figure 25

SEQ ID NO:28

```
   1 atggcatctt tttctattaa atttctggca ccttcattgc caaatccagc tagattttcc
  61 aagaatgctg tcaagctcca tgcaacaccg ccgtctgtgg cagcgccgcc aactggtgct
 121 ccagaggttg ctgctgagag gctagaaccc agagttgagg aaaaagatgg ttattggata
 181 ctgaaagagc agtttagaaa aggcataaat cctcaagaaa aggtcaagat tgagaaggaa
 241 cctatgaagt tgttcatgga aaatggtatt gaagagcttg ctaagatacc cattgaagag
 301 atagatcagt ccaagcttac taaggatgat attgatgtta ggcttaagtg gcttggcctc
 361 ttccatagga gaaagaatca atatggcgg ttcatgatga gattgaagct tccaaatgga
 421 gtaacaacga gtgcacagac tcgatactta gcgagtgtga taggaaata cggaaggaa
 481 ggatgtgctg atattacgac aaggcaaaat tggcagattc gtggagttgt actgcctgat
 541 gtgccggaga tactaaaggg actagcagaa gttgggttga ccagtttgca gagtggcatg
 601 gacaatgtca ggaatccagt aggaaatcct ctggctggaa ttgatccaga agaaatagta
 661 gacacaaggc cttacactaa tttgctctcc caatttatca ctggcaattc acgaggcaat
 721 cccgcagttt ctaacttgcc aaggaagtgg aatccgtgtg tagtaggctc tcatgatctt
 781 tatgagcatc cccatatcaa cgatctcgcg tacatgcctg ccacgaaaga cgggcgattt
 841 ggattcaacc tgcttgtggg agggttcttc agtgcaaaaa gatgtgatga ggcaattcct
 901 cttgatgcat gggttccagc cgatgatgtt gttccggttt gcaaagcaat actggaagct
 961 tttagagatc ttggttttcag agggaacaga cagaaatgta gaatgatgtg gttaatcgat
1021 gaactggggtg tagaaggatt cagggcagag gtcgagaaga gaatgccaca gcaacaacta
1081 gagagagcat ctccagaaga cttggttcag aaacaatggg aagaagaga ttatcttggt
1141 gtacatccac aaaaacaaga aggctacagc tttatcggcc ttcacattcc agtgggtcgt
1201 gttcaagcag acgatatgga tgagctagct cgtttagctg atgaatatgg ttcaggagag
1261 atccggctta ctgtggaaca aaacattatt attcccaata ttgagacctc aaaaattgag
1321 gcactgctca agagcctgt tctgagcaca tttttcacctg atccacctat tctcatgaaa
1381 ggtttagtgg cttgtactgg taaccagttt tgtggacaag ccataatcga gactaaagct
1441 cgttccttga agataactga agaggttcaa cggcaagttt ctttgacaaa accagtaagg
1501 atgcactgga caggctgccc gaatacgtgt gcacaagttc aagttgcgga cattggattc
1561 atgggatgcc tgactagaga taagaacggg aagactgtgg aaggcgccga tgtttttttta
1621 ggaggaagaa taggagatga ttcacatttg ggagaagtat ataagaaggc tgttccttgt
1681 gatgatttgg taccacttgt tgtggacttg ctagttaaca actttggtgc agttccacga
1741 gaaagagaag aaacagaaga ttaa
```

SEQ ID NO:29

```
   1 MASFSIKFLA PSLPNPARFS KNAVKLHATP PSVAAPPTGA PEVAAERLEP RVEEKDGYWI
  61 LKEQFRKGIN PQEKVKIEKE PMKLFMENGI EELAKIPIEE IDQSKLTKDD IDVRLKWLGL
 121 FHRRKNQYGR FMMRLKLPNG VTTSAQTRYL ASVIRKYGKE GCADITTRQN WQIRGVVLPD
 181 VPEILKGLAE VGLTSLQSGM DNVRNPVGNP LAGIDPEEIV DTRPYTNLLS QFITGNSRGN
 241 PAVSNLPRKW NPCVVGSHDL YEHPHINDLA YMPATKDGRF GFNLLVGGFF SAKRCDEAIP
 301 LDAWVPADDV VPVCKAILEA FRDLGFRGNR QKCRMMWLID ELGVEGFRAE VEKRMPQQQL
 361 ERASPEDLVQ KQWERRDYLG VHPQKQEGYS FIGLHIPVGR VQADDMDELA RLADEYGSGE
 421 IRLTVEQNII IPNIETSKIE ALLKEPVLST FSPDPPILMK GLVACTGNQF CGQAIIETKA
 481 RSLKITEEVQ RQVSLTKPVR MHWTGCPNTC AQVQVADIGF MGCLTRDKNG KTVEGADVFL
 541 GGRIGSDSHL GEVYKKAVPC DDLVPLVVDL LVNNFGAVPR EREETED
```

Figure 26

SEQ ID NO:30

```
   1 atggcatctt tttctgttaa attctcagct acttcattac caaatcataa aagattttca
  61 aagctacatg caacaccgcc gcagacggtg gctgtagccc catctgggc ggcggagata
 121 gcatcggaga ggttagagcc tagagtagaa gaaaaagatg ggtattgggt acttaaggaa
 181 aaattcagac aagggataaa tccagctgaa aaagctaaga ttgagaagga accaatgaaa
 241 ttgtttatgg aaaatggtat tgaagatcta gctaagatct cacttgaaga gatcgaaggg
 301 tctaagctta ctaaagatga tattgatgtt aggctcaagt ggcttggcct tttccatagg
 361 agaaagcatc actatggccg attcatgatg agattgaagc ttccaaatgg ggtaacaacg
 421 agttcccaaa ctcgatactt agccagtgtg ataaggaaat atgggaaaga tggatgtgct
 481 gatgtgacga caaggcaaaa ttggcagatt cgtggggttg tactacctga tgtacccgag
 541 attctaaagg gactggatga agttggctta accagtctgc agagtggcat ggacaatgtt
 601 agaaatccgg tgggaaatcc tctggcgggg attgatccac atgaaattgt agacacaagg
 661 ccttacacta atttgctctc ccaatatgtt actgccaatt ttcgtggcaa tccggctgtg
 721 actaacttgc caaggaagtg gaatgtatgt gtaataggt cacacgatct ttatgagcat
 781 ccccagatca acgatcttgc ctatatgccg gcaacaaaag atggacgatt tggattcaac
 841 ctgcttgtgg gtggattctt cagtccgaag cgatgtgcag aggcagttcc tcttgatgca
 901 tgggttccag ctgatgacgt agtccctgtt tgcaaagcaa tattagaagc ttatagagat
 961 cttggcacca gagggaacag gcagaaaaca agaatgatgt ggttagttga tgaactgggc
1021 gttgaaggat tcagggcaga ggttgtaaag agaatgcctc aacaaaagct agatagagaa
1081 tcaacagagg acttggttca aaaacaatgg gaaggagag aataccttgg cgtgcatcca
1141 cagaaacaag aagggtactg cttttgttggt cttcacattc cagtggtcg tgtccaagca
1201 gatgacatgg acgagctagc tcgtttggcc gatgagtatg gttccggaga gctccggctg
1261 actgttgaac aaacatcat tattcccaat gttaagaact caaagatcga ggcattgctc
1321 aatgaacctc tcttaaagaa cagattttca accgatccac ctattctcat gaaaaatttg
1381 gtcgcttgta ctggtaacca attttgcggg aaagccataa ttgagactaa ggcacgatcc
1441 atgaaaataa ctgaggaggt tcaactacta gtttctataa cgcagcctgt gaggatgcat
1501 tggactggtt gcccgaattc atgtgcacaa gttcaggtcg cggatattgg atttatggga
1561 tgcttgacaa gaaaagaagg aaaaactgta gaaggtgctg atgtttattt gggaggcaga
1621 atagggagtg actcacattt gggagatgtt tataagaaat cagtaccttg tgaggatttg
1681 gtgccaataa ttgtggactt actagttgac aactttggtg ctgttccaag agaaagagaa
1741 gaagcagaag attaa
```

SEQ ID NO:31

```
   1 MASFSVKFSA TSLPNHKRFS KLHATPPQTV AVAPSGAAEI ASERLEPRVE EKDGYWVLKE
  61 KFRQGINPAE KAKIEKEPMK LFMENGIEDL AKISLEEIEG SKLTKDDIDV RLKWLGLFHR
 121 RKHHYGRFMM RLKLPNGVTT SSQTRYLASV IRKYGKDGCA DVTTRQNWQI RGVVLPDVPE
 181 ILKGLDEVGL TSLQSGMDNV RNPVGNPLAG IDPHEIVDTR PYTNLLSQYV TANFRGNPAV
 241 TNLPRKWNVC VIGSHDLYEH PQINDLAYMP ATKDGRFGFN LLVGGFFSPK RCAEAVPLDA
 301 WVPADDVVPV CKAILEAYRD LGTRGNRQKT RMMWLVDELG VEGFRAEVVK RMPQQKLDRE
 361 STEDLVQKQW ERREYLGVHP QKQEGYSFVG LHIPVGRVQA DDMDELARLA DEYGSGELRL
 421 TVEQNIIIPN VKNSKIEALL NEPLLKNRFS TDPPILMKNL VACTGNQFCG KAIIETKARS
 481 MKITEEVQLL VSITQPVRMH WTGCPNSCAQ VQVADIGFMG CLTRKEGKTV EGADVYLGGR
 541 IGSDSHLGDV YKKSVPCEDL VPIIVDLLVD NFGAVPRERE EAED
```

Figure 27

SEQ ID NO:32

```
   1 ggccgcacag ggcgcgcccg cgcggccgtc tccgtgccgc cgccggcggg ggagcaggtc
  61 ccgacggagc ggctggagcc gagggtcgag gagcgggcgg gcgggtactg ggtcctcaag
 121 gagaagtacc gggcggggct gaacccgcag gagaaggtga agctggagaa ggagcccatg
 181 gcgctgttca tggagggcgg catccaggac ctggccaggg tccccatgga gcagatcgac
 241 gccgccaagc tcaccaagga cgacgtcgac gtccgcctca agtggctcgg cctcttccac
 301 cgccgcaagc accagtacgg gcggttcatg atgcggctga agctgcccaa cggcgtgacg
 361 acgagcgagc agacgcggta cctggcgagc gtcatcgagg cgtacgcgc cgacgggtgc
 421 gcggacgtga ccacccggca gaactggcag atccgcgggg tgacgctccc ggacgtcccg
 481 gccatcctgg acggcctccg cgccgtcggc ctcaccagcc tgcagagcgg catggacaac
 541 gtgcgcaacc ccgtcggcaa cccgctcgcc ggcgtcgacc cccacgagat cgtcgacacg
 601 cgccctaca ccaaccttct ctcctcctac gtcaccaaca actcccaggg gaacccaca
 661 atcaccaacc tgccgaggaa atggaacgtc tgcgtcatcg gctcgcatga cctgtacgag
 721 caccgcaca tcaacgacct cgcgtacatg ccggccgtca aggacggcga gttcggcttc
 781 aaccttctgg tgggcgggtt catcagcccc aagaggtggg ccgaggcgtt gccgctcgac
 841 gcctggagtcg ccggggacga cgtcgtcccc gtgtgcaagg ccatcctcga ggcgtaccgg
 901 gacctcggct ccaggggcaa ccggcagaag acgcgcatga tgtggctcat cgacgagctc
 961 gggatggagg tgttccggtc ggaggtggag aagaggatgc cgaacgggt gctggagcgc
1021 gccgcgccgg aggacctcgt cgacaagcgc tgggagcggc gggactacct cggcgtgcac
1081 ccgcagaagc aggaaggcct gtcgtacgtg ggcctccacg tgccggtggg ccggctgcag
1141 gccgcggaca tgttcgagct ggcgcggctc gccgacgagt acggcaccgg cgagctccgg
1201 ctcacggtgg agcagaacat cgtgctcccc aacgtcagca acgagaggct cgacgcgctg
1261 ctggcggagc cgctgctgca ggagcagcgg ctctcgccgc ggccgtcgat gctgctcagg
1321 gggctggtgg cgtgcacggg caaccagttc tgcggggcagg ccatcatcga gaccaaggcg
1381 cgggcgctgc aggtggcgcg ggaggtggag aagcgcgtgg ccgtgccgcg gccggtccgc
1441 atgcactgga ccggatgccc caacagctgc ggccaggtgc aggtggcgga catcggcttc
1501 atgggctgcc tcaccaagga cagcgacggc aagatcgtcg aggccgcgga catcttcgtg
1561 ggcggccgga tcggcagcga ctcgcacctg gccgacgtct accggaagtc accggccgtgc
1621 aaggacctgg tgcccatcgt ggccgacctc ttggtggagc ggttcggggc cgtgccgagg
1681 gagagggagg aggatgagga gtaggacctt cgtcaagcgc cggctgggac tgtcctgacc
1741 tattttatga ggtcttgatt ggatgtatat atatattcat cttaatctat atggatttct
1801 gaagtttgat cta
```

SEQ ID NO:33

```
   1 GRTGRARAAV SVPPPAGEQV PTERLEPRVE ERAGGYWVLK EKYRAGLNPQ EKVKLEKEPM
  61 ALFMEGGIQD LARVPMEQID AAKLTKDDVD VRLKWLGLFH RRKHQYGRFM MRLKLPNGVT
 121 TSEQTRYLAS VIEAYGADGC ADVTTRQNWQ IRGVTLPDVP AILDGLRAVG LTSLQSGMDN
 181 VRNPVGNPLA GVDPHEIVDT RPYTNLLSSY VTNNSQGNPT ITNLPRKWNV CVIGSHDLYE
 241 HPHINDLAYM PAVKDGEFGF NLLVGGFISP KRWAEALPLD AWVAGDDVVP VCKAILEAYR
 301 DLGSRGNRQK TRMMWLIDEL GMEVFRSEVE KRMPNGVLER AAPEDLVDKR WERRDYLGVH
 361 PQKQEGLSYV GLHVPVGRLQ AADMFELARL ADEYGTGELR LTVEQNIVLP NVSNERLDAL
 421 LAEPLLQEQR LSPRPSMLLR GLVACTGNQF CGQAIIETKA RALQVAREVE KRVAVPRPVR
 481 MHWTGCPNSC GQVQVADIGF MGCLTKDSDG KIVEAADIFV GGRVGSDSHL ADVYRKSVPC
 541 KDLVPIVADL LVERFGAVPR EREEDEE
```

DECREASING NITRITE CONTENT IN TOBACCO VIA EXPRESSION OF A NITRITE REDUCTASE

CROSS-REFERENCE TO RELATED APPLICATIONS

This application is a continuation-in-part of U.S. Non-Provisional application Ser. No. 12/673,385, filed Jun. 6, 2011; which is a 371 of international PCT Application No. PCT/GB2008/050707 filed Aug. 14, 2008; and United Kingdom Application 0715916.3, filed Aug. 15, 2007; which are herein incorporated by reference in their entirety.

DESCRIPTION OF THE TEXT FILE SUBMITTED ELECTRONICALLY

The contents of the text file submitted electronically herewith are incorporated herein by reference in their entirety: A computer readable formal copy of the Sequence Listing (filename: BTMK_073_01US_SEQList_ST33_5 T25.txt, date recorded: Jan. 16, 2015, file size 75.7 KB)

FIELD OF INVENTION

The present invention relates to a method for producing a transgenic plant. In particular, the invention relates to methods for reducing nitrite content in plants, as well as to transgenic plants obtained by such methods and associated uses.

BACKGROUND OF THE INVENTION

Nitrogen assimilation is of fundamental importance to the growth of plants. Of all the mineral nutrients required by plants, nitrogen is required in the greatest abundance. The main forms of nitrogen taken up by plants in the field are nitrate and ammonia, the principle components of nitrogenous fertilizers. Plants take up either nitrate or ammonium ions from the soil, depending on availability. Nitrate will be more abundant in well-oxygenated, non-acidic soils, whilst ammonium will predominate in acidic or waterlogged soils. Experiments on growth parameters of tobacco (Stöhr, 1999) clearly demonstrated that relative growth rate, chlorophyll content, leaf area and root area increased dramatically in response to increasing nitrate supply.

Roots take up nitrate and ammonia by the action of specific transporters, (Rothstein et al., 1998). In plants there are distinct transport systems that have different affinities for nitrate. The nitrate is then either reduced in the roots by the cytoplasmic enzyme nitrate reductase (NR) and enters the nitrogen assimilatory pathway, or it is transported to the shoots in the xylem. Nitrate is transported from the epidermal and cortical cells of the roots and into the vascular system to be transported to the shoots (Crawford, 1995). It enters the leaf via the apoplast and is transported across the plasma membrane into the mesophyll cells. Here it is either stored in vacuoles or reduced in the cytoplasm and enters the primary nitrogen assimilation pathway. When nitrate is present in excess it is stored in the vacuole. This serves both as an osmoticum and as a source of mineral N to be used when nitrate uptake is minimal (Crawford and Glass, 1998). The nitrate present in the cytoplasm is the starting point of primary nitrogen assimilation.

Nitrate is reduced in the cytosol by the cytoplasmic enzyme nitrate reductase (NR) to nitrite, which itself is rapidly reduced to ammonium by nitrite reductase (NiR) in the chloroplasts of leaves or in the plastids of non-photosynthetic organs (Crawford, 1995, Crete et al., 1997, Tobin and Bowsher, 2005). In the chloroplast the ammonium then enters the glutamine synthetase/glutamate synthase cycle (GS/GOGAT) where it is incorporated into the amino acid pool.

NR is considered to be the rate-limiting factor for growth and nitrate assimilation (Solomonson & Barber, 1990, Tischner, 2000) and is the first committed step of nitrogen assimilation. It catalyses the 2 electron reduction of nitrate to nitrite using NAD(P)H as an electron donor (Wray and Kinghorn, 1989).

There are 3 forms of NR; free NR (active), phosphorylated NR (active pNR), and pNR:14-3-3 (inactive). The ratio of the 3 forms is variable depending on external conditions (Kaiser et al., 2002). This complex regulation of NR controls the reduction of nitrate so that deleterious amounts of nitrite do not accumulate in the cell (Lillo et al., 2003). Lea et al., (2006) demonstrated that it is the post-translational regulation of NR in tobacco plants which has the greatest effect on NR activity and associated metabolite levels. Introducing NR using the constitutive promoter CaMV (35S) and thus deregulating NR at the transcriptional level had little effect on metabolite levels as the post-translational regulatory mechanism was still active. Loss of the post-translational control however, results in chlorosis of young tobacco leaves (Lillo et al., 2003). In tobacco, site-directed mutagenesis of Ser521 to aspartic acid prevents post-translational phosphorylation of NR (Kaiser et al., 2002, Lillo et al., 2003, Lea et al., 2006). When this post-translational control had been destroyed, constitutive activation of NR resulted in nitrite accumulation and chlorotic leaves.

A second function of NR is the reduction of nitrite to nitric and nitrous oxides. Nitric oxide (NO) is known to play an important signalling role in plant defence, growth and development (Wendehenne et al., 2004). NO production only uses 1% of the NR capacity and is dependant on nitrite concentration (Kaiser et al., 2001, Rockel et al., 2002). NO production from nitrite by purified maize NR was competitively inhibited by nitrate (50 µM) and the rate of NO production increased when nitrite levels accumulated as a result of higher nitrate reduction in relation to nitrite reduction (Rockel et al., 2002). In transgenic tobacco with a severe reduction in nitrite reductase (NiR) activity, a corresponding increase in NO emission was reported. This was also accompanied by an increased synthesis of 14-3-3 proteins involved in the regulation of nitrate reduction (Morot-Gaudry-Talarmain et al., 2002), and is likely to be related to attempts at controlling the potentially toxic accumulation of nitrite in the cell.

Nitrite reductase (NiR) is the second enzyme in the nitrate assimilation pathway and involves the transfer of 6 electrons from reduced ferredoxin to nitrite to form ammonium (Wray and Kinghorn, 1989). NiR from green leaves has a molecular mass of 63 kDa and is a monomer (Crété et al., 1997). NiR is found mainly in the chloroplasts of leaves from $C_3$ plants, and in chloroplasts of mesophyll cells of $C_4$ plants, as well as in the plastids of non-green tissues (Tobin and Bowsher, 2005).

The enzyme has been shown to be a metalloprotein (Swarmy et al., 2005) and contains the prosthetic sirohaem group, to which nitrite binds and a 4Fe/4S centre which is likely to be the initial electron acceptor.

NiR consists of 3 domains, folded compactly around the cofactors, sirohaem and a 4Fe/4S cluster. NiR forms a complex with its electron donor ferredoxin and substrate nitrite, the 4Fe/4S cluster receives the electrons from ferredoxin and transfers them to the sirohaem, which in turn transfers them to the substrate nitrite that remains bound until complete reduction to ammonia (Swamy et al., 2005).

NiR is encoded in the nucleus by the NiR gene (Dorbe et al., 1998), therefore the protein must be transported from the cytoplasm to the chloroplasts. The spinach NiR precursor protein is 32 amino acids longer than the mature protein. These additional amino acids are probably the transit peptide sequence directing the NiR to the chloroplast (Wray and Kinghorn, 1989) where this peptide must be cleaved to form the active protein.

Isoforms of NiR have been identified in a number of plants. In tobacco there are four NiR genes: NiR1 and NiR3 encode predominantly leaf specific NiRs and NiR2 and NiR4 encode mainly for root NiRs (Kronenberger et al., 1993, Stohr and Mack, 2001). Homologues of these genes have been found in two ancestral species of tobacco, NiR1 and NiR2 in *Nicotiana tomentosiformis* and NiR3 and NiR4 in *Nicotiana sylvestris* (Kronenberger et al., 1993).

There is only one NiR gene in *A. thaliana*, spinach and soybean, two in maize and hot pepper and three in wild oat (Wray and Kinghorn, 1989). The ratio of leaf to root mRNA of tobacco NiRs was found to be 3:1 (Kato et al., 2004), indicating that the leaf NiR plays a more significant role in nitrate assimilation. Kato et al. (2004) also demonstrated using quantitative RT-PCR that mRNAs for each of the 4 NiR genes were present in both leaves and roots but NiR2 and 4 only accounted for 10% of the total NiR mRNA in leaves. All four were induced after nitrate treatment.

Morot-Gaudry-Talarmain et al. (2002) produced antisense NiR tobacco plants with severe suppression of NiR activity. These plants showed drastically reduced growth and suggest that nitrite cytotoxicity in plants may be ascribed to the production of active nitrogen species such as NO (nitric oxide), $N_2O$ (nitrous oxide) and peroxynitrite, which in turn induces the nitration of tyrosine residues in proteins and phenolic ring structures. NO emission increased the synthesis of proteins such as 14-3-3's and cyclophilins.

NiR activity requires reduced ferredoxin as the electron donor, which is a product of photosynthesis (Tobin and Bowsher, 2005) and takes place in the chloroplast matrix. By isolating intact spinach chloroplasts, it was demonstrated that nitrite reduction can be triggered by illumination at a rate similar to that measured in the intact leaves. DCMU (3(3,4-dichlorophenyl)-1,1-dimethylurea) which interrupts the electron transport chain after PSII, and thus stops the availability of reduced ferredoxin, inhibited this reaction and showed that nitrite reduction is energetically directly linked/coupled to non-cyclic electron transport (Mohr and Schopfer, 1994).

In roots, nitrate assimilation takes place in leucoplasts. The reaction is similar to that which takes place in the chloroplast but is supplied by reduction equivalents (NADPH) via a ferredoxin-NADPH oxidoreductase enzyme from the oxidative pentose phosphate pathway (Tobin and Bowsher 2005).

The incorporation of ammonium into organic compounds is performed through the cyclic action of the enzymes glutamine synthetase (GS) and glutamine-2-oxoglutarate-aminotransferase (GOGAT) (Lea and Miflin, 1974). GS incorporates ammonium into glutamine (Gln) and glutamate (Glu) is derived from Gln by the action of GOGAT (Lea and Miflin, 2003; Glevarec et al., 2004). The process runs as a cycle, one of the glutamate molecules produced being used as a substrate by GS while the other is used for the synthesis of other amino acids. This pathway is of major importance as the Glu and Gln produced are donors for the biosynthesis of major N-containing compounds (Hodges, 2002).

Inputs to the cycle are ammonium, which can originate from several different sources, such as primary nitrate assimilation, photorespiration and nitrogen remobilisation (deaminating activity of glutamate dehydrogenase) and the substrate 2-oxoglutarate (2-OG) which could orginate from the isocitrate-dehydrogenases or amino transferases, but the exact route of 2-OG for ammonium assimiliation is still unclear (Hodges, 2002).

The resulting molecules generated by nitrogen assimilation, glutamine (Gln) and glutamate (Glu), are the nitrogen (N) donors for the synthesis of all the other amino acids and N-containing compounds in the cell, including nucleic acids, cofactors and chlorophyll. Therefore Glu and Gln are referred to as the pivotal amino acids and nitrate reduction and the GS/GOGAT cycle sit at the interface of the nitrogen and carbon (C) metabolism. N and C metabolism must be tightly co-ordinated, as the assimilation of N requires a supply of C skeletons in the form of 2-OG, as well as considerable ATP and reductant necessary for the reduction of nitrate to ammonium, and the incorporation of ammonium into Glu and Gln. This tight co-ordination has been highlighted in several studies by the strong correlation of N assimilation activities and metabolites with those of the photosynthetic carbon assimilation pathway (Martin et al., 2005). In tobacco, when plants were subjected to elevated $CO_2$ levels, uptake of nitrate was enhanced by 7% (Kruse et al., 2002) and coincided with an increase in relative growth rates of 9%.

Nitrogen assimilation is also linked to sulphate assimilation. Sulphur interacts with nitrogen in such a way that a lack of one reduces the uptake and assimilation of the other (Hesse et al., 2004). Micro-array data from *A. thaliana* plants exposed to nitrate demonstrated expression of several sulphate transporters and assimilation genes in response to the nitrate treatment (Wang et al., 2003) in the same way that nitrate transporter and assimilation genes were upregulated. Indeed, both sulphite reductase (SiR) and NiR contain siroheme cofactors and iron-sulphur clusters which are essential for electron transfer. It is also known that SiR and NiR can reduce the substrate of the other enzyme but have much higher affinity for their own (Swamy et al., 2005). Therefore the activity of N assimilation, and particularly NiR, is dependant on the presence of sulphur (Swamy et al., 2005).

Nitrogen, mainly in the form of ammonium and amino acids, is also available to the plant via the pathways which recycle nitrogen, such as those achieved in photorespiration, senescence and amino acid catabolism. Photorespiration occurs when ammonium is released from glycine in the leaves of $C_3$ plants during the conversion of glycine to serine by the mitochondrial enzyme glycine decarboxylase (GDC). The photorespiration pathway can lead to rates of ammonium assimilation of 10 times more than that of nitrate reduction especially when environmental conditions, such as drought, lead to stomatal closing and low carbon dioxide availability in the chloroplasts.

During senescence, the amino acids released following proteolysis are transaminated, so that the amino groups are transferred to Glu. An oxidative deamination reaction catalysed by glutamate dehydrogenase (GDH) is then able to liberate ammonium, 2-OG and reducing power (NADH). The ammonium can then act as a substrate for glutamine and asparagine synthesis and the 2-OG is metabolised in the Krebs cycle (Gleverac et al., 2004).

Theoretically GDH can also act in the aminating direction to synthesise glutamate from ammonium and 2-OG. The role of GDH in ammonium assimilation has been the subject of considerable controversy, which is still ongoing. However there is now considerable evidence that GDH functions predominantly in the deaminating direction in tissues with a low C/N ratio, that are converting amino acids into transport compounds, such as germinating seeds and senescing leaves (Miflin and Habash, 2002).

The regulation of NR and NiR activity is critical in controlling primary nitrogen assimilation throughout the plant and has a significant impact on the growth and development of the plant. However under certain conditions nitrate may accumulate, mainly in green photosynthetically active tissues, where it is stored in the vacuoles of the mesophyll cells. High levels of nitrate accumulation can occur during periods of low temperature and/or solar irradiation (for example, in greenhouse crops during the winter), when there is less photosynthetic capacity to assimilate the stored nitrate, or as a result of high nitrate levels in the soil. An increase in nitrate levels can have a number of deleterious consequences, not only in terms of plant growth but also in terms of human or animal health where the plant is consumed, as well as environmental consequences. Many of the adverse consequences of nitrate accumulation are mediated through the production of nitrite.

Nitrosamines form as part of a chemical reaction between a nitrosating agent and secondary or tertiary amine precursors. The source of nitrosating agents is nitrite which reacts with water to produce common nitrosating agents such as nitrous acid ($HNO_2$), dinitrogen trioxide ($N_2O_3$) and peroxynitrite ($ONOO^-$). This reaction is prevalent at elevated temperatures (such as cooking, smoking or drying processes) or in acidic conditions, such as in the stomach (Lee et al., 2006).

The formation of nitrosamines in the stomach is a result of endogenous nitrosation. Oral bacteria chemically reduce nitrate consumed in food and drink to nitrite, which can form nitrosating agents in the acidic environment of the stomach. These react with amines to produce nitrosamines and cause DNA strand breaks or cross linking of DNA.

Nitrosamines in tobacco are formed by microbial reduction of nitrate to nitrite which happens when the cells break down during senescence and curing, and the cell contents become available to micro-organisms which reside on the leaf Nitrosating agents derived from nitrite react with tobacco alkaloids to form tobacco-specific nitrosamines (TSNAs). Nitrite itself is formed during the leaf browning and stem drying phases. The amount of residual nitrate and nitrite in the leaf plays a major role in the reaction and the amount of TSNAs produced (Staff et al., 2005).

Nitrosamine compounds have been implicated in human cancers. This was first reported in 1956 by John Barnes and Peter Magee who demonstrated that dimethylnitrosamine (DMNA) induced liver tumours in rats. This led to the investigation of the carcinogenic properties of other nitrosamines with approximately 300 being tested and 90% found to be carcinogenic in a wide variety of experimental animals (Ellis et al., 1998). Human population studies have linked nitrosamines to cancers mainly of the oesophagus, oral cavity and pharynx (Isaacson, 2005).

Nitrate may be reduced to nitrite by micro-organisms arising from naturally occurring leaf flora, contamination (Isaacson, 2005) or from gut or oral bacteria (Ellis et al., 1998). As much as 25% of the nitrate ingested is taken up from the blood by the salivary glands to be excreted in the saliva. 20% of this is reduced to nitrite by the facultative anaerobes in the oral cavity which use nitrate as an alternative electron acceptor to oxygen in order to produce ATP. It is the nitrite which acts as the major nitrating agent, as nitrate itself will leave the body unmodified since nitrate cannot be metabolized by human enzymes.

Another problem associated with an excess of nitrate is the formation of methaemoglobin which gives rise to blue baby syndrome, where the oxygen carrying capacity of haemoglobin is blocked by nitrite, causing chemical asphyxiation in infants. Foetal haemoglobin, the predominant form in infants up to 3 months is oxidised more readily to methaemoglobin by nitrite than adult haemoglobin. Red blood cells contain methaemoglobin reductases that convert methaemoglobin back to haemoglobin, but the activity of this enzyme is half what it is in adults. Baby foods which contain vegetables, which are another source of increased nitrate content, are voluntarily measured to be less than 100 ppm and as spinach frequently exceeds this limit, products are often labelled not to be used in infants younger than 3 months (Greer et al., 2005).

As a consequence of these health concerns, a number of regulatory authorities have set limits on the amount of nitrate allowed in leafy green vegetables such as spinach and lettuce (e.g. European Commission Regulation 653/2003), depending on the time of harvest. These limits have resulted in any produce with a high nitrate content being unmarketable. Consequently there have been efforts to reduce nitrate content of plants by managing application of nitrogen-containing fertilisers or improved systems of crop husbandry (Isolovich et al., 2002). Some authorities have also set limits on the amounts of nitrate in drinking water.

An alternative method for modifying plant characteristics is through the use of genetic engineering techniques. The introduction and manipulation of specific coding sequences for targeted traits into plants in order to alter their physiology has proved successful for a number of crop species and model plants like tobacco, wheat, barley, *A. thaliana* and maize. The production of plants which contain herbicide resistant traits are commercially acceptable in some countries, particularly the USA, Spain and China. Crops containing traits which are of benefit to the consumer are also becoming available, such as golden rice (Syngenta) which has a phytoene synthase gene (from maize) and a carotene desaturase gene (from *Erwinia uredovara*) inserted into its genome resulting in increased levels of vitamin A in the crop (Paine et al., 2005). Even so most genetic modification is used in the context of research as a tool to understand the function of specific genes within plants.

The soil bacterium *Agrobacterium tumifaciens* provides the tools for stable insertion of foreign genes into a plant and has been used in the transformation of many plant species, including tobacco, potato, tomato, *A. thaliana*, eucalyptus, etc. (Hoekema et al., 1983, Bendahmane et al., 2000). The *A. tumifaciens* naturally transfers its own plasmid DNA into plant genomes as a means of infecting the plant. *A. tumifaciens* contains a plasmid separate from the bacterial chromosome, known as the Ti plasmid. Within the Ti plasmid there is a region of DNA which can be transferred to the infected plant known as transfer-DNA (T-DNA). Also contained in the Ti plasmid are genes which facilitate the transfer of the T-DNA such as the vir region (a region which confers virulence for infection). A specific gene of interest (or genes) can be inserted into the transfer-DNA (T-DNA) of *A. tumifaciens* and this is then used to infect plants and generate transgenic populations.

As well as the gene of interest, a selectable marker gene is usually part of the T-DNA, such as neomycin phosphotranferase II (NPTII) which confers kanamycin antibiotic resistance to the plants expressing that gene, allowing a method of selection of transformed plants (Angenon et al., 1994). *Agrobacterium*-mediated transfer can result in more than one copy of the T-DNA being inserted into the plant genome. Multiple copies have been shown to lead to down-regulation of gene expression or gene silencing (Vaucheret et al., 1998, Han et al., 2004).

The regulation of NR protein in tobacco, potato and *A. thaliana* has been studied (for example Lea et al., 2006). NR sequences have been cloned and used in both over expression studies (Lea et al., 2004) and down-regulation studies (Lillo et al., 2004).

These studies have resulted in a further understanding of NR post-translational regulation which has been evolved by the plant to avoid the potential problems of nitrite accumulation. When NR was over-expressed or deregulated, nitrate levels were reduced throughout the day and night (Lea et al., 2006) and this caused a build-up of nitrite with ultimately damaging effects (Lillo et al., 2003, Lea et al., 2004). This is likely to be due to the fact that NiR is unable to reduce nitrite during the night in the leaf as the required reductant, reduced ferredoxin, is unavailable in the absence of photosynthesis.

An alternative approach was explored by Stitt et al., (1999), who used a mutant of tobacco with low NR activity, and observed an accumulation in nitrate content in the plant, which would also be undesirable. Contradictory to this, low NR activity in potato leaves resulted in the reduced nitrate levels in transgenic tubers (Djennane et al., 2002). In contrast, NiR has not been studied extensively. Takahashi et al. (2001) produced *A. thaliana* plants over-expressing spinach NiR and found that lines containing more than two copies of the transgene had low levels of mRNA. This phenomena of gene silencing can result from several different mechanisms employed by the plant, such as hyper-methylation of multiple copies which are integrated at one locus and co-suppression from RNAi mechanisms (Vaucheret et al., 1998, Han et al., 2004). Lines with one or two copies of the NiR gene showed significantly higher levels of $^{15}$N-labelled reduced nitrogen. This study focused on improving nitrate assimilation but did not investigate nitrate or nitrite levels in the transgenic plants.

Over-expression of the tobacco NiR genes in tobacco also resulted in a two-fold increase in NiR activity (Crété et al., 1997). However post-transcriptional regulation of tobacco leaf NiR expression was observed, since NiR activity and protein level were strongly reduced on ammonium-containing media despite constitutive expression of NiR mRNA. The effect of this on nitrate or nitrite levels was not reported.

Ozawa and Kawahigashi (2006) isolated a rice NiR gene and over-expressed it in a commercial rice variety (Koshihikari) for use as a selection system in the production of transformed rice. The introduction of NiR conferred good growth and regeneration ability of calli compared to the wild-type plants.

Accordingly, there is a need for a method for alleviating the adverse effects associated with nitrate and/or nitrite accumulation in plants. In particular, there is a need for a method for reducing nitrite content in plants, which may, for example, enhance nitrogen assimilation and/or reduce the toxicity of such plants to animals or humans.

SUMMARY OF THE INVENTION

In one aspect, the present invention provides a method for producing a transgenic plant, comprising introducing into an unmodified plant an exogenous gene encoding a nitrite reductase, wherein expression of the nitrite reductase encoded by the exogenous gene reduces nitrite content in the transgenic plant relative to the unmodified plant.

In a further aspect, the present invention provides a transgenic plant comprising an exogenous gene encoding a nitrite reductase, wherein nitrite content in the plant is reduced compared to an unmodified plant.

In a further aspect, the present invention provides use of an exogenous nucleic acid sequence encoding a nitrite reductase for reducing nitrite content in a plant by transformation of the plant with the exogenous nucleic acid sequence.

In a further aspect, the present invention provides a chimaeric gene comprising (a) a nucleic acid sequence encoding a nitrite reductase, and (b) a promoter sequence capable of directing expression of the nitrite reductase in a plant comprising the chimaeric gene, excluding: (i) a chimaeric gene comprising a nucleic acid sequence encoding a nitrite reductase derived from *Nicotiana tabacum* or *Spinacia oleracea* and a cauliflower mosaic virus 35S promoter, and (ii) a chimaeric gene comprising a nucleic acid sequence encoding a nitrite reductase derived from *Oryza sativa*.

In a further aspect, the present invention provides a chimaeric gene comprising (a) a nucleic acid sequence encoding a nitrite reductase, and (b) a promoter sequence capable of directing expression of the nitrite reductase in a plant comprising the chimaeric gene, excluding a chimaeric gene comprising a nucleic acid sequence encoding a nitrite reductase derived from *Nicotiana tabacum, Oryza sativa* or *Spinacia oleracea*.

In a further aspect, the present invention provides a chimaeric gene comprising: (a) a nucleic acid sequence as defined in SEQ ID NO:2 encoding a nitrite reductase, or a fragment thereof encoding a functional nitrite reductase, or a variant thereof encoding a functional nitrite reductase having at least 90% amino acid sequence identity to a polypeptide as defined SEQ ID NO:3; and (b) a promoter sequence capable of directing expression of the nitrite reductase in a plant comprising the chimaeric gene.

In a further aspect, the present invention provides a plant transformation vector comprising a chimaeric gene as defined above.

In a further aspect, the present invention provides a plant or plant cell comprising a transformation vector as defined above.

In a further aspect, the present invention provides a plant cell comprising an exogenous gene encoding a nitrite reductase, wherein nitrite content in the plant cell is reduced compared to an unmodified plant cell.

By "unmodified plant" it is intended to refer to a plant before transformation with the exogenous gene. In other words, "unmodified" refers to any plant from which the transgenic plant is subsequently created by transformation with the exogenous gene. Thus "unmodified" does not limit the nature of the plant in any other way. The plant may be a wild type plant derived from any species or strain, or may be plant which has already been modified by one or more previous genetic modifications, including the introduction of other transgenes or the deletion or inactivation of endogenous genes. In preferred embodiments, the unmodified plant is of the family Solanaceae, more preferably of the subfamily Cestoideae, more preferably of the genus *Nicotiana*, and most preferably the unmodified plant is *Nicotiana tabacum*.

A transgenic plant is generated by introduction of an exogenous gene encoding a nitrite reductase into the unmodified plant. By "exogenous gene" it is meant that the gene is transformed into the unmodified plant from an external source. The exogenous gene may have a nucleic acid sequence identical to or different to an endogenous gene encoding nitrite reductase in the unmodified plant. The exogenous gene may, for example, be derived from a genomic DNA or cDNA sequence encoding a nitrite reductase from any species. Typically the exogenous gene is derived from a different source and has a sequence different to the endogenous gene. Alternatively, introduction of an exogenous gene having a sequence identical to the endogenous gene may be used to increase the number of copies of the endogenous gene sequence present in the plant.

In general, unless otherwise specified, when referring to a "plant" it is intended to cover a plant at any stage of development, including single cells and seeds. Thus in particular embodiments, the present invention provides a plant cell, e.g. an isolated plant cell, having one or more characteristics of a "transgenic plant" as defined herein.

It is preferred that the exogenous gene is not identical to an endogenous gene encoding a nitrite reductase in the plant. For instance, the exogenous gene preferably has less than 95% sequence identity with an endogenous gene encoding a nitrite reductase in the unmodified plant. More preferably the exogenous gene has less than 90%, less than 85%, less than 80%, less than 75%, less than 70%, less than 60%, less than 50% or less than 40% sequence identity with the endogenous nitrite reductase gene.

Similarly, it is preferred that the nitrite reductase encoded by the exogenous gene is not identical (at the amino acid/polypeptide level) to a nitrite reductase encoded by an endogenous gene in the plant. For instance, the exogenous gene product preferably has less than 95% sequence identity with an endogenous gene product in the unmodified plant. More preferably the exogenous gene has less than 90%, less than 85%, less than 80%, less than 75%, less than 70%, less than 60%, less than 50% or less than 40% sequence identity with the endogenous nitrite reductase gene.

Preferably the exogenous gene encoding a nitrite reductase is a heterologous gene, which means that the exogenous gene is derived from a species different to the species of the unmodified plant. In one preferred embodiment, the heterologous gene is derived from a donor plant of the genus *Arabidopsis*, more preferably from *Arabidopsis thaliana*.

In further embodiments, the exogenous gene encoding a nitrite reductase may be derived from any other plant species, including but not limited to a species from one of the following genera: *Nicotiana, Oryza, Capsicum, Spinacia* and *Zea*. For example, the exogenous gene may be derived from *Nicotiana tabacum, Oryza sativa, Capsicum annuum, Spinacia oleracea* or *Zea mays*. In other embodiments, the exogenous gene is derived from a plant species other than rice, e.g. other than a plant of the genus *Oryza* or other than a plant of the species *Oryza sativa*. Alternatively, the exogenous gene may be derived from a species other than *Nicotiana tabacum, Oryza sativa* or *Spinacia oleracea*.

The genomic and cDNA sequences of a nitrite reductase from *Arabidopsis thaliana* are defined in SEQ ID NOs 2 and 1 respectively. The genomic sequence comprises four exons and three introns, as well as 5' and 3' non-translated regions. The cDNA sequence SEQ ID NO:1 comprises the four exons at bases 1248-1623, 1820-2175, 2257-2545 and 2623-3362 of SEQ ID NO:2. The coding sequence plus the 3 introns (i.e. the genomic sequence minus the 5' and 3' non-translated regions) thus stretches from bases 1248-3362 of SEQ ID NO:2. The amino acid sequence of nitrite reductase encoded by these sequences is defined in SEQ ID NO:3.

Preferably the exogenous gene comprises a nucleic acid sequence as defined in SEQ ID NO:2, or a fragment thereof encoding a functional nitrite reductase, or a variant thereof encoding a functional nitrite reductase having at least 70%, at least 80%, at least 90%, or at least 95% amino acid sequence identity to a polypeptide as defined in SEQ ID NO:3. In one embodiment, the fragment of the nucleic acid sequence of SEQ ID NO:2 comprises the cDNA sequence of SEQ ID NO:1 (i.e. residues 1248-1623, 1820-2175, 2257-2545 and 2623-3362 of SEQ ID NO:2), or a variant thereof. In another embodiment, the fragment of the nucleic acid sequence of SEQ ID NO:2 comprises the exons and introns, i.e. residues 1248-3362 of SEQ ID NO:2 or a variant thereof.

In further embodiments, the exogenous gene comprises a nucleic acid sequence as defined in any one of SEQ ID NOs:18, 20, 22, 24, 28, 28, 30 or 32 encoding a nitrite reductase, or a fragment thereof encoding a functional nitrite reductase, or a variant thereof encoding a functional nitrite reductase having at least 70%, 80%, 90%, or 95% amino acid sequence identity to a polypeptide as defined in any one of SEQ ID NOs: 19, 21, 23, 25, 27, 29, 31 or 33. Variant nucleic acid sequences encoding a functional nitrite reductase may alternatively have at least 50%, at least 60%, at least 70%, at least 80% or at least 90% nucleotide sequence identity to one or more of SEQ ID NOs:1, 2, 18, 20, 22, 24, 28, 28, 30 or 32. Variants and fragments of these nucleic acid sequences include genomic DNA sequences (e.g. comprising a full length gene locus including 5' and/or 3' non-translated regions), DNA sequences comprising a coding sequence and introns (e.g. excluding 5' and/or 3' non-translated regions), and cDNA sequences associated with the specified SEQ ID NOs.

In one embodiment, the exogenous gene comprises one or more introns, which may be the introns found in the genomic sequence from which the exogenous gene is derived. The inclusion of introns in the exogenous gene may improve the stability of RNA transcribed therefrom in the transgenic plant, thereby enhancing expression levels of the nitrite reductase. The excision of introns involves a complex of proteins around the RNA, which may protect the RNA from degradation by enzymes which recognise it as "foreign".

The exogenous gene may be introduced into the modified plant by any suitable transformation technique, provided that this leads to expression of the nitrite reductase encoded by the exogenous gene in the transgenic plant. Typically the exogenous gene is a chimaeric gene comprising a nitrite reductase coding sequence fused to a promoter sequence derived from a different gene. Such a chimaeric gene may be cloned into any construct suitable for transforming plants. Preferably the exogenous gene encoding the nitrite reductase is associated with a promoter sequence capable of directing constitutive expression of the exogenous gene in the plant. For instance, in one embodiment the promoter sequence is a constitutive promoter derived from Carnation Etched Ring Virus. The promoter sequence may direct expression of the nitrite reductase encoded by the exogenous gene in any one or more than one tissue of the plant. Preferably the nitrite reductase is expressed in the transgenic plant under control of the promoter at least in the leaves of the plant. In some embodiments, the exogenous gene encodes a chloroplast nitrite reductase, which may, for example be transported to the chloroplast compartment by means of an N-terminal targeting sequence (transit peptide).

In embodiments of the invention, nitrite content of the transgenic plant is reduced relative to an unmodified plant, that is compared to a plant before transformation with the exogenous gene. Since any reduction in nitrite content is desirable, the level of nitrite in the transgenic plant is not particularly limiting provided that it is detectably lower than that of the unmodified plant. Preferably nitrite content is reduced by at least 5%, at least 10%, at least 15%, at least 20%, at least 25%, at least 30%, at least 40%, at least 50% or at least 60% relative to an unmodified plant, with greater reductions being more preferred. Nitrite content may be measured by any suitable technique, for example as described below.

Nitrite content may be reduced in one or more tissues of the plant, for instance in a tissue in which the nitrite reductase encoded by the exogenous gene is expressed. In other tissues, it is possible that nitrite content may not be detectably lower in the transgenic plants compared to the unmodified plants. Thus in one embodiment, nitrite content may, for example, be reduced in the leaves of a transgenic plant compared to an unmodified plant, whereas the level of nitrite in roots of the transgenic plant is not lower than in unmodified plants.

In embodiments of the present invention, the introduction of the exogenous gene into an unmodified plant generates a primary transgenic plant, i.e. a $T_0$ plant produced by direct transformation with the exogenous gene. A secondary transgenic plant (i.e. a $T_1$ plant) may be produced by propagation of the primary transgenic plant, for instance by sexual or asexual reproduction thereof. Preferably the secondary transgenic plant is produced by selfing the primary transgenic plant, i.e. by self-fertilization or self-pollination. In this way, it is possible to generate secondary transgenic plants which are homozygous for the exogenous gene encoding the nitrite reductase. It is expected that 25% of secondary transgenic plants generated by selfing a primary transgenic plant will be homozygous for the exogenous gene.

The present method preferably involves generating a plurality of transgenic plants by independent transformation of a plurality of unmodified plants with the exogenous gene.

In other words, the method may be repeated on multiple individual plants to produce a series of transgenic plants derived from individual transformation events. Plant lines derived from each of these transgenic plants may differ in their properties, including the extent to which nitrite content is reduced. Thus in some embodiments, the method involves screening the transgenic plants produced by the method (either primary, secondary or subsequent generation plants) and selecting those plants having desirable properties (for example a reduction in nitrite content) for further propagation.

Preferably a primary transgenic plant generated by introduction of the exogenous gene contains a single copy of the exogenous gene. The method preferably involves detecting the copy number of the exogenous gene in the primary transgenic plant, for instance before selecting primary transgenic plants having a single copy for propagation.

In another embodiment, the method further comprises determining nitrite content of each of a plurality of transgenic plants generated by independent transformation events. Nitrite content may be determined in the primary, secondary or subsequent generation transgenic plants. The method preferably further comprises selecting one or more transgenic plants having reduced nitrite content relative to an unmodified plant, and propagating the transgenic plants having reduced nitrite content.

In another embodiment, the method comprises producing a plant, cell, or tissue thereof having reduced nitrite content through introducing a mutation into an endogenous nitrite reductase polynucleotide of the plant, cell, or tissue thereof; and detecting the mutation using a method of Targeting Induced Local Lesions In Genomics (TILLING), wherein the mutation results in an overexpression of a nitrite reductase polypeptide.

In another embodiment, the mutation is introduced by a chemical mutagen that may be ethylmethanesulfonate (EMS) or ethylnitrosourea (ENU). In another embodiment, the plant, cell, or tissue thereof is selected for by selecting plants that exhibit a reduced nitrite content relative to an unmodified *Nicotiana tabacum* plant, cell, or tissue thereof.

In another embodiment, a plant, cell, or tissue thereof has reduced nitrite content relative to an unmodified control plant, cell, or tissue thereof; wherein the plant, cell, or tissue thereof has one or more artificially induced point mutations in an endogenous nitrite reductase polynucleotide. In another embodiment, the plant, cell, or tissue thereof exhibits at least a 10% decrease in nitrite content, relative to an unmodified control plant, cell, or tissue thereof.

BRIEF DESCRIPTION OF THE FIGURES

The invention will now be described by way of example only with reference to the following specific embodiments and figures, in which:

FIG. 1 shows an agarose gel image of PCR product of *Arabidopsis* NiR. PCR product was loaded onto a 1% (w/v) agarose/TBE gel. The predicted size of the amplicon was 2.1 Kbp. λ=λ Pst1 marker, A=AtNiR PCR product.

FIG. 2 shows an agarose gel image of SacI digested fragments from pKSAtNiR. Digest was loaded onto a 1% (w/v) agarose/TBE gel. The predicted size of the fragments were 2.1 Kbp, 2.8 Kbp λ=λ Pst1 marker, P=pKSAtNiR.

M=SeeBlue® marker, T=Tobacco WT leaf protein, At=*Arabidopsis* leaf protein, 1-24=individuals screened.

Figure 10:
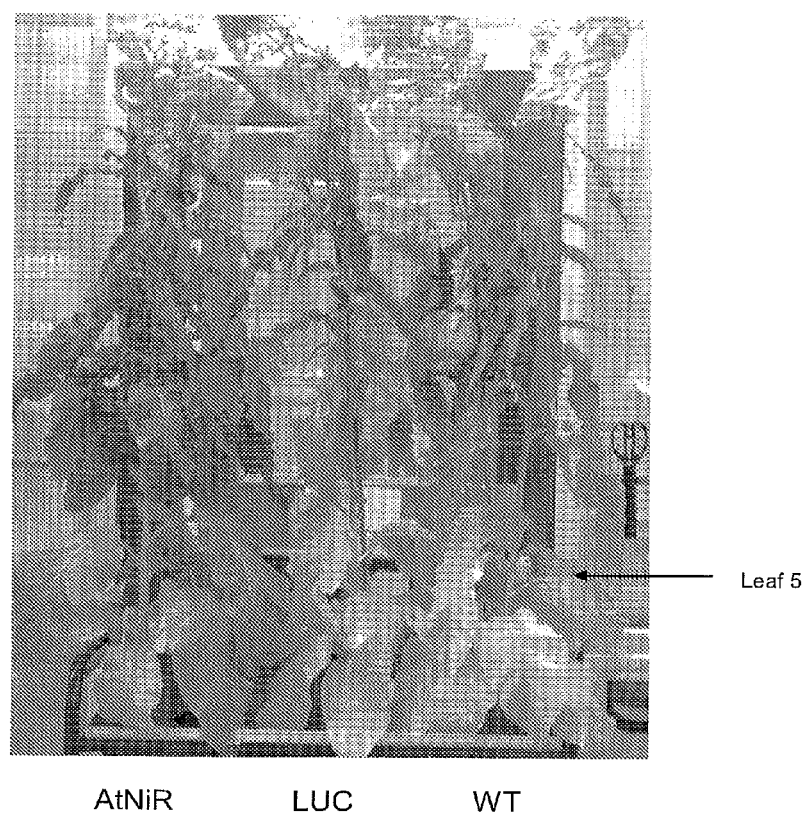

FIG. 10 shows greenhouse tobacco plants at flowering. Two plants from each line are show in the picture. AtNiR=pBNPAtNiR lines 2 and 14, LUC=pBNPLUC=lines 3 and 11, WT=Wildtype.

Figure 11:
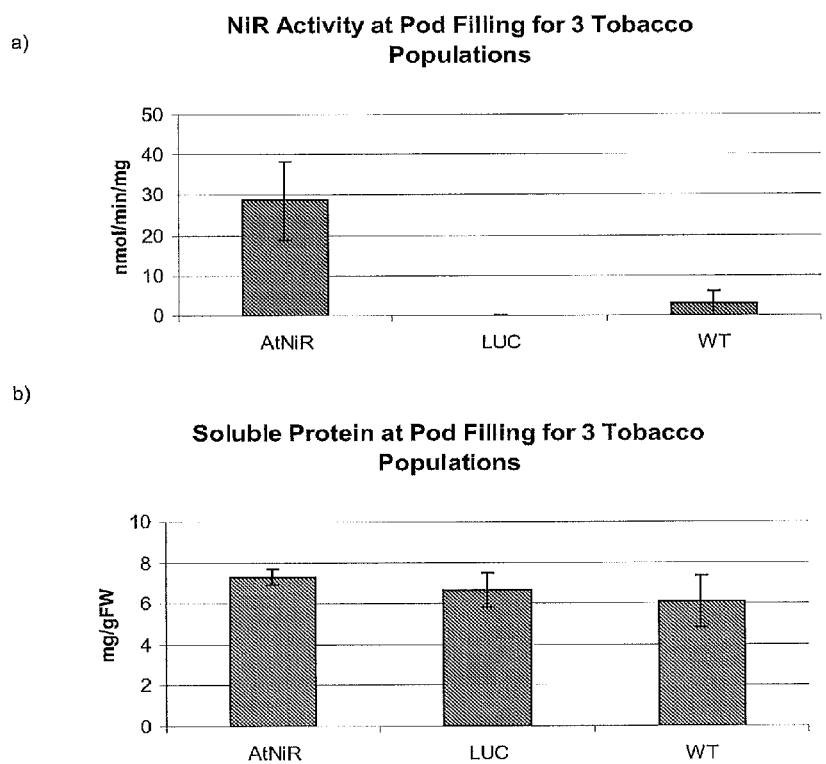

FIG. 11 shows a comparison of a) soluble protein and b) NiR activity between AtNiR, LUC and WT lines at the pod filling stage.

Figure 12:
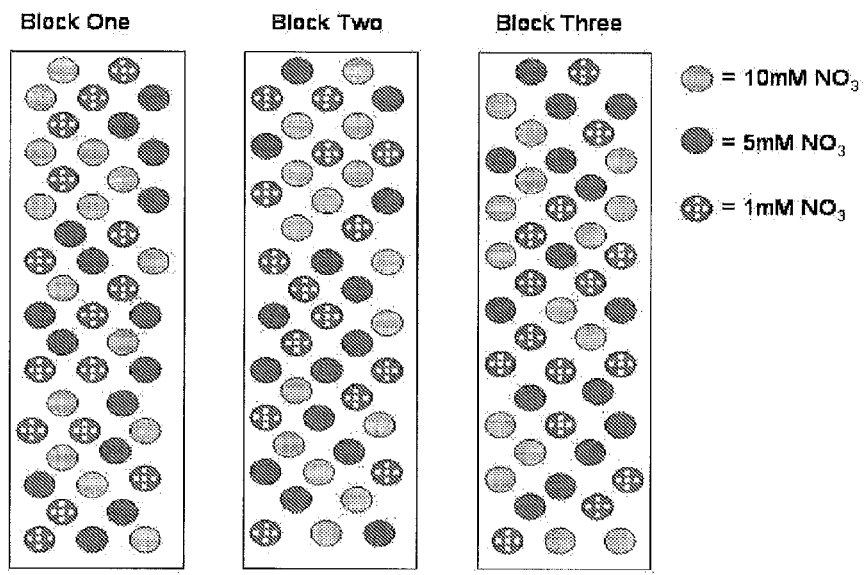

FIG. 12 shows a schematic of randomised block design for nitrate feeding trial.

Figure 13:
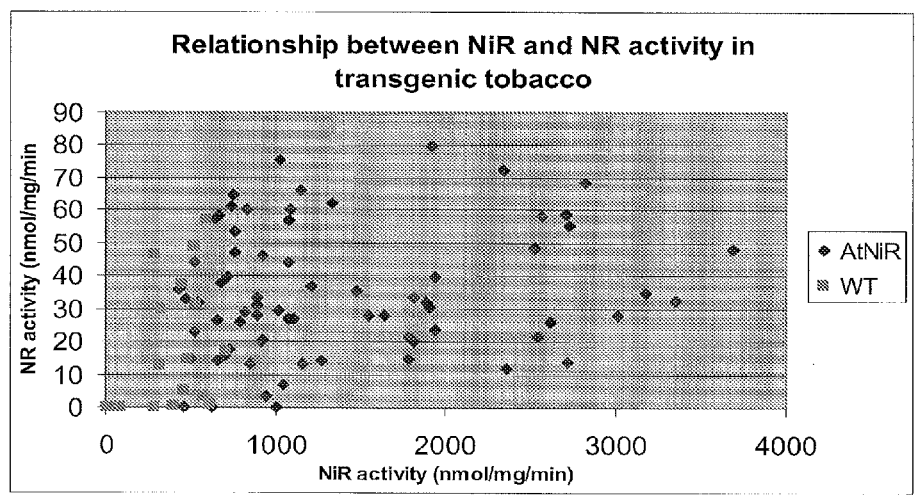

FIG. 13 shows a comparison of AtNiR and WT lines (upper and lower leaves) and the relationship between NiR and NR activity on different nitrate levels. The units used are nmol nitrite per mg protein per minute.

Figure 14:
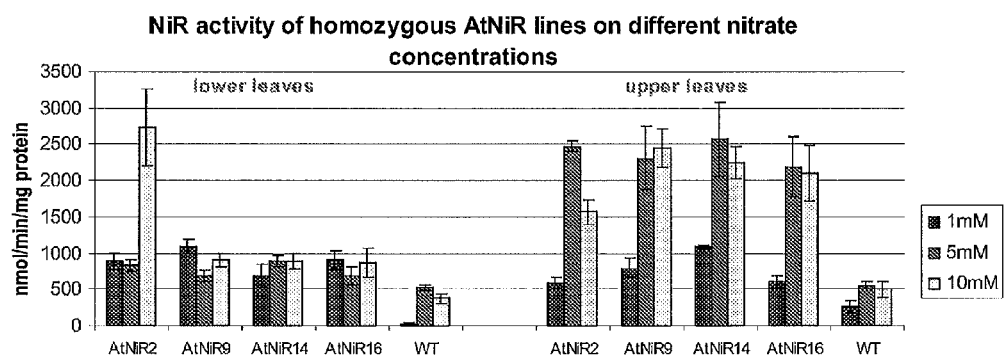
Figure 14:
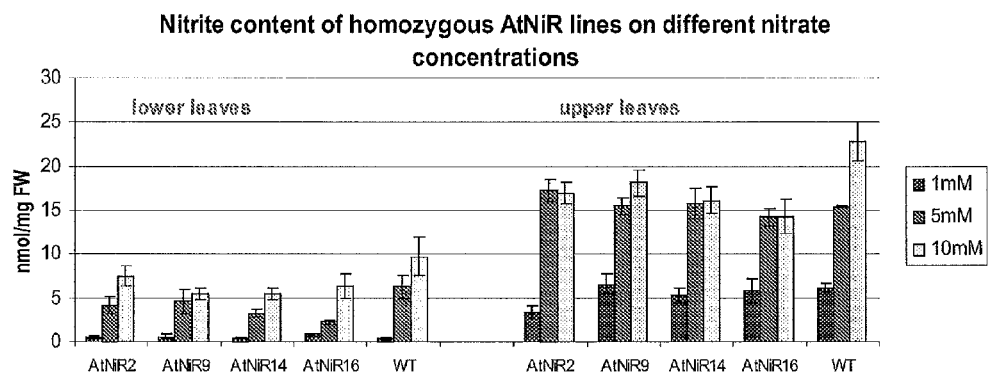

FIG. 14 shows a comparison of source and sink leaves from WT and transgenic AtNiR tobacco grown on different nitrate concentrations and analysed for a) NiR enzyme activities b) nitrite content.

Figure 15:
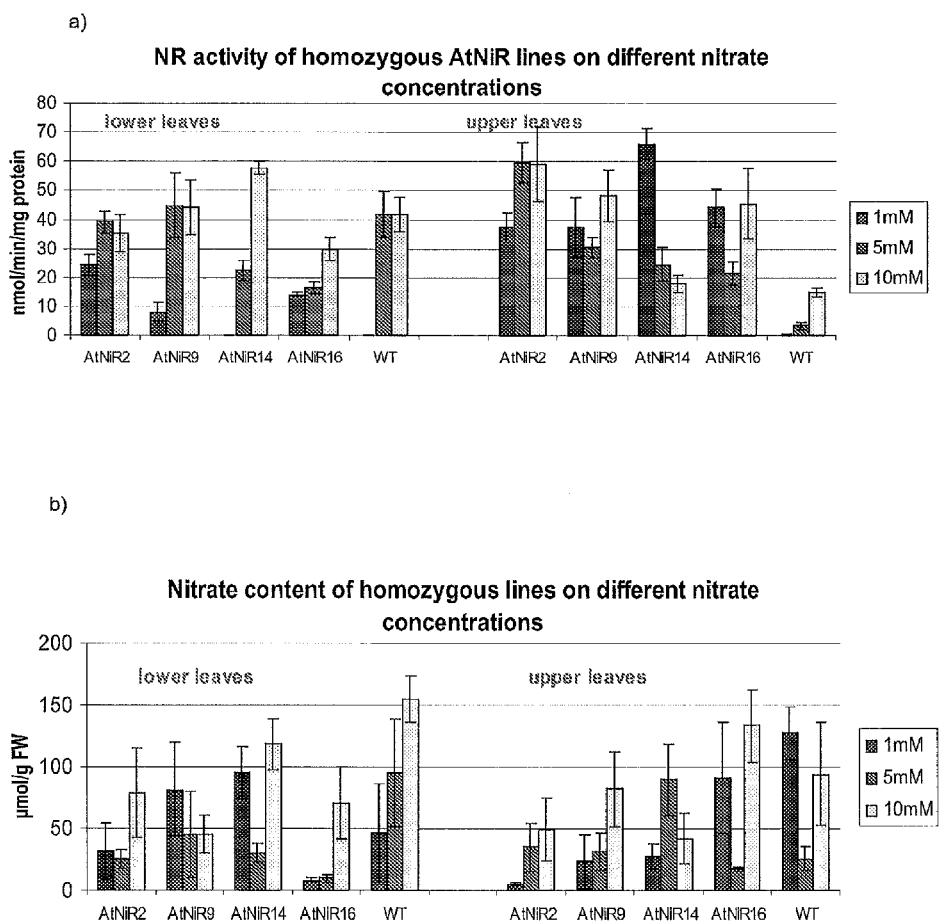

FIG. 15 shows a comparison of source and sink leaves from WT and transgenic AtNiR tobacco grown on different nitrate concentrations and analysed for a) NR enzyme activities b) nitrate content.

Figure 16:
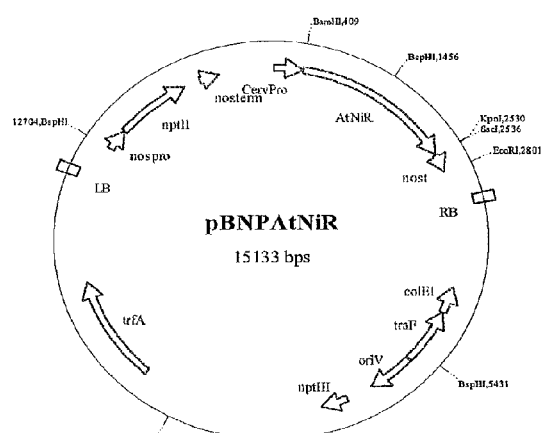
Figure 16:
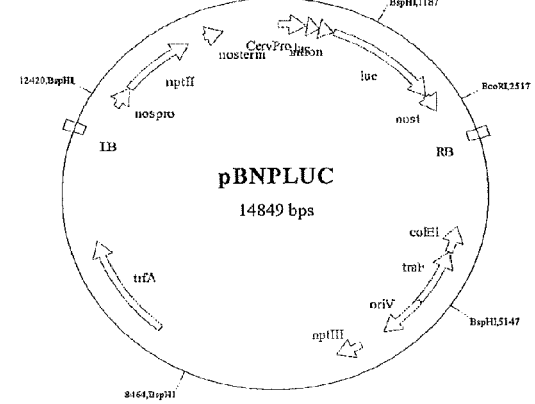
Figure 16:
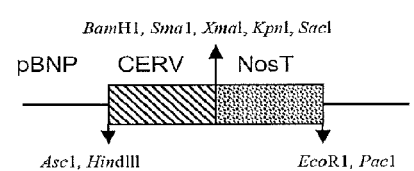

FIG. 16 shows plasmid maps of a) pBNPAtNiR (binary acceptor vector, pBNPCRVT containing the genomic *A. thaliana* nitrite reductase sequence (NiR)); and b) pBNPLUC (binary acceptor vector pBNPCRVT containing luciferase sequence) and c) pBNPCRVT acceptor vector and restriction sites used for cloning events.

FIG. 17 shows the cDNA (SEQ ID NO:1, chloroplast targeting sequence underlined) and amino acid (SEQ ID NO:3) sequences of nitrite reductase from *Arabidopsis thaliana*.

FIGS. 18 and 19 show the genomic DNA sequence of nitrite reductase from *Arabidopsis thaliana*.

FIG. 20 shows the cDNA (SEQ ID NO:18) and amino acid (SEQ ID NO:19) sequences of nitrite reductase from *Capsicum annuum*.

FIG. 21 shows nucleotide (SEQ ID NO:20) and amino acid (SEQ ID NO:21) sequences of nitrite reductase from *Oryza sativa*.

FIG. 22 shows nucleotide (SEQ ID NO:22) and amino acid (SEQ ID NO:23) sequences of nitrite reductase from *Spinacia oleracea*.

FIG. 23 shows nucleotide (SEQ ID NO:24) and amino acid (SEQ ID NO:25) sequences of nitrite reductase 1 from *Nicotiana tabacum*.

FIG. 24 shows nucleotide (SEQ ID NO:26) and amino acid (SEQ ID NO:27) sequences of nitrite reductase 2 from *Nicotiana tabacum*.

FIG. 25 shows nucleotide (SEQ ID NO:28) and amino acid (SEQ ID NO:29) sequences of nitrite reductase 3 from *Nicotiana tabacum*.

FIG. 26 shows nucleotide (SEQ ID NO:30) and amino acid (SEQ ID NO:31) sequences of nitrite reductase 4 from *Nicotiana tabacum*.

FIG. 27 shows nucleotide (SEQ ID NO:32) and amino acid (SEQ ID NO:33) sequences of nitrite reductase from *Zea mays*.

DETAILED DESCRIPTION OF THE INVENTION

Embodiments of the present invention involve transformation of plants with an exogenous gene encoding a nitrite reductase. A plant DNA sequence encoding a nitrite reductase may, for example, be recovered from the cells of a natural host, or it may be synthesized directly in vitro. Extraction from the natural host enables the isolation de novo of novel sequences, whereas in vitro DNA synthesis generally requires pre-existing sequence information. Direct chemical in vitro synthesis can be achieved by sequential manual synthesis or by automated procedures. DNA sequences may also be constructed by standard techniques of annealing and ligating fragments, or by other methods known in the art. Examples of such cloning procedures are given in Sambrook et al. (1989).

A DNA sequence encoding a nitrite reductase may be isolated by direct cloning of segments of plant genomic DNA. Suitable segments of genomic DNA may be obtained by fragmentation using restriction endonucleases, sonication, physical shearing, or other methods known in the art. Sequences of nitrite reductases in various plants are known in the art, and additional genes may be identified by sequence or structural homology to known nitrite reductases. Thus a DNA sequence encoding a nitrite reductase may be obtained by identification of a sequence which is known to be expressed in a different organism, and then isolating the homologous coding sequence from an organism of choice. A coding sequence may be obtained by the isolation of messenger RNA (mRNA or polyA+ RNA) from plant tissue or isolation of a protein and performing "back-translation" of its sequence. The tissue used for RNA isolation is selected on the basis that suitable gene coding sequences are believed to be expressed in that tissue at optimal levels for isolation.

Various methods for isolating mRNA from plant tissue are well known to those skilled in the art, including for example using an oligo-dT oligonucleotide immobilised on an inert matrix. The isolated mRNA may be used to produce its complementary DNA sequence (cDNA) by use of the enzyme reverse transcriptase (RT) or other enzymes having reverse trancriptase activity. Isolation of an individual cDNA sequence from a pool of cDNAs may be achieved by cloning into bacterial or viral vectors, or by employing the polymerase chain reaction (PCR) with selected oligonucleotide primers. The production and isolation of a specific cDNA from mRNA may be achieved by a combination of the reverse transcription and PCR steps in a process known as RT-PCR.

Various methods may be employed to improve the efficiency of isolation of the desired sequence through enrichment or selection methods including the isolation and comparison of mRNA (or the resulting single or double-stranded cDNA) from more than one source in order to identify those sequences expressed predominantly in the tissue of choice. Numerous methods of differential screening, hybridisation, or cloning are known to those skilled in the art including cDNA-AFLP, cascade hybridisation, and commercial kits for selective or differential cloning.

The identification of the cloned segment as a nitrite reductase may, for example, be confirmed by assessing functionality, for example by linking the cloned segment with a promoter sequence and introducing the chimaeric construct into a host cell or cell-free system wherein nitrite reductase activity can be evaluated.

The selected cDNA may then be used to evaluate the genomic features of its gene of origin, by use as a hybridisation probe in a Southern blot of plant genomic DNA to reveal the complexity of the genome with respect to that sequence. Alternatively, sequence information from the cDNA may be used to devise oligonucleotides and these can be used in the same way as hybridisation probes; for PCR primers to produce hybridisation probes, or for PCR primers to be used in direct genome analysis.

Similarly the selected cDNA may be used to evaluate the expression profile of its gene of origin, by use as a hybridisation probe in a Northern blot of RNA extracted from various plant tissues, or from a developmental or temporal series. Again sequence information from the cDNA may be used to devise oligonucleotides which can be used as hybridisation probes, to produce hybridisation probes, or directly for RT-PCR. The selected cDNA, or derived oligonucleotides, may then be used as a hybridisation probe to challenge a library of cloned genomic DNA fragments and identify overlapping DNA sequences.

In embodiments of the present invention, the exogenous gene may be coupled to a promoter which directs expression of the nitrite reductase in the transgenic plant. The term "promoter" may be used to refer to a region of DNA sequence located upstream of (i.e. 5' to) the gene coding sequence which is recognised by and bound by RNA polymerase in order for transcription to be initiated.

There are, broadly speaking, four types of promoters found in plant tissues; constitutive, tissue-specific, developmentally-regulated, and inducible/repressible, although it should be understood that these types are not necessarily mutually exclusive.

A constitutive promoter directs the expression of a gene throughout the various parts of a plant continuously during plant development, although the gene may not be expressed at the same level in all cell types. Examples of known constitutive promoters include those associated with the cauliflower mosaic virus 35S transcript (Odell et al, 1985), the rice actin 1 gene (Zhang et al, 1991) and the maize ubiquitin 1 gene (Cornejo et al, 1993). Constitutive promoters such as the Carnation Etched Ring Virus (CERV) promoter (Hull et al., 1986) are particularly preferred in the present invention.

A tissue-specific promoter is one which directs the expression of a gene in one (or a few) parts of a plant, usually throughout the lifetime of those plant parts. The category of tissue-specific promoter commonly also includes promoters whose specificity is not absolute, i.e. they may also direct expression at a lower level in tissues other than the preferred tissue. Examples of tissue-specific promoters known in the art include those associated with the patatin gene expressed in potato tuber and the high molecular weight glutenin gene expressed in wheat, barley or maize endosperm.

A developmentally-regulated promoter directs a change in the expression of a gene in one or more parts of a plant at a specific time during plant development. The gene may be expressed in that plant part at other times at a different (usually lower) level, and may also be expressed in other plant parts.

An inducible promoter is capable of directing the expression of a gene in response to an inducer. In the absence of the inducer the gene will not be expressed. The inducer may act directly upon the promoter sequence, or may act by counteracting the effect of a repressor molecule. The inducer may be a chemical agent such as a metabolite, a protein, a growth regulator, or a toxic element, a physiological stress such as heat, wounding, or osmotic pressure, or an indirect consequence of the action of a pathogen or pest. A developmentally-regulated promoter might be described as a specific type of inducible promoter responding to an endogenous inducer produced by the plant or to an environmental stimulus at a particular point in the life cycle of the plant. Examples of known inducible promoters include those associated with wound response, such as described by Warner et al (1993), temperature response as disclosed by Benfey & Chua (1989), and chemically induced, as described by Gatz (1995).

In certain embodiments of the present invention, chimaeric genes encoding a nitrite reductase may be transformed into plant cells leading to controlled expression of the nitrite reductase under the direction of a promoter. The promoters may be obtained from different sources including animals, plants, fungi, bacteria, and viruses, and different promoters may work with different efficiencies in different tissues. Promoters may also be constructed synthetically.

In embodiments of the present invention, an exogenous gene encoding a nitrite reductase is used which has a restricted degree of sequence homology or sequence identity with an endogenous gene encoding nitrite reductase. Sequences having a required degree of sequence identity with disclosed sequences such as SEQ ID NO:1 are also defined herein. Homology may be determined on the basis of percentage identity between two DNA (or polypeptide) sequences. In general the two sequences to be compared are aligned to give a maximum correlation between the sequences. The alignment of the two sequences is examined and the number of positions giving an exact nucleotide (or amino acid) correspondence between the two sequences determined, divided by the total length of the alignment multiplied by 100 to give a percentage identity figure. This percentage identity figure may be determined over the whole length of the sequences to be compared, which is particularly suitable for sequences of the same or very similar lengths and which are highly homologous, or over shorter defined lengths, which is more suitable for sequences of unequal length or which have a lower level of homology. For example, a degree of sequence identity to a nucleotide or amino acid sequence as defined herein may be determined over at least 15, at least 30, at least 50, at least 100, at least 200, at least 500 or at least 1000 residues.

Methods for comparing the identity of two or more sequences are well known in the art. Thus for instance, programs available in the Wisconsin Sequence Analysis Package, version 9.1 (Devereux J. et al, 1984) (available from Genetics Computer Group, Madison, Wis., USA), for example the programs BESTFIT and GAP, may be used to determine the percentage identity between two polynucleotides and the percentage identity between two polypeptide sequences. BESTFIT uses the "local homology" algorithm of Smith and Waterman (1981) and finds the best single region of similarity between two sequences. BESTFIT is more suited to comparing two polynucleotide or two polypeptide sequences which are dissimilar in length, the program assuming that the shorter sequence represents a portion of the longer. In comparison, GAP aligns two sequences finding a "maximum similarity" according to the algorithm of Needleman and Wunsch (1970). GAP is more suited to comparing sequences which are approximately the same length and an alignment is expected over the entire length. Preferably the parameters "Gap Weight" and "Length Weight" used in each program are 50 and 3 for polynucleotide sequences and 12 and 4 for polypeptide sequences, respectively. Preferably, percentage identities and similarities are determined when the two sequences being compared are optimally aligned.

Other programs for determining identity and/or similarity between sequences are also known in the art, for instance the BLAST family of programs (Karlin & Altschul, 1990, *Proc. Natl. Acad. Sci. USA* 87:2264-2268, modified as in Karlin & Altschul, 1993, *Proc. Natl. Acad. Sci. USA* 90:5873-5877, available from the National Center for Biotechnology Information (NCBI), Bethesda, Md., USA and accessible through the home page of the NCBI at www[DOT]ncbi.nlm.nih.gov). These programs exemplify a preferred, non-limiting example of a mathematical algorithm utilized for the comparison of two sequences. Such an algorithm is incorporated into the NBLAST and XBLAST programs of Altschul, et al., 1997, *J. Mol. Biol.* 215:403-410. BLAST nucleotide searches can be performed with the NBLAST program to obtain nucleotide sequences homologous to a nucleic acid molecule of the invention. BLAST protein searches can be performed with the XBLAST program, to obtain amino acid sequences homologous to a protein molecule of the invention. To obtain gapped alignments for comparison purposes, Gapped BLAST can be utilized as described in Altschul et al., 1997, *Nucleic Acids Res.* 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See http://www[DOT]ncbi.nlm.nih.gov. Another preferred non-limiting example of a mathematical algorithm utilized for the comparison of sequences is the algorithm of Myers and Miller, 1988, *CABIOS* 4:11-17. Such an algorithm is incorporated into the ALIGN program (version 2.0) which is part of the GCG sequence alignment software package.

Another non-limiting example of a program for determining identity and/or similarity between sequences known in the art is FASTA (Pearson W. R. and Lipman D. J., Proc. Nat. Acac. Sci., USA, 85:2444-2448, 1988, available as part of the Wisconsin Sequence Analysis Package). Preferably the BLOSUM62 amino acid substitution matrix (Henikoff S. and Henikoff J. G., Proc. Nat. Acad. Sci., USA, 89:10915-10919, 1992) is used in polypeptide sequence comparisons including where nucleotide sequences are first translated into amino acid sequences before comparison.

The percent identity between two sequences can be determined using techniques similar to those described above, with or without allowing gaps. In calculating percent identity, typically exact matches are counted.

Preferably the program BESTFIT is used to determine the % identity of a query polynucleotide or a polypeptide sequence with respect to a polynucleotide or a polypeptide sequence of the present invention, the query and the reference sequence being optimally aligned and the parameters of the program set at the default value.

As used herein, the term "homologue" means an entity having a certain homology with the subject amino acid sequences and the subject nucleotide sequences. Here, the term "homology" can be equated with "identity". Although homology can also be considered in terms of similarity (i.e. amino acid residues having similar chemical properties/functions), in the context of the present invention it is preferred to express homology in terms of sequence identity.

The term "nucleotide sequence" as used herein is synonymous with "nucleic acid sequence" and refers to an oligonucleotide sequence or polynucleotide sequence, and variants, homologues, fragments and derivatives thereof (such as portions thereof). The nucleotide sequence may be of genomic or synthetic or recombinant origin, which may be double-stranded or single-stranded whether representing the sense or anti-sense strand. The term "nucleotide sequence" or "nucleic acid" in relation to the present invention includes genomic DNA, cDNA, synthetic DNA, and RNA.

Due to degeneracy in the genetic code, nucleotide sequences may be readily produced in which the triplet codon usage, for some or all of the amino acids encoded by the original nucleotide sequence, has been changed thereby producing a nucleotide sequence with low homology to the original nucleotide sequence but which encodes the same, or a variant, amino acid sequence as encoded by the original nucleotide sequence. For example, for most amino acids the degeneracy of the genetic code is at the third position in the triplet codon (wobble position) (for reference see Stryer, Lubert, Biochemistry, Third Edition, Freeman Press, ISBN 0-7167-1920-7) therefore, a nucleotide sequence in which all triplet codons have been "wobbled" in the third position would be about 66% identical to the original nucleotide sequence however, the amended nucleotide sequence would encode for the same, or a variant, primary amino acid sequence as the original nucleotide sequence.

Therefore, the present invention further relates to any nucleotide sequence that has alternative triplet codon usage for at least one amino acid encoding triplet codon, but which encodes the same, or a variant, polypeptide sequence as the polypeptide sequence encoded by the original nucleotide sequence.

Furthermore, specific organisms typically have a bias as to which triplet codons are used to encode amino acids. Preferred codon usage tables are widely available, and can be used to prepare codon optimised genes. Such codon optimisation techniques are routinely used to optimise expression of transgenes in a heterologous host.

Typically, a nucleotide sequence encoding a nitrite reductase as used in the present invention is prepared using recombinant DNA techniques. However, in an alternative embodiment of the invention, the nucleotide sequence could be synthesised, in whole or in part, using chemical methods well known in the art (see Caruthers M H et al (1980) Nuc Acids Res Symp Ser 215-23 and Horn T et al (1980) Nuc Acids Res Symp Ser 225-232).

Sequences encoding known nitrite reductases may, for example, be modified in order to provide alternative exogenous genes for use in the present invention. For example, mutations may be introduced using synthetic oligonucleotides. These oligonucleotides contain nucleotide sequences flanking the desired mutation sites.

A suitable method is disclosed in Morinaga et al (Biotechnology (1984) 2, p 646-649). Another method of introducing mutations into nucleotide sequences is described in Nelson and Long (Analytical Biochemistry (1989), 180, p 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech. EP 0 583 265 refers to methods of optimising PCR based mutagenesis, which can also be combined with the use of mutagenic DNA analogues such as those described in EP 0 866 796.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence. Suitable methods for performing 'shuffling' can be found in EP0 752 008, EP1 138 763, EP1 103 606. Shuffling can also be combined with other forms of DNA mutagenesis as described in U.S. Pat. No. 6,180,406 and WO 01/34835.

Thus, it is possible to produce numerous site directed or random mutations into a nucleotide sequence, either in vivo or in vitro, and to subsequently screen for improved functionality of the encoded nitrite reductase by various means. Using in silico and exo mediated recombination methods (see WO 00/58517, U.S. Pat. No. 6,344,328, U.S. Pat. No. 6,361,974), for example, molecular evolution can be performed where the variant produced retains very low homology to known proteins. Such variants thereby obtained may have significant structural analogy to known proteins, but have very low amino acid sequence homology.

In addition, mutations or natural variants of a polynucleotide sequence can be recombined with either the wild type or other mutations or natural variants to produce new variants. Such new variants can also be screened for improved functionality of the encoded polypeptide.

Exogenous genes may be introduced into plants according to the present invention by means of suitable plant transformation vectors. A plant transformation vector may comprise an expression cassettes comprising 5'-3' in the direction of transcription, a promoter sequence, a nitrite reductase coding sequence and, optionally a 3' untranslated, terminator sequence including a stop signal for RNA polymerase and a polyadenylation signal for polyadenylase. The promoter sequence may be present in one or more copies, and such copies may be identical or variants of a promoter sequence as described above. The terminator sequence may be obtained from plant, bacterial or viral genes. Suitable terminator sequences are the pea rbcS E9 terminator sequence, the nos terminator sequence derived from the nopaline synthase gene of *Agrobacterium tumefaciens* and the 35S terminator sequence from cauliflower mosaic virus, for example. A person skilled in the art will be readily aware of other suitable terminator sequences.

The expression cassette may also comprise a gene expression enhancing mechanism to increase the strength of the promoter. An example of such an enhancer element is that derived from a portion of the promoter of the pea plastocyanin gene, and which is the subject of International Patent Application No. WO 97/20056. These regulatory regions may be derived from the same gene as the promoter DNA sequence or may be derived from different genes, from *Nicotiana tabacum* or other organisms, for example from a plant of the family Solanaceae, or from the subfamily Cestroideae. All of the regulatory regions should be capable of operating in cells of the tissue to be transformed.

The promoter DNA sequence may be derived from the same gene as the nitrite reductase coding sequence used in the present invention or may be derived from a different gene, from *Nicotiana tabacum*, or another organism, for example from a plant of the family Solanaceae, or from the subfamily Cestroideae. When referring to a "chimaeric gene", it is meant that the nucleic acid sequence encoding a nitrite reductase is derived from a different origin (e.g. from a different gene, or from a different species) to the promoter sequence which directs its expression.

The expression cassette may be incorporated into a basic plant transformation vector, such as pBIN 19 Plus, pBI 101, or other suitable plant transformation vectors known in the art. In addition to the expression cassette, the plant transformation vector will contain such sequences as are necessary for the transformation process. These may include the *Agrobacterium* vir genes, one or more T-DNA border sequences, and a selectable marker or other means of identifying transgenic plant cells.

The term "plant transformation vector" means a construct capable of in vivo or in vitro expression. Preferably, the expression vector is incorporated in the genome of the organism. The term "incorporated" preferably covers stable incorporation into the genome.

Techniques for transforming plants are well known within the art and include *Agrobacterium*-mediated transformation, for example. The basic principle in the construction of genetically modified plants is to insert genetic information in the plant genome so as to obtain a stable maintenance of the inserted genetic material. A review of the general techniques may be found in articles by Potrykus (*Annu Rev Plant Physiol Plant Mol Biol* [1991] 42:205-225) and Christou (Agro-Food-Industry Hi-Tech March/April 1994 17-27).

Typically, in *Agrobacterium*-mediated transformation a binary vector carrying a foreign DNA of interest, i.e. a chimaeric gene, is transferred from an appropriate *Agrobacterium* strain to a target plant by the co-cultivation of the *Agrobacterium* with explants from the target plant. Transformed plant tissue is then regenerated on selection media, which selection media comprises a selectable marker and plant growth hormones. An alternative is the floral dip method (Clough & Bent, 1998) whereby floral buds of an intact plant are brought into contact with a suspension of the *Agrobacterium* strain containing the chimeric gene, and following seed set, transformed individuals are germinated and identified by growth on selective media. Direct infection of plant tissues by *Agrobacterium* is a simple technique which has been widely employed and which is described in Butcher D. N. et al., (1980), *Tissue Culture Methods for Plant Pathologists*, eds.: D. S. Ingrams and J. P. Helgeson, 203-208.

Further suitable transformation methods include direct gene transfer into protoplasts using polyethylene glycol or electroporation techniques, particle bombardment, microinjection and the use of silicon carbide fibres for example.

Transforming plants using ballistic transformation, including the silicon carbide whisker technique are taught in Frame B R, Drayton P R, Bagnaall S V, Lewnau C J, Bullock W P, Wilson H M, Dunwell J M, Thompson J A & Wang K (1994). Production of fertile transgenic maize plants by silicon carbide whisker-mediated transformation is taught in *The Plant Journal* 6: 941-948) and viral transformation techniques is taught in for example Meyer P, Heidmann I & Niedenhof I (1992). The use of cassava mosaic virus as a vector system for plants is taught in *Gene* 110: 213-217. Further teachings on plant transformation may be found in EP-A-0449375.

In a further aspect, the present invention relates to a vector system which carries a nucleotide sequence encoding a nitrite reductase and introducing it into the genome of an organism, such as a plant. The vector system may comprise one vector, but it may comprise two vectors. In the case of two vectors, the vector system is normally referred to as a binary vector system. Binary vector systems are described in further detail in Gynheung An et al., (1980), Binary Vectors, *Plant Molecular Biology Manual* A3, 1-19.

One extensively employed system for transformation of plant cells uses the Ti plasmid from *Agrobacterium tumefaciens* or a Ri plasmid from *Agrobacterium rhizogenes* An et al., (1986), *Plant* Physiol. 81, 301-305 and Butcher D. N. et al., (1980), *Tissue Culture Methods for Plant Pathologists*, eds.: D. S. Ingrams and J. P. Helgeson, 203-208. After each introduction method of the desired exogenous gene according to the present invention in the plants, the presence and/or insertion of further DNA sequences may be necessary. If, for example, for the transformation the Ti- or Ri-plasmid of the plant cells is used, at least the right boundary and often however the right and the left boundary of the Ti- and Ri-plasmid T-DNA, as flanking areas of the introduced genes, can be connected. The use of T-DNA for the transformation of plant cells has been intensively studied and is described in EP-A-120516; Hoekema, in: The Binary Plant Vector System Offset-drukkerij Kanters B. B., Alblasserdam, 1985, Chapter V; Fraley, et al., *Crit. Rev. Plant Sci.*, 4:1-46; and An et al., *EMBO J.* (1985) 4:277-284.

Plant cells transformed with an exogenous gene encoding a nitrite reductase may be grown and maintained in accordance with well-known tissue culturing methods such as by culturing the cells in a suitable culture medium supplied with the necessary growth factors such as amino acids, plant hormones, vitamins, etc.

The term "transgenic plant" in relation to the present invention includes any plant that comprises an exogenous gene encoding a nitrite reductase according to the present invention. Preferably the exogenous gene is incorporated in the genome of the plant.

The terms "transgenic plant" and "chimaeric gene" do not cover native nucleotide coding sequences in their natural environment when they are under the control of their native promoter which is also in its natural environment.

In one aspect, a nucleic acid sequence, chimaeric gene, plant transformation vector or plant cell according to the present invention is in an isolated form. The term "isolated" means that the sequence is at least substantially free from at least one other component with which the sequence is naturally associated in nature and as found in nature.

In one aspect, a nucleic acid sequence, chimaeric gene, plant transformation vector or plant cell according to the invention is in a purified form. The term "purified" means in a relatively pure state—e.g. at least about 90% pure, or at least about 95% pure or at least about 98% pure.

The plants which are transformed with an exogenous gene according to the present invention include those of interest to the horticulture industry, the floriculture industry, the forestry industry and/or the agriculture industry. The plant may be a plant which is grown for the purpose of providing cut flowers. The plant may be tomato, cucumber, *Petunia, Dianthus, Picea, Pinus, Eucalyptus, Populus*, a dicotyledonous species such as potato, tobacco, cotton, lettuce, eggplant, melon, squash, pea, canola, soybean, sugar beet or sunflower, or a monocotyledonous species such as wheat, barley, rye, rice, or maize. More preferably the plant is of the family Solanaceae. More preferably the plant is of the subfamily Cestroideae. More preferably the plant is one or more of tomato, potato, aubergine, Petunia or tobacco. More preferably the plant is of the genus *Nicotiana*. Most preferably the plant is *Nicotiana tabacum*. Suitable exogenous genes encoding nitrite reductases may also be obtained from such species.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

The term "variant" as used herein means a protein expressed from a non-endogenous genetic code resulting in one or more amino acid alterations (i.e. amino acid deletions, additions or substitutions) when compared with the natural or wild-type sequence within the mature protein sequence.

The present application utilizes a method of Targeting Induced Local Lesions in Genomics (TILLING®) as a method in molecular biology that allows directed identification of mutations in a specific gene. TILLING® was introduced in 2000, using the model plant *Arabidopsis thaliana*. TILLING® has since been used as a reverse genetics method in other organisms such as zebrafish, corn, wheat, rice, soybean, tomato, lettuce, and other plants.

The method combines a standard and efficient technique of mutagenesis with a chemical mutagen (e.g., Ethyl methanesulfonate (EMS)) with a sensitive DNA screening-technique that identifies single base mutations (also called point mutations) in a target gene. EcoTILLING is a method that uses TILLING® techniques to look for natural mutations in individuals, usually for population genetics analysis (see Comai, et al., 2003 The Plant Journal 37, 778-786; Gilchrist et al. 2006 Mol. Ecol. 15, 1367-1378; Mejlhede et al. 2006 Plant Breeding 125, 461-467; Nieto et al. 2007 BMC Plant Biology 7, 34-42, each of which is incorporated by reference hereby for all purposes). DEcoTILLING is a modification of TILLING® and EcoTILLING which uses an inexpensive method to identify fragments (Garvin et al., 2007, DEcoTILLING: An inexpensive method for SNP discovery that reduces ascertainment bias. Molecular Ecology Notes 7, 735-746).

The TILLING® method relies on the formation of heteroduplexes that are formed when multiple alleles (which could be from a heterozygote or a pool of multiple homozygotes and heterozygotes) are amplified in a PCR, heated, and then slowly cooled. A "bubble" forms at the mismatch of the two DNA strands (the induced mutation in TILLING® or the natural mutation or SNP in EcoTILLING), which is then cleaved by single stranded nucleases. The products are then separated by size on several different platforms.

Several TILLING® centers exists over the world that focus on agriculturally important species: UC Davis (USA), focusing on Rice; Purdue University (USA), focusing on Maize; University of British Columbia (CA), focusing on *Brassica napus*; John Innes Centre (UK), focusing on *Brassica rapa*; Fred Hutchinson Cancer Research, focusing on *Arabidopsis*; Southern Illinois University (USA), focusing on Soybean; John Innes Centre (UK), focusing on Lotus and *Medicago*; and INRA (France), focusing on Pea and Tomato.

More detailed description on methods and compositions on TILLING® can be found in U.S. Pat. No. 5,994,075, US 2004/0053236 A1, WO 2005/055704, and WO 2005/048692, each of which is hereby incorporated by reference for all purposes.

EXAMPLES

The invention will now be described, by way of example only, with reference to the following Examples.

Residual nitrate/nitrite in harvested leaf material can lead to the formation of undesirable compounds such as N-nitrosamines. These have been linked to several cancers in humans, such as digestive tract, liver, lung and kidney (Ellis et al., 1998). The major nitrosating agent is nitrite (Morikawa et al., 2004). In the following examples, the present inventors set out to influence the build up of nitrite in the cell by controlling the activity of NiR. In particular, it is demonstrated herein that in one embodiment, the nitrite content of leaves could be reduced by increasing the activity of chloroplastic nitrite reductase in tobacco.

A suitable candidate gene was chose to be integrated into the tobacco plant genome. The gene had to be coupled to an appropriate promoter/regulatory sequence depending on where and when that gene was required to be expressed in the transgenic plant. To influence nitrate/nitrite accumulation the candidate genes should be a primary nitrogen assimilation gene such as NiR. To decrease the residual nitrate in the leaf, over-expression of the gene provides an increased capacity to assimilate the nitrate and nitrite in the cell.

As discussed above, overexpression of nitrate reductase in plants led to a damaging build-up of nitrite levels. The present inventors hypothesised that the over-expression of NiR may be a more suitable candidate for preventing the deleterious effects of nitrate oversupply, since any potential accumulation of ammonia would be more easily tolerated than that of nitrite.

The introduction of transgenes containing sequences homologous to endogenous genes can result in co-suppression (Crété and Vaucheret, 1999). Therefore in the following preferred embodiments, transgenes were introduced which were not identical or similar at the nucleotide level to endogenous nitrite reductase in tobacco. In this study, a NiR (*A. thaliana thaliana*) gene was isolated and introduced into tobacco plants under the control of a constitutive promoter, Carnation Etched Ring Virus (CERV (Hull et al., 1986)). The resulting transgenic plants have been subjected to detailed physiological, biochemical and molecular analyses.

In plant genetic modification, intact DNA molecules are integrated into the nuclear genome of cells, usually with the aid of *Agrobacterium tumafaciens*. These cells regenerate to form calli which, on the addition of plant hormones, can produce fertile adult plants via established tissue culture procedures (Hansen et al., 1994). *Agrobacterium*-mediated transformation has the ability to integrate large segments of transfer DNA (or T-DNA) into the genome with minimal rearrangement. It generally transfers between one and five copies of the inserted genes and has a high efficiency of transformation (Hansen and Wright, 1999).

Mechanisms operating within the plants defence system which can prevent expression of integrated transgenes include DNA methylation and RNA interference (RNAi). Due to these gene silencing mechanisms, in the following examples a candidate NiR gene was identified which is over-expressed in tobacco without being silenced. In this example, a NiR gene with minimal homology to the endogenous tobacco NiRs was identified.

The number of NiR genes varies among plant species: *A. thaliana, Oryza sativa, Capsicum annuum* and *Spinacia oleracea* have one, there are two in *Zea mays*, whilst tobacco is unique in possessing four. This is due to the tetraploid nature of the tobacco genome, which has evolved from the merging of two ancestral tobacco species, *N. sylvestris* and *N. tomentosiformis*. Homologues of NiR1 and NiR2 genes have been found in *Nicotiana tomentosiformis* and NiR3 and NiR4 in *Nicotiana sylvestris* (Kronenberger et al., 1993).

There are full length NiR cDNA sequences for *N tabacum, A. thaliana, S. oleracea, 0. to sativa* and *C. annuum* available in GenBank. Only one partial cDNA sequence is available for *Z. mays*. The eight NiR protein sequences all have similar ORF lengths, molecular masses and isoelectric points, but there is a significant difference of charge at pH7. The sequences include the transit peptide which targets the NiR protein to the chloroplast or plastid. After transfer to the chloroplast, the transit peptide is cleaved. The length of the transit peptides for each of the sequences was predicted using a web based server at http:/www[DOT]cbs.dtu.dk/services/Target P. The results are shown below in Table 1.

TABLE 1

Details and accession numbers for different NiR cDNAs available in Genbank. Molecular mass ($M_r$), isoelectric points, and charge at pH7 values were calculated using vectorNTI software.

| Name | Species | SEQ ID NO. s (nucleotide, amino acid) | Accession Number | Length (bp) | ORF length a.a. | $M_r$ | Isoelectric point |
|---|---|---|---|---|---|---|---|
| AtNiR | *Arabidopsis thaliana* | 1, 3 | AK221199 | 1761 | 587 | 65.61 | 5.96 |
| CapNiR | *Capisicum annuum* | 18, 19 | AF065616 | 1767 | 589 | 66.1 | 6.89 |
| RicNiR | *Oryza saliva* | 20, 21 | D50556 | 1791 | 597 | 66.25 | 6.89 |
| SpinNiR | *Spinaci oleraceaa* | 22, 23 | X07568 | 1785 | 595 | 66.5 | 6.53 |
| TobNiR1 | *Nicotiana tabacum* | 24, 25 | X66145 | 1752 | 584 | 65.2 | 5.89 |
| TobNiR2 | *Nicotiana tabacum* | 26, 27 | AB103507 | 1764 | 588 | 65.9 | 6.95 |
| TobNiR3 | *Nicotiana tabacum* | 28, 29 | AB093533 | 1764 | 588 | 65.7 | 6.12 |
| TobNiR4 | *Nicotiana tabacum* | 30, 31 | AB093534 | 1755 | 585 | 65.57 | 6.71 |
| ZeaNiR | *Zea mays* | 32, 33 | M23456 | 1704 | 568 | 63.24 | 6.04 |

TABLE 2

Details of predicted target sequence length for NiR proteins. The cTP and mTP values are for chloroplast or mitochondria targeted proteins respectively, the closer the value to 1, the more confident the prediction. Peptides were analysed using TarpetP at http:/www[DOT]cbs.dtu.dk/services/Target P

| Name | Protein length | cTP value | mTP value | other | Predicted target sequence length | Predicted location |
|---|---|---|---|---|---|---|
| AtNiR | 586 | 0.793 | 0.232 | 0.053 | 25 | Chloroplast |
| CapNiR | 588 | 0.773 | 0.312 | 0.079 | 49 | Chloroplast |
| RicNiR | 596 | 0.913 | 0.444 | 0.018 | 28 | Chloroplast |
| SpinNiR | 594 | 0.961 | 0.098 | 0.041 | 32 | Chloroplast |
| TobNiR1 | 583 | 0.696 | 0.458 | 0.056 | 47 | Chloroplast |
| TobNiR2 | 587 | 0.734 | 0.330 | 0.047 | 51 | Chloroplast |
| TobNiR3 | 587 | 0.779 | 0.209 | 0.091 | 51 | Chloroplast |
| TobNiR4 | 584 | 0.633 | 0.380 | 0.048 | 48 | Chloroplast |
| ZeaNiR | 567 | 0.189 | 0.469 | 0.41 | 102 | Mitochondria |

The NiR protein sequences were aligned to the tobacco NiR1 sequence using the EMBL Clustawl program. The *A. thaliana* NiR gene has the least similarity of the dicot polypeptide sequences to tobacco NiR1 (70% homology), making it a good candidate for overexpression in tobacco.

General Methods Used in the Examples

The following methods were used in the subsequent specific examples. A skilled person will appreciate that many of the methods described herein are applicable, either directly or with minor modifications, in alternative embodiments. For instance, although the methods mentioned below for DNA manipulation, transformation of plants and assays for nitrate/nitrite levels are described with reference to the modification of *Nicotiana tabacum* with nitrite reductase from *Arabidopsis thaliana*, similar methods may be used for the transformation of other plant types with alternative nitrite reductase genes.

Plant Material

The tobacco plants used in this study were *Nicotiana tabacum* var. K326, which is a popular, commercially grown, flue-cured variety.

The *Arabidopsis* plants used in this study were *Arabidopsis thaliana* var. Columbia.

Plant Growth Conditions

*Arabidopsis*

*A. thaliana* seeds were surface sown onto Levingtons F1 compost in a propagator tray. The plants were grown in 24 hr light and at 24° C., and were watered by hand. Tobacco

*N. tabacum* seeds were surface sown onto Levingtons F1 compost in a propagator tray under normal greenhouse conditions (averaging 22° C. and 16 hrs light). The propagator lid was left on and removed gradually once the seeds had germinated. When the plantlets had two true leaves they were transplanted into 6 inch pots of potting compost (Levingtons M2).

Transformants

Tissue culture plants were acclimatised to greenhouse conditions by planting into small cells with propagation mix compost (Levingtons F1). After a week, plants were transferred into 6 inch pots of potting compost (Levingtons M2) with 4 g/l of Osmocote® (Scotts Professional Ltd, Bramford, Suffolk, UK) slow release fertilizer containing micro- and macro-elements. The plants were watered by automatically controlled spaghetti drip irrigation. Under these circumstances the tobacco plants took 10 weeks to flower. The average temperature of the greenhouse was 22° C. with 16 hours of day light.

Nitrate Feeding-Trial

In order to manipulate the amount of nitrate received by tobacco plants, a controlled nutrient solution was fed to the plants containing potassium nitrate as the sole nitrogen (N) source, shown in Table 3:

TABLE 3

Recipe of modified Hoaglands solution (Matt et al., 2001) used in feeding-trial studies. The media was buffered with 0.2M Sodium Carbonate solution.

| Chemical | Final Concentration |
| --- | --- |
| Boric Acid | 1 mM |
| Cupric Sulfate | 0.15 µM |
| Ferric Tartrate | 5 µM |
| Mg Sulfate | 1 mM |
| Mn Chloride | 0.5 µM |
| Mo Trioxide | 50 nM |
| Zn Sulfate | 0.35 µM |
| Calcium Chloride | 1 mM |
| K phosphate pH 7 | 0.5 mM |
| K nitrate | 10, 5 or 1 mM |

*N. tabacum* seeds were germinated as described above. When the plantlets had 2 true leaves they were transplanted into 1 inch modules of potting compost (Levingtons M2) and allowed to grow for a further 2 weeks. The plantlets were transplanted into pots containing 1 cm clay pebbles (Hydro-Leka Clay Pebbles; Gro Well Hydroponics, Warwick, UK) standing in 25 cm diameter saucers. The saucers were filled to the brim with the required Hoaglands solution (10, 5 or 1 mM nitrate, see Table 3) and were topped up daily.

Extraction and Purification of DNA

Extraction of Genomic DNA from Plants

Various methods were employed for the extraction of genomic DNA from plant tissues.

1. QIAgen Plant DNA Extraction Method

Genomic DNA was extracted from leaf samples using a QIAgen DNeasy Plant DNA extraction kit (#69106) (QIAgen Ltd., Crawley, UK), following the manufacturers instructions. This method provided large amounts of very clean DNA suitable for gene isolation and cloning strategies. The principle of the kit utilises the specific absorption of DNA under high salt conditions to a silica-gel based membrane whilst contaminants such as proteins, carbohydrates, polyphenolics and other plant metabolites are washed away.

2. Manual DNA Extraction

A second quicker DNA extraction method was employed for PCR screening of transgenic plant populations. This provided good quality DNA but at a much lower concentration than method 1 (Edwards et al., 1991).

A 400 µl aliquot of extraction buffer, consisting of 0.2 M Tris-HCl (pH 8), 0.25 M NaCl, 25 mM EDTA, 0.1% SDS, 40 µg/ml RNAse, was added to 100 mg of plant material. This was ground with a micropestle in a microfuge tube. The solution was vortexed and centrifuged at 13,000 rpm for 10 minutes in a bench top microcentrifuge. 350 µl of clear supernatant was transferred to a new microfuge tube and 350 µl of chloroform:isoamyalcohol (24:1) added. The sample was inverted 5 times and left at room temperature for 10 minutes and then centrifuged at 13,000 rpm for 10 minutes. 300 µl of the aqueous phase was transferred to a new microfuge tube and 300 µl of isopropanol added. The tube was inverted 5 times and left at room temperature for 10 minutes, then centrifuged at 13,000 rpm for 10 minutes to pellet the DNA. The supernatant was poured off and the DNA pellet allowed to air-dry. Lastly 50 µl of sterile distilled water (SDW) was added and the DNA left to dissolve at 4° C.

3. Rapid Alkali Treatment of Plant Material

A rapid alkali treatment was used to prepare plant material for PCR analysis (Klimyk et al., 1993). A 0.5 cm leaf tip was placed in a 96 well PCR plate. 40 µl of 0.25 M NaOH was added and 'boiled' at 100° C. on a PCR machine for 2 minutes to break up the plant cells. The PCR plate was then cooled on ice for 5 minutes. 60 µl of 0.25 M HCl/0.5 M Tris was added to neutralise the solution and vortexed briefly, followed by centrifugation at 3,000 rpm for 5 minutes. 50 µl of the solution was removed to a clean PCR plate and stored at 4° C.

DNA Extraction from *E. coli* (Alkaline Lysis Method)

Transformed plasmid DNA was extracted using a modified method from Sambrook et al., (1989). All solutions except solution II were autoclaved. A 3 ml overnight culture was grown at 37° C. and 1.5 ml was pelleted in a microfuge tube by centrifugation for 2 minutes at 13,000 rpm. The supernatant was drained and 100 µl of solution 1 (50 mM glucose, 25 mM Tris/HCl pH 8, 10 mM EDTA) was added and cells were resuspended by vortexing. The cells were lysed with 200 µl of solution 11 (0.2 M NaOH, 1% SDS) and the tubes inverted 3 times. Finally 150 µl of solution 111 (60 ml 5 M potassium acetate, 11.5 ml acetic acid, 28.5 ml SDW) was added to precipitate proteins and chromosomal DNA. The tubes were inverted 3 times and left to sit for 1 minute at room temperature before centrifuging at 13,000 rpm for 2 minutes. The supernatant was transferred to a new microfuge tube. 1 ml of 100% ethanol was added to precipitate the DNA and the samples were left at −20° C. for at least 15 minutes. The DNA was collected by centrifugation at 13,000 rpm for 10 minutes, washed with 70% ethanol and dried in a desiccator. The DNA was resuspended by adding 50 µl of T. E. solution (10 mM Tris/HCl pH 8, 1 mM EDTA)

plus 10 µg/ml RNase solution. This protocol normally yielded about 0.5 µg-1 µg/µl plasmid DNA.

DNA Extraction from *Agrobacterium* (Modified Mo-Bio Method)

To extract plasmid DNA from transformed *Agrobacterium tumefaciens*, 4 mls of the *A. tumefaciens* culture was placed into a microfuge tube and centrifuged in a bench top microcentrifuge for 1 minute at 13,000 rpm. The Mo-Bio DNA extraction kit (#UC-12300-250 Cambio Ltd., Dry Drayton, Cambridge, UK) was used which employs the same principle as the alkaline lysis DNA extraction procedure but follows more stringent cleaning processes. This involves binding the DNA to a silca membrane under high salt conditions and washing off impurities such as digested RNA and other cell components. The DNA is then eluted from the membrane with SDW. As the kit is designed principally for DNA extraction from *E. coli* there was a slight modification to the manufacturers instructions (all solutions were supplied with the Mo-Bio kit). The pelleted cells were resuspended in 100 µl of solution I, 200 µl of solution II was added and the tubes inverted three times. 650 µl of solution III was added, inverted 3 times and the solution was centrifuged for 6 minutes at 13,000 rpm to pellet the debris. The supernatant was loaded onto a spin filter column (supplied with the kit) and centrifuged at 6,000 rpm for 30 seconds. Liquid in the collection tube was discarded and 300 µl of solution IV was added and centrifuged at 6,000 rpm for 30 seconds. The liquid in the collection tube was discarded. 100 µl of SDW was added to the spin filter and left to stand for 1 minute before centrifuging at 6,000 rpm for 30 seconds. The eluant was precipitated with 10 µl of 5 M NaCl and 200 µl of ethanol and left on ice for 15 minutes. A 10 minute centrifugation at 13,000 rpm precipitated the DNA and it was then washed with 100 µl of 70% ethanol followed by a brief 2 minute spin. The pellet was air dried and then resuspended in 10 µl SDW ready for restriction digest analysis.

Precipitation of DNA

Plasmid DNA was precipitated with 1/10th volume 5 M NaCl and 2 volumes of ethanol at −20° C. for at least 15 minutes. The solution was centrifuged in a bench top centrifuge for 10 minutes at 13,000 rpm. The supernatant was poured off and 100 µl of 70% ethanol added. The solution was centrifuged for a further 5 minutes. The supernatant was poured off and the sample dried in a bench top desiccator for 5 minutes. The DNA pellet was resuspended in SDW to the desired volume for the application required.

Quantification and Analysis of DNA

DNA Quantification

DNA concentration was estimated by UV-Spectophotometry. DNA absorbs UV light with a maximum peak at 260 nm. DNA samples were diluted by taking 5 µl of DNA sample and 495 µl of SDW. The absorbance (A) was measured at 260 nm and 280 nm against a blank of SDW in a quartz cuvette with a 1 cm path length. One absorbance unit at 260 nm is equivalent to 50 µg/ml DNA. The following formula was used to calculate the concentration of DNA.

$$(A_{260} \text{ sample} - A_{260} \text{ blank}) \times 50 \times 100 = \mu g/ml \text{ DNA}$$

Where 50 is the double stranded DNA coefficient and 100 is the dilution factor

To calculate the purity of the DNA samples, the absorbance at 280 nm was also measured. Proteins and other contaminants absorb light at 280 nm. Therefore, the 260:280 ratio gives an indication of purity, a value of 1.8-2.0 indicates there is little or no contamination with proteins or phenols.

Agarose Gel Electrophoresis

Agarose gels (1%) were prepared in 1×TBE (Tris-borate: 90 mM Tris, 90 mM boric acid, 2 mM EDTA), containing 0.01 µg/ml ethidium bromide. DNA samples were mixed with 1/6th loading buffer (60% Sucrose, 5% Egg Yellow). A lambda DNA marker ladder (5 µl) was loaded onto the gel along with the DNA samples and separated by electrophoresis in 1×TBE buffer at 120 volts for 1.5 hours. The gel was visualised on a UV transilluminator (UVP BioImaging Systems, UVP Inc., Cambridge, UK) and photographed.

Lambda DNA Marker

To provide a visual guide to DNA sizes separated by electrophoresis, 60 µg Lambda DNA (Promega Biosciences Inc., Southampton, UK) was digested with 50 units of restriction enzyme PstI (Promega Biosciences Inc., Southampton, UK) in a reaction with 2.5 µl BSA (10 mg/ml), 25 µl Pst1 Buffer (Promega) and SDW to 250 µl. The digest was incubated for 12 hours at 37° C., and the reaction was stopped by the addition of 5 µl of 0.5 M EDTA. 50 µl of 6× Blue loading buffer (60% sucrose, 100 mM Tris pH8, 0.25% Bromophenol Blue) was then added. 5 µl of the prepared marker provided approximately 1 µg of a DNA ladder.

Isolation from Agarose Gel

To isolate and purify DNA fragments they were first separated on an agarose gel by electrophoresis. The gel was visualised on a low energy UV transilluminator and the desired DNA fragments were cut out and placed in a microfuge tube. The QIAquick Gel Extraction Kit (QIAgen-Ltd, Crawley, UK) was used according to the manufacturer's instructions. The principle involves the absorption of DNA to a silica-membrane whilst in the presence of high salt. Any contaminants are washed off and pass through the column.

Three volumes of GQ buffer was added to one volume of gel and the mixture incubated at 50° C. for 10 minutes, with agitation every 2-3 minutes, until the gel slice had completely dissolved. The colour of the mixture should remain yellow indicating that the mixture is at the optimum pH for adsorption of DNA to the QIAquick membrane. One gel volume of isopropanol was added to each sample. Samples were applied to the column and centrifuged for 1 minute at 13,000 rpm. The flow-through was discarded before the addition of 0.5 ml of QG buffer to remove all traces of agarose. The column was washed by adding 0.75 ml of buffer PE and centrifuged for 1 minute. The flow-through was discarded before a further centrifugation of the column. DNA was then eluted by addition of 100 µl of elution buffer (10 mM Tris-HCl, pH 8.5) to the centre of the column and left to stand for 1 minute before centrifugation at 13,000 rpm for 1 minute.

The DNA (100 µl) was precipitated as previously described, and resuspended in SDW to the volume desired for each specific application.

DNA Manipulation

Restriction Digests

Restriction endonucleases were purchased either from Promega (Promega Biosciences Inc., Southampton, UK) or New England Biolabs (New England Biolabs (UK) Ltd, Hitchin, Herts, UK).

All restriction digests were normally carried out using 1 µg of DNA. This was digested with 10 units of endonuclease in a 30 µl reaction, which included 3 µl of the appropriate 10×buffer. The reactions were incubated at 37° C. for 2 hours, unless otherwise stated.

Alkaline Phosphatase Treatment of Plasmids for Cloning

In order to prevent religation of plasmids digested with compatible endonuclease sites, the 5' end phosphate group was removed by phosphatase digestion. This was performed using the enzyme Shrimp Alkaline Phosphatase (Promega Biosciences Inc., Southampton, UK). A 20 µl reaction consisting of 2 µl of 10× Shrimp Alkaline Phosphatase buffer, 1 µl of Shrimp Alkaline Phoshpatase and 2 µg cut DNA was incubated at 37° C. for 30 minutes. The reaction was stopped by heat inactivation of the enzyme at 65° C. for 20 minutes. The DNA was used for ligation without further purification.

Ligation of DNA Fragments

Ligations were set up using 0.1 µg of cut vector (such as pSK or pBNP) and 0.5 µg of insert (such as the digested *A. thaliana* nitrite reductase amplified DNA). A 20 µl ligation reaction consisted of 0.1 µg vector DNA, 0.5 µg insert DNA, 1 µl T4 DNA ligase (Promega Biosciences Inc., Southampton, UK) and 2 µl 10× T4 ligase buffer (Promega). As a negative control, vector only was used in the ligation reaction.

The ligation mix was incubated at room temperature for 2 hours. 2 µl of the reaction was diluted with 3 µl of SDW and added to 40 µl of electro-competent cells for transformation into *E. coli*.

TOPO TA Cloning®

For analysis of novel PCR amplicons, the amplicons were cloned into an appropiate vector. TOPO TA Cloning® is a one step cloning strategy for the direct insertion of Taq polymerase amplified PCR products. It uses the terminal transferase activity of Taq polymerase which adds a deoxyadnosine (A) to the 3' ends of PCR products. A linearised vector (pCR® 4-TOPO®; Invitrogen Life Technologies, Paisley, UK) is supplied which has a single thymidine (T) overhang and this, along with the enzyme topoismerase, allows PCR inserts to ligate with the vector. The reaction uses 1 µl of fresh PCR product added to a mix of 1 µl TOPO® vector, 1 µl salt solution (supplied with TOPO® TA cloning kit; Invitrogen Life Technologies, Paisley, UK) and SDW to 6 µl. The reaction was incubated for 5 minutes at room temperature before transforming into One Shot® TOP10 competent cells, as described by the manufacturer (Invitrogen Life Technologies, Paisley, UK).

DNA Sequencing

All plasmid clones were sequenced to confirm the presence of the PCR amplicon or transgene, by sending 10 µl of the purified plasmid DNA (100 ng/µl) to LARK Technologies Inc., Saffron Walden, Essex, UK. Universal primers (M13F, M13R, T3 and T7) were supplied by Lark, but sequence specific primers were sent with the DNA (10 µl of 30 µM solution). A chromatogram of the sequence was returned which was imported into the Vector NTI Advance™ software suite (Invitrogen Corporation, Bioinformatics, UK) for analysis by alignment to database sequences or BLAST analysis (http://www[DOT]ncbi.nlm.nih.gov/BLAST).

Bacterial Manipulation

Bacterium

For all cloning experiments *Escherichia coli* Nova blue (Novagen®, Merck Biosciences Ltd, Nottingham, UK) was used.

For transformation experiments into *N. tabacum*, *Agrobacterium tumefaciens* LBA4404 was used.

Production of Electrocompetent Bacterium for Transformations

All media, growth flasks and centrifuge bottles were autoclaved before use. 5 mls of the rich growing media 2YT (2×Yeast and Tryptone; 10 g/L tryptone, 10 g/L yeast extract, 5 g/L NaCl) were inoculated with a single bacterial colony for an overnight culture. The culture was grown at either 37° C. for *E. coli* or 28° C. for *A. tumefaciens*. 500 mls of 2YT was warmed for half and hour at the required temperature for the bacterium strain, the pre-warmed media was inoculated with the overnight culture and allowed to grow until $OD_{600}$ was 0.4-0.6. The culture was then chilled on ice for 30 minutes. The cells were harvested at 4,000 rpm for 15 minutes at 4° C. in an ultra-centrifuge. Cells were washed with 250 mls of ice cold 10% glycerol, centrifuged and the wash repeated. Cells were harvested and resuspended in 2 mls of ice cold Glycerol Yeast and Tryptone medium (GYT; 10% glycerol, 0.125% yeast extract, 0.25% tryptone). 90 µl aliquots were flash frozen in liquid nitrogen and stored at −80° C. until required.

Electroporation and Transformation of DNA into *E. coli*

40 µl of electrocompetent cells and 5-100 ng of DNA were mixed and placed in a pre-cooled electroporation cuvette (EQUIBIO, Geneflow Ltd, Staffordshire, UK) and electroporated at 1.5 Volts, 800 Ohms and 25 µFD (BioRad Gene Pulser, BioRad Laboratories, UK). 1 ml of 2YT media was added to the cuvette and the mixture was decanted into a 30 ml universal container and incubated at 37° C. for 1 hour in a shaking incubator. 10 µl of cells were then plated onto either Ampicillin (100 µg/ml) Luria-Bertani (LB) agar plates (1.5 g agar/100 mls, 4 pellets of circle grow bacterial growth media (BIO 101 Inc., California, USA)/100 mls) or Kanamycin (50 µg/ml) LB agar plates. The plates were incubated overnight at 37° C. As a control, an equivalent aliquot was spread onto LB plates without Ampicillin.

Blue White Selection of Transformed *E. coli*

When using pBluescript cloning vector (pSK; Stratagene®, UK), the multiple cloning site is within the bacterial lacZ gene which codes for the reporter protein β-galactosidase. β-galactosidase cleaves the colourless substrate X-GAL (5-bromo-4-chloro-3-indolyl-β-galactopyranoside) into galactose and a blue insoluble product, which acts as a marker. Upstream of the lacZ gene there is an inducible promoter which on addition of isopropyl-β-D-thiogalactopyranoside (IPTG) induces transcription of lacZ. Therefore, if cloning has been successful, the lacZ gene is disrupted and no β-galactosidase reporter protein will be synthesised and no blue colour formed.

Transformed cells were plated onto AXI agar plates (1.5 g agar/100 mls, 4 pellets of circle grow/100 mls, ampicillin 100 µg/ml, IPTG 0.1 mM, XGal 0.004%). After incubation overnight at 37° C. the presence of white colonies indicated that the insert had been successfully ligated into pSK. Any blue colonies indicated that the pSK vector had re-ligated and did not contain the insert.

Electroporation and Transformation of DNA into *Agrobacterium*

40 µl of *A. tumefaciens* electrocompetent cells and 0.5 µg of plasmid DNA were mixed, placed in a pre-cooled cuvette and electroporated at 1.5 Volts, 600 Ohms and 25 µFD. 1 ml of 2YT media was added to the cuvette and the mixture was decanted into a 30 ml universal container and incubated at 28° C. for 2 hours in a shaking incubator. 100 µl of cells were then plated onto kanamycin (50 µg/ml) and streptomycin (100 µg/ml) LB agar plates. The plates were left to incubate for 2 days at 28° C.

Growth of Transformed *E. coli* Cultures for DNA Extraction

Colonies were picked from plates using a sterile wooden toothpick and placed into 3 ml of 2YT media with the appropriate antibiotic. The cultures were then grown at 37° C. overnight in a shaking incubator.

Growth of Transformed *Agrobacterium* Cultures for DNA Extraction

Colonies were picked from plates using a wooden toothpick and placed into 5 ml of 2YT media with kanamycin (50

µg/ml) and streptomycin (100 µg/ml) antibiotics. The cultures were then grown at 28° C. for 2 days in a shaking incubator.

Generation of Transgenic Tobacco

All procedures were carried out in a sterile flow cabinet using aseptic techniques. The two youngest leaves from 7-8 week old tobacco plants were cut and sterilised in 8% Domestos for 10 minutes and rinsed 4 times with SDW. 1 cm diameter leaf discs were taken along the smaller veins (but not the midrib) and immersed in approximately 25 ml of an overnight *A. tumefaciens* culture ($A_{600}$ 0.6-0.8). The solution was mixed by swirling for approximately two minutes. The leaf discs were then blotted onto filter paper. 10 leaf discs per plate were plated onto Murashige and Skoog medium (Duchefa Biochemie BV, Holland) plus 2.2 µM 6-benzyl aminopurine (BAP) a cytokinin growth regulator, and 0.27 µM 1-naphtalene acetic acid (NAA), an auxin growth regulator. Control leaf discs of non-immersed leaf discs were also plated. Plates were sealed with cling film and placed in a growth room at 22° C. with artificial lighting. After 2 days the discs were transferred to plates (5 discs per plate) containing the antibiotics claforan (500 µg/ml) and kanamycin (100 µg/ml). A control plate containing only claforan was also plated. The leaf discs were transferred every 14 days to fresh media. After about 8-10 weeks, callus and shoots could be detected. The shoots, when large enough, were transferred onto a plate with Linsmaier and Skoog media (LS) plus 2.2 µM BAP with claforan and kanamycin as before (only one shoot from each leaf disc was taken). After 2 weeks the shoots were placed into jars of the same media but without kanamycin. Two weeks later the dominant shoot was transferred to a new jar of LS media with claforan (250 µg/ml). After a further 2 weeks shoots were transferred into jars of LS media only. When shoots had produced roots they were planted out into the greenhouse (see above).

DNA Amplification by Polymerase Chain Reaction (PCR)

DNA Amplification from Bacterial Cultures

To rapidly screen bacterial colonies for the presence of transgenes, the colonies were amplified by PCR directly. A sterile toothpick was used to touch the centre of a bacterial colony. The toothpick was placed into the well of a U-bottom lidded 96 well plate (Costar®, Corning Inc., NY, USA) containing 50 µl of 2YT medium plus antibiotic selection. This was performed for each colony to be screened. The plate was incubated at 37° C. for 2 hours in a shaking incubator.

A PCR master mix was created for the number of colonies to be screened. The final volume for each reaction was 10 µl and consisted of 1 µl Taq buffer (ABgene®, Epsom, Surrey, UK), 1 µl 2 mM dNTP solution, 0.1 µl forward primer (100 pmol/µl), 0.1 µl reverse primer (100 pmol/µl), 0.3 µl Taq polymerase (5 U/µl; ABgene®), and 7.5 µl SDW.

10 µl of PCR reaction mix was pipetted into each well of a short-skirted PCR microtitre plate (ABgene®). A 96 well replicator (Costar®) was used to transfer no more than 0.5 µl of culture into the PCR plate. Control wells were set up containing a PCR blank (no DNA) and a positive control. PCR conditions were dependant on the template and primers used, but as a rule were as follows: 95° C. for 4 minutes, 35 cycles of 95° C. for 30 seconds, annealing at 55° C. for 30 seconds and template extension at 72° C. for 1 minute, finished with a 'polishing' step of 72° C. for 4 minutes. The completed reactions were loaded onto an agarose gel for electrophoresis.

Amplification of DNA for Cloning

Conventional Taq DNA polymerase creates one error every 500 bases, therefore for cloning purposes a PCR additive was employed which improves the reliability and efficiency of PCR amplification and reduces mismatch pairing. Taq Extender™ PCR Additive (Stratagene, UK) was added to 25 µl PCR amplification reactions. This typically consisted of 50 ng of template, 2.5 µl Taq extender buffer, 2.5 µl 2 mM dNTP solution, 0.25 µl forward primer (100 pmol/µl), 0.25 µl reverse, SDW to 25 µl. The amplification conditions were as for colony PCR (see 2.9.1). 5 µl of the completed reactions were loaded onto an agarose gel for analysis by electrophoresis.

Amplification of DNA for Screening Transgenic Tobacco

When a transgenic plant population was produced, genomic DNA was extracted as described previously. The presence of the transgene was analysed by PCR using the same method as described for colony PCR but using plant genomic DNA as the template. A PCR master mix was created for the number of plants to be screened. The final volume for each reaction was 10 µl and consisted of 1 µl Taq buffer (ABgene®, Epsom, Surrey, UK), 1 µl 2 mM dNTP solution, 0.1 µl forward primer (100 pmol/µl), 0.1 µl reverse primer (100 pmol/µl), 0.3 µl Taq polymerase (5 U/µl; ABgene®) and 6.5 µl SDW.

9 µl of PCR reaction mix was pipetted into a PCR plate (ABgene®) and 1 µl genomic DNA. Control wells were set up containing a PCR blank (no DNA) and a positive control. PCR conditions were dependant on the template and primers used, but as a rule were as follows: 95° C. for 4 minutes, 35 cycles of 95° C. for 30 seconds, annealing at 55° C. for 30 seconds and template extension at 72° C. for 1 minute, finished with a 'polishing' step of 72° C. for 4 minutes.

The PCR products were loaded onto an agarose gel for electrophoresis.

Copy Number Analysis by Real-Time PCR

Real-time PCR experiments were carried out using the BIO-RAD I-Cycler™ real-time detection system (Bio-Rad Laboratories, UK). SYBR Green fluorescent DNA binding dye (SYBR® Green Supermix, Bio-Rad Laboratories, UK) was used to detect amplicons. As the amount of amplified DNA increases, it reaches a level of fluorescence significantly higher than the background, this point is known as the threshold cycle (Ct). The Ct bears a linear relationship to the amount of target DNA in the reaction. The amount of target DNA in a test sample can be calculated by comparing the samples threshold cycle to a standard curve obtained from the threshold cycles of reference standards (BIORAD tech note 2697). Two methods were employed to estimate transgene copy number.

Absolute Quantification

The absolute quantitation method is based on using a quantitative amount of DNA and relating the PCR signal to a standard curve in order to extrapolate the copy number (BIO-RAD technical note 2697). A virtual calibrator can also be employed which is a known transgenic line, but of unknown copy number, to compare to other transgenic lines. This assumes that at least one line will contain one copy.

Genomic DNA was digested with Ssp1 endonuclease (1 µg genomic DNA, 5 µl Ssp1 buffer (Promega), 10 units Ssp1 endonuclease (Promega), SDW to 50 µl) by incubating at 37° C. for at least 2 hours. The enzyme was inactivated at 70° C. for 10 minutes. Standard curves were generated using serial dilutions of plasmid DNA (pBNPAtNiR) and genomic DNA of one transgenic line (virtual calibrator) to compare standard curve efficiencies. The primer pair At1300F and At1440R were used in the PCR reaction (0.25 pM forward primer, 0.25 pM reverse primer, 12.5 µl SYBR-green mix (Bio-Rad laboratories, UK), 1 µl diluted DNA, SDW to 25 µl). The PCR conditions were; 1 cycle at 95° C. for 3 minutes followed by 45 cycles of 95° C. for 30 seconds and 55° C. for 30 seconds. A melt curve was generated by 80 cycles at 30 second intervals, increasing the temperature from 55° C. to 95° C. in 0.5° C. increments. All reactions were performed in 4 replicates and the data collected by the I-cycler iQ™ software (Bio-Rad laboratories, UK). For each transgenic sample, 250 ng of genomic DNA was analysed and compared with the standard curves. This procedure makes the assumption that one of the transgenics will only contain one copy of the transgene and the highest Ct values will be the lines with the lowest copy number. Ct values were compared and differences of 1 Ct would represent a two fold difference in target DNA. Controls containing no DNA and non-transgenic genomic DNA were also included.

Comparative Ct Method

This method allows for the analysis of unknown amounts of DNA by comparing the Ct value of a transgene to that of an endogenous gene (German et al., 2003, Weng et al., 2004). The number of copies of endogenous gene (or reference gene) per genome remains constant, whereas the number of copies of a transgene (or target gene) can vary, therefore the ratio of target to reference gene will indicate the copy number of the transgene. For the Ct calculation to be valid, the efficiency of the target amplification and the efficiency of the reference amplification must be taken into account therefore standard curves have to be produced for both the target and reference gene. The reference gene used was nitrate reductase (NR), with the primer pair NIAF and NIAR, and the target gene was AtNiR, with the primer pair At1300F and At1440R. Genomic DNA was extracted but not quantified and each sample was amplified twice using both sets of primers with the same volume of DNA added. The PCR reaction (0.25 pM forward primer, 0.25 pM reverse primer, 12.5 µl SYBR-green mix (Bio-Rad laboratories, UK), 1 µl DNA, SDW to 25 µl) was 1 cycle at 95° C. for 3 minutes followed by 45 cycles of 95° C. for 30 seconds and 55° C. for 30 seconds. A melt curve was generated by 80 cycles at 30 second intervals of increasing temperature from 55° C. to 95° C. in 0.5° C. increments. This melt curve was used to identify that the correct amplicons had been generated. The equation from Weng et al., (2004) was used to calculate copy number;

$$[(Ct_{tar} - I_{tar})/S_{tar}] - [(Ct_{ref} - I_{ref})/S_{ref}]$$

$$X_0/R_0 = 2$$

Where:

$Ct_{tar}$ or $Ct_{ref}$=Ct value for target and reference genes
$I_{tar}$ or $I_{ref}$=Intercept of relative standard curves
$S_{tar}$ or $S_{ref}$=Slope of relative standard curves
2 is the dilution factor for the standard curves Primer Design Primers were designed differently depending on what application they were required for. All primers were synthesised by Invitrogen Custom Primers (Invitrogen™, Paisley, UK). The sequences of all primers were checked against publicly available sequences for unspecific priming sites using BLAST (http://www[DOT]ncbi.nlm.nih.gov/BLAST)

Cloning Primers

Cloning primers were designed manually by taking approximately 20 bp of sequence from the 5 and 3' ends of the DNA fragment to be cloned, and adding the desired endonuclease sites plus 3 extra base pairs at the end to ensure efficient digestion. The primers were then analysed for duplex and hairpin formation as well as melting temperature on the VectorNTI software program (Invitrogen Corporation, Bioinformatics, UK) to confirm that they were suitable for cloning (see Table 4).

TABLE 4

Description of primers synthesised and employed for cloning A.thaliana NiR clones

| PRIMER NAME | PRIMER SEQUENCE 5' to 3' | PRIMER DESCRIPTION |
|---|---|---|
| ARFULLF (SEQ ID NO: 4) | ATCGAGCTCGGATCCATGACTTCTTT CTCTCTCAG | 5' Cloning primer for A.thaliana NiR with BamHI and SacI sites |
| ARFULLR (SEQ ID NO: 5) | GATGAGCTCGGATCCTACCTCAATC TTCATTCTC | 3' Cloning primer for A.thaliana NiR with KpnI and SacI sites |

PCR and Sequencing Primers

Primers were designed using the VectorNTI software program (Invitrogen Corporation, Bioinformatics, UK), and for PCR generated products between 400 and 800 bp long for quick amplification and verification by agarose gel electrophoresis.

TABLE 5

Description of primers synthesised and employed for screening transgenic plant populations

| PRIMER NAME | PRIMER SEQUENCE 5' to 3' | PRIMER DESCRIPTION |
|---|---|---|
| ARA3F (SEQ ID NO: 6) | TTTATCACCGCTAATTCA | Anneals to positive strand of A.thaliana NiR at 1292 bp |
| ARA3R (SEQ ID NO: 7) | TTAGGATAGATGGTTCA | Anneals to complementary strand of A.thaliana NiR at 1726 bp (full length sequence |

TABLE 5-continued

Description of primers synthesised and
employed for screening transgenic plant populations

| PRIMER NAME | PRIMER SEQUENCE 5' to 3' | PRIMER DESCRIPTION |
|---|---|---|
| ARA5F (SEQ ID NO: 8) | CTCTTTATCTTTAGTACA | Anneals to positive strand of A.thaliana NiR at 515 bp (full length sequence) |
| ARA5R (SEQ ID NO: 9) | AGAGAGGAGGAACAGACA | Anneals at 389 bp of the complementary strand of A.thaliana NiR |
| CERV3F (SEQ ID NO: 10) | TGTTAAGGCATCGAAAAA | Anneals at −70 bp on the positive strand of the CERV promoter |
| LUC3OUT (SEQ ID NO: 11) | GGATTACGTCGCCAGT | Anneals to positive strand of LUC at 1502 bp |
| LUC5OUT (SEQ ID NO: 12) | TCTTCCAGCGGATAGA | Anneals to complementary strand of LUC at 46 bp |
| PIVR1 (SEQ ID NO: 13) | GATCAGCTGCACATCAACAAATTTTGGTCA | Anneals at 3' of LUC intron on the complementary strand |

Real-Time PCR Primers

Primers were designed using the web-based software Mfold (http://www[DOT]bioinfo.rpi.edu/applications/mfold). The required size of amplicons was less than 150 bp to allow for quick amplification and analysis, and the annealing temperature was 55° C.

TABLE 6

Description of primers used in real-time PCR experiments

| PRIMER NAME | PRIMER SEQUENCE 5' to 3' | PRIMER DESCRIPTION |
|---|---|---|
| AT1300F (SEQ ID NO: 14) | TGCTGATGACGTTCTTCC | Forward real-time primer for A.thaliana NiR |
| AT1440R (SEQ ID NO: 15) | TGCAAGAAGCATGTAC | Reverse real-time primer for A.thaliana NiR |
| NIAF (SEQ ID NO: 16) | GGTCTTTCAAGCCTCGGTCTG | Forward real-time primer for N.tabacum NR |
| NIAR (SEQ ID NO: 17) | GGAAGGGAATTCGTTAACCAA | Reverse real-time primer for N.tabacum NR |

Protein Analysis

Soluble Protein Measurements

The protein concentration was measured according to Bradford (1976). Plant material was extracted according to the type of analysis to be performed. Each extract (1 μl to 5 μl) was diluted with 200 μl of prepared Bradford's reagent (diluted 1:4 with SDW; Bio-Rad laboratories, Munich, Germany) in a 96 well microtitre plate. Each sample was measured in triplicate at 595 nm in a microplate spectrophotometer (MicroTeK, Kontron Instruments, USA). Bovine serum albumin (BSA) was used to generate a standard curve. Samples were mixed thoroughly and left to stand for 10 minutes before reading the absorbance at 595 nm. The protein concentration of each sample was then calculated from a BSA calibration curve.

Sodium Dodecyl Sulphate-Polyacrylamide Gel Electrophoresis (SDS-PAGE)

Proteins for SDS-PAGE analysis were extracted from plant material using Overcoat buffer (100 mM Tris pH 7.5, 10 mM $KCl_2$, 5 mM $MgCl_2$, 0.4 M sucrose, 10% glycerol, 10 mM β-mercaptoethanol). Approximately 100 mg of leaf material was ground with 100 μl of Overcoat buffer in a microfuge tube using a micropestle. The extraction was kept on ice and centrifuged at 13,000 rpm for 5 minutes and the supernatant transferred for analysis. 10 μg of protein was aliquoted and NuPAGE sample buffer (Invitrogen™, Paisley, UK) added. The samples were all heated at 70° C. for 10 minutes to denature.

Denaturing SDS-PAGE gels were run as described by Laemmli (1970), using a NuPAGE mini gel system (Invitrogen™, Paisley, UK). The protein samples were loaded onto pre-cast 4-12% Bis-Tris SDS-PAGE gels (Invitrogen™, Paisley, UK) and run in 1×MOPS running buffer (20×Stock solution; 1 M 3-(N-morpholino) propane sulfonic acid (MOPs), 1 M Tris Base, 2% SDS, 20.5 mM EDTA-SDW to 500 ml). 5 μl of SeeBlue Marker (Invitrogen™, Paisley, UK) or 8 μl for Western transfers was used to determine molecular mass. The gels were electrophoresed with 0.5 ml of NuPAGE antioxidant (Invitrogen™, Paisley, UK) added to the upper chamber and ran at 200 volts for 1 hour. The gel was either stained with Coomasie Blue (10 mg Brilliant Blue R-250 in 25 mls water/methanol/acetic acid 60:30:10) to visualise the proteins or used in a Western blot transfer (see below).

Western Blot Transfer

Proteins were blotted to nitrocellulose membrane (0.45 µm pore size; Invitrogen™, Paisley, UK) using a Sure-Lock™ mini-cell (Invitrogen™, Paisley, UK) and transfer buffer (50 mls 20× NuPage Transfer buffer, 850 mls SDW, 100 mls methanol, 1 ml antioxidant). The nitrocellulose membrane, filter paper and pads were all pre-wetted in 1×transfer buffer. The SDS-PAGE gel was placed onto the nitrocellulose membrane (making sure no bubbles were evident between membrane and gel) and then filter paper placed on both sides of the gel/membrane assembly. Two blotting pads were placed into the cathode core and the gel sandwich was placed on top so that the gel was closest to the cathode core. Pre-soaked blotting membranes were placed on top and the cathode core closed. The cathode chamber was then filled with transfer buffer. The outer buffer chamber was filled with SDW and the western run at 30 volts for 1.5 hours.

The nitrocellulose membrane was placed in blocking solution (Tris Buffered Saline (TBS) Tween; 20 mM Tris pH 7.6, 0.8% NaCl, 0.1% Tween20 with 5% milk powder) in order to block non-specific sites. This was incubated with gentle agitation for at least 2 hours or overnight.

The specific antibodies for the detection of N. tabacum nitrite reductase (TobNiR) and A. thaliana NiR (AtNiR) polypeptides were raised in rabbits using synthetic peptides (16-mers) designed to areas of the NiR proteins (Covalab Ltd., Cambridge, UK). These primary antibodies were prepared (1:1000 dilution) in TBS-Tween (as above). The membrane was added to the antibody solution and left to shake at room temperature for at least 1 hour. The primary antibody was removed and the membrane washed with TBS-Tween (about 50 ml) with 3 brief washes followed by three 15 minute washes. The secondary antibody (anti-rabbit, horse radish peroxidase linked antigen; Amersham Biosciences, Bucks, UK) was added at 1:4000 dilution in TBS-Tween and incubated for 2 hours with shaking. Membranes were washed as above.

Antibody binding was detected using ECL detection reagents (Amersham Biosciences, Bucks, UK). Equal amounts of ECL detection reagents 1 and 2 were added together, placed onto the membrane and incubated for up to 5 minutes at room temperature. The excess reagent was drained from the membrane and the membrane was covered in cling film. It was then exposed to film (Kodak BioMax Film, Anachem, Luton, UK). Bands usually appeared after 5 minutes exposure.

Reporter Gene Assays

β-Glucuronidase Staining

To identify the presence of the reporter gene β-glucoronidase (GUS) in specific plant cell types, the substrate 5-bromo-4-chloro-3-indolyl-β-D-glucuronic acid (X-GLUC) was added and on reduction by GUS produced a localised blue coloured product.

Plant material was immersed and incubated in GUS staining buffer (50 mM potassium phosphate buffer pH 7, 0.5 mM potassium ferricyanide, 0.5 mM potassium ferrocyanide, 1 mM X-GLUC, 0.1% Triton X-100) and incubated overnight at 37° C.

The solution was removed and the material incubated in 70% ethanol at 37° C. to remove any chlorophyll. This could take 2 days with repeated changes of 70% ethanol every 5 hours, especially if the tissue was very green. When all of the chlorophyll had been removed, the blue coloured GUS staining was readily visualised.

Quantitative Luciferase Assay

Luciferase is a versatile and common reporter gene. The protein from firefly (Photinus pyralis) catalyzes the bioluminescent oxidation of luciferin in the presence of ATP, magnesium and oxygen and the photons emitted can be measured in a luminometer (Lumistar Galaxy, BMG Labtechnologies, Offenbery, Germany). Luciferase activity was measured in plants by grinding approximately 100 mg of leaf material in 200 µl of cold luciferase grinding buffer (LGB; 1 mM DTT, 100 mM Potassium Phosphate buffer pH 7). Samples were kept on ice. The samples were centrifuged at 10,000 rpm for 5 minutes in a bench-top micorcentrifuge at 4° C. The supernatant was removed to a fresh 1.5 ml microfuge tube or 96 well plate and 50 µl of the sample was placed in to a white 96 well plate in triplicate. 50 µl of Bright-Glo assay reagent (Promega Biosciences Inc., Southampton, UK) was injected and the Relative Light Units (RLU) on the luminometer calculated by the luminometer for each sample.

Enzyme Activity Assays

Assay for Nitrite Reductase Activity

Approximately 1 g of tissue was ground in 5 mls of ice cold extraction buffer (50 mM Tris-HCl pH 7.5, 100 µM PMSF, 1 mM EDTA, 10 mM Mercaptoethanol), and centrifuged at 8,000 rpm for 15 minutes at 4° C. The supernatant was removed for analysis and kept on ice. 90 µl of crude enzyme solution was added to 390 µl warm assay solution (50 mM Tris-HCl pH 7.5, 1 mM sodium nitrite, 1 mM methyl viologen, 30° C.). The reaction was started by addition of 120 µl sodium dithionite solution (25 mg/ml sodium dithionite in 290 mM sodium bicarbonate).

A time zero (T0) sample was immediately taken which consisted of removing 10 µl of the reaction, adding it to 240 µl of water and vigorously mixing to stop the reaction. The main reaction was incubated at 30° C. for 5-15 minutes depending on the speed of the reaction. 10 µl of the reaction mixture was removed after 5 or 15 minutes and added to 240 µl of water and vigorously mixed to stop the reaction. 50 µl of each stopped reaction was placed in a 96 well plate (this was done in triplicate) and 50 µl of 1% (w/v) sulfanilamide in 3N HCl and 50 µl of 0.02% (w/v) n-napthylethylenediamine dichydrochloride (N-NED) was added and left for 15 minutes to allow any colour to develop. The absorbance was read at 540 nm. The T5 (or T15) value was taken away from the T0 value to measure the change in nitrite concentration over time. Potassium nitrite was used to generate a standard curve.

Assay for Nitrate Reductase Activity

Nitrate reductase (NR, EC 1.6.6.1) catalyzes the 2 electron reduction of nitrate to nitrite.

The enzyme assay is an absorbance based assay measuring the increase of nitrite ions in the assay mixture over time (Ferrario-Méry et al., 1998). NR has different activation states, phosphorylated (inactive) and unphosphorylated (active), the assay used was for maximal NR activity which is the unphosphorylated form of the enzyme.

The same extract was used as for nitrite reductase assay. 400 µl of crude enzyme solution was added to 600 µl of assay solution (50 mM Tris-HCl pH 7.5, 30 mM Potassium nitrate, 0.15 mM NADH, 20 µM FAD, 0.1 mM EDTA, 0.1 mM DTT). A time zero (T0) sample was immediately taken which consisted of removing 50 µl of the reaction and adding to 50 µl of 1% (w/v) sulfanilamide in 3 N HCl and 50 µl of 0.02% (w/v) N-NED. The main reaction was incubated at 30° C. for 60 minutes. After 1 hour 50 µl of the reaction was removed and added to 50 µl of 1% (w/v) sulfanilamide in 3 N HCl and 50 µl of 0.02% (w/v) N-NED.

Colour was allowed to develop over 15 minutes and the absorbance read at 540 nm. The T0 value was taken away from the T60 value to measure the change in nitrite concentration over time. Potassium nitrite was used to generate a standard curve.

Assay for Glutamate Dehydrogenase—Amination Activity

Glutamate Dehydrogenase (GDH, EC 1.4.1.3) amination catalyzes the conversion of ammonia to glutamate by the assimilation of 2-oxoglutarate. The enzyme assay measures the absorbance of NADH at 340 nm, which decreases due to the oxidation of NADH as a result of GDH-aminating activity (Turano et al., 1996).

The same extract was used as for the nitrite reductase assay.

50 µl of crude enzyme solution was added to 200 µl of assay solution (50 mM Tris-HCl pH 7.5, 0.2 mM NADH, 0.2 M ammonium chloride, 1 mM calcium chloride). The reaction was incubated at 30° C. and kinetic readings taken at 340 nm every 20 seconds for 5 minutes (or until a background reading had stabilised). 10 µl of substrate (10 mM 2-oxoglutararic acid) was added to start the reaction and the absorbance monitored at 340 nm. The rate of decrease in $A_{340}$ over time was calculated and divided by the extinction coefficient for NADH (6.22) as a measure of activity.

Assay for Glutamate Dehydrogenase—Deamination Activity

Glutamate Dehydrogenase (GDH, EC 1.4.1.3) deamination catalyzes the conversion of glutamate to ammonia and 2-oxoglutarate. The enzyme assay measures the absorbance of NADH at 340 nm, which increases due to the reduction of NAD by the deaminating activity of GDH (Turano et al., 1996).

The same extract was used as for nitrite reductase assays. 50 µl of crude enzyme solution was added to 200 µl of assay solution (50 mM Tris-HCl pH 9, 0.25 mM NAD, 1 mM calcium chloride). The reaction was incubated at 30° C. and kinetic readings taken at 340 nm every 20 seconds for 5 minutes (or until a background reading had stabilised). 10 µl of substrate was added (1 M glutamic acid sodium salt) to start the reaction and the absorbance monitored at 340 nm. The rate of increase in $A_{340}$ over time was calculated and divided by the extinction coefficient for NADH (6.22) to give a measure of GDH deaminating activity.

Determination of Nitrate and Nitrite Content
Determination of Nitrate Levels in Plant Tissue In order to determine the nitrate concentration in plant tissue, salicylic acid is nitrated by the nitrate in a plant extract under highly acidic conditions. The complex formed absorbs maximally at 410 nm. The chromophore formed is 5-nitrosalicylic acid. This method is quite sensitive and is not affected by interference from chloride, nitrite or ammonium ions (Cataldo et al., 1975).

Approximately 100 mg of tissue was ground in a 1.5 ml microfuge tube with a micropestle. 300 µl of extraction buffer (50 mM Phosphate buffer pH7.5) was added and the homogenate centrifuged at 13,000 rpm in a microfuge for 15 mins at 4° C. The supernatant was removed for analysis into a fresh 1.5 ml microfuge tube. 10 µl of supernatant was mixed with 40 µl of assay solution (5% salicylic acid in sulphuric acid) and the reaction was incubated at room temperature for 20 minutes. 950 µl of 2 N sodium hydroxide was slowly added to raise the pH above 12. The samples were cooled to room temperature and the absorbance at 410 nm determined in the spectrophotometer. Standards of 1-60 µg nitrate in 10 µl aliquots were also measured for a calibration curve. A control extract consisting of extract, 40 µl of sulphuric acid (no salicylic acid) and 950 µl of 2 N sodium hydroxide was also prepared to take into account any pigmentation effects.

Determination of Nitrite Content in Plant Tissue

The nitrite content of plant tissue can be determined from either the NR assay or the NiR assay, as both assays measure the amount of nitrite in the extract at time zero. This value was calculated from the nitrite calibration curve generated during each assay, and the nitrite content of the blank assay solution subtracted from the total amount to give the nitrite content.

Chlorophyll Measurements

Two methods were employed to measure the chlorophyll content of leaf tissue. Initially an extraction protocol was the only method available, however a hand-held meter was purchased at a later date.

Chlorophyll Extraction and Quantification

Chlorophyll is insoluble in water. Chlorophyll determination is carried out in the red region of the spectrum as accessory pigments (carotenoids) absorb strongly in the blue region. It is very important to carry out extraction in the dark as chlorophyll is photo-labile, therefore all extracts must be kept wrapped in tin foil at all times.

Approximately 100 mg of tissue was ground in liquid N, 500 µl of extraction solution (80% acetone) was then added and the solution vortexed for 30 seconds. The solution was centrifuge at 2,000 rpm for 5 minutes at 4° C. The clear green supernatant was kept and wrapped in tin foil. The pellet was re-extracted with a further volume of extraction solution and added to the supernatant from the original extraction. Absorbance was measured at 652 nm $$\text{Total chlorophyll} = 27.8 \times A_{652} \text{ µg/ml}$$

Where 27.8 is the extinction coefficients of chlorophyll a and b (Hipkins and Baker, 1986).

2.14.2 In Situ Chlorophyll Content

The hand-held CCM-200 Chlorophyll Content Meter (Opti-Sciences, Inc., Hudson, N.H., USA) is battery operated and designed for rapid, non-destructive determination of chlorophyll content in intact leaf samples. The CCM-200 uses absorbance to estimate the chlorophyll content in leaf tissue. There are two wavelengths used, one wavelength falls within the chlorophyll absorbance range while the other serves to compensate for mechanical differences such as tissue thickness. The meter measures both wavelengths and calculates a CCI (chlorophyll content index) value that is proportional to the amount of chlorophyll in the sample. CCI is a relative chlorophyll value. Absolute chlorophyll content per unit area is not computed.

Amino Acid Analysis

The EZ:Faast™ kit (Phenomenex®, Macclesfield, Cheshire, UK) was used to extract and derivatise the free amino acids in leaf samples, quantification was then carried out by liquid chromatography-mass spectrometry (LC/MS: Perkin Elmer Series 200, Applied Biosystems, Warrington, Cheshire, UK). The procedure consists of a solid phase extraction of the samples; 20 µl of each sample extract along with 100 µl of internal standard were drawn slowly into a sorbent packed tip that binds amino acids while allowing interfering compounds to flow through. The flow through was discarded and 200 µl of washing solution (N-propanol) was passed slowly through the sorbent tip and discarded. Eluting medium was made fresh each day from the reagents supplied by the EZ:Faast™ kit (Sodium hydroxide and N-propanol) and 200 µl was slowly drawn partly through the tip and then ejected along with the sorbent particles into a glass vial. A 50 µl volume of chloroform was added to each sample using a glass pipette and the solution emulsified by vortexing for 10 seconds to allow the derivatised amino acids to migrate into the organic phase. The reaction was allowed to stand for 1 minute before re-emulsifying a second time. A glass pipette was used to add 100 μl of iso-octane to the solution and vortexing was repeated. The samples were allowed to stand for 1 minute before part of the organic phase was removed (about 50 μl) with a Pasteur pipette, transferred to an auto sampler vial and evaporated to dryness in a gentle stream of nitrogen. The samples were re-dissolved in 100 μl of HPLC mobile phase components (10 mM ammonium formate in water: 10 mM ammonium formate in methanol 1:2, v/v). The auto samplers were transferred to the LC/MS which had the EZ:faast AAA-MS HPLC column fitted Amino acid standards were supplied with the EZ:Faast™ kit and a calibration procedure was followed involving 10, 50 and 100 μl of amino acids standards run through the column prior to running the samples.

Statistical Analysis

All means (averages) were calculated using the Microsoft Excel (2002) software. To calculate the standard error of each sample set, the standard deviation was divided by the square root of the number of samples studied (n).

Example 1

Generation of *Arabidopsis* Nitrite Reductase (AtNiR) Constructs and Transformation of Tobacco Plants In this example the genomic AtNiR gene was isolated, cloned into a transformation construct and inserted into tobacco plants. Transgenic populations were then characterised and analysed for expression of the transgene and NiR activity.

Isolation of *A. Thaliana* NiR and Cloning into pBluescript

The full length genomic locus of *Arabidopsis* NiR is 4380 bp in length (database accession number D14824, see FIGS. 18 & 19). In the following embodiment, a genomic clone comprising the coding sequence plus introns, excluding the 3' and 5' non-translated regions present in the full length locus, was isolated. The genomic clone is 2115 bps in length and contains 3 introns and 4 exons. The exons span nucleotides 1-376, 573-928, 1010-1298, 1376-2115 bp of the genomic clone, or nucleotides 1248-1623, 1820-2175, 2257-2545 and 2623-3362 of the full length locus. The cDNA sequence (accession number BAA03561) is 1761 bp in length (see FIG. 17).

In order to isolate *Arabidopsis* NiR, *Arabidopsis thaliana* var. Columbia plants were grown from seed and the rosettes leaves of 3 week old plants were sampled and DNA extracted using Quiagen DNA Easy mini-prep extraction kit. The DNA was quantified and checked on an agarose gel before isolation of genomic *A. thaliana* NiR (AtNiR) by PCR.

Primers to the genomic *A. thaliana* NiR sequence were designed to the 5' and 3' ends of the *A. thaliana* NiR gene (primers ARFULLF and ARFULLR respectively—see above). Additional endonuclease sites were added at these ends for cloning purposes, SacI and BamHI restriction sites at the 5' end and KpnI and SacI sites at the 3' end. The genomic *A. thaliana* NiR gene was amplified by PCR using TAQ extender proof reading enzyme (Stratagene), see FIG. 1.

The amplified DNA was digested with the endonuclease SacI and ligated into the cloning vector pBluescript (pSK, Stratagene). The vector was also digested with SacI and phosphatased to prevent religation. Ligated fragments were electroporated into electro-competent *E. coli* cells. Transformed *E. coli* colonies were selected by the blue white selection method (see above). Selected colonies were cultured overnight and the DNA isolated, digested by restriction endonucleases and separated by gel electrophoresis to confirm presence of the *A. thaliana* NiR gene (AtNiR), see FIG. 2. The selected plasmids were then submitted for sequencing to Lark Technologies for verification. The received sequence data from Lark was aligned to the GenBank nucleotide sequence and showed no errors.

Binary Vector Construction of pBNPAtNiR

To integrate transgene cassettes into plant cells an appropriate plant transformation vector is required. A modified pBIN19 vector called pBINPLUS (pBNP) (Engelen et al., 1995) was used in this study. The constitutive Carnation Etched Ring Virus (CERV: Hull et al., 1986) promoter and nopaline synthase (NOS) terminator sequences were cloned into pBNP to create an acceptor vector pBNPCRVT, which would be used to accept the isolated NiR genes and reporter gene LUC (see FIG. 16). Both, pSKAtNiR and the acceptor vector pBNPCRVT were digested with the endonucleases BamHI and KpnI to isolate the AtNiR fragment and vector pBNPCRVT. The desired fragments were isolated on an agarose gel, ligated and transformed into electro competent *E. coli* cells. Isolated NiR sequences were directionally cloned into pBNPCRVT with either BamH1 and Kpn1 or BamH1 and Sac1 endonuclease sites. Luciferase (Promega Life Sciences, UK) was ligated into BamHI and Kpn1 sites.

Figure 3:
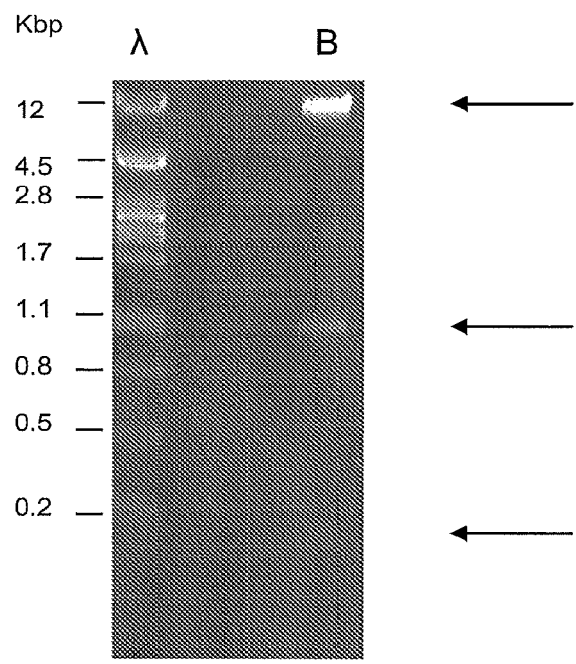
FIG. 3 shows an agarose gel image of XhoI digested fragments from pBNPAtNiR. Digest was loaded onto a 1% (w/v) agarose/TBE gel. The predicted size of the fragments were 13.124 Kbp, 1112 bp, 178 bp, λ=λ Pst1 marker, B=pBNPAtNiR.

The transformed colonies were DNA extracted, digested with endonucleases and run on an agarose gel in order to confirm that the fragments had ligated correctly and referred to as pBNPAtNiR, see FIG. 3.

Transformation of pBNPAtNiR into *Agrobacterium tumefaciens*

To allow for efficient gene transfer into tobacco, the plasmid pBNPAtNiR was electroporated into electro-competent *Agrobacterium tumefaciens* (LBA 4404). It was important to check that the binary plasmid was contained in the *Agrobacterium* following electroporation and that it was still intact before plant transformation was initiated. Therefore DNA was extracted from the transformed *A. tumefaciens* and digested with AvaI to check for the presence of the binary vector.

Figure 4:
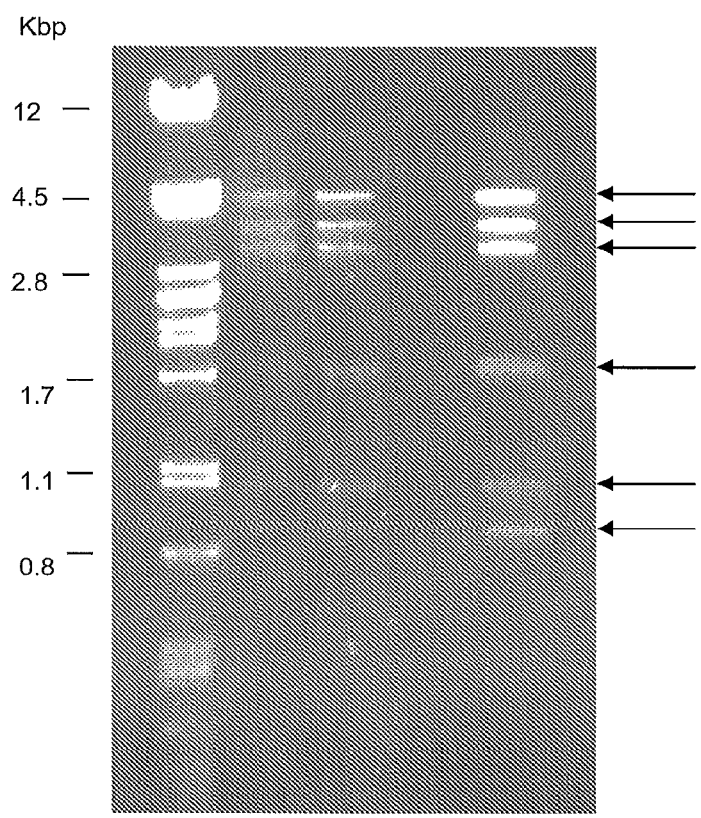
FIG. 4 shows an agarose gel image of AvaI restriction digests of *A. tumefaciens* pBNPAtNiR clones 1 and 2 compared *E. coli* pBNPAtNiR, loaded onto a 1% (w/v) agarose/TBE gel. λ=λ Pst1 marker, A1=*A. tumefaciens* pBNPAtNiR clone 1, A2=*A. tumefaciens* pBNPAtNiR clone 2, E=*E. coli* pBNPAtNiR. Identical restriction patterns indicate structural integrity has been retained.

As shown in FIG. 4, the *A. tumefaciens* contains the intact pBNPAtNiR plasmid as the fragment sizes generated (4.47 Kbp, 3.61 Kbp, 3.12 Kbp, 1.11 Kbp, 912 bp and 178 bp) from the *E. coli* and *A. tumefaciens* digests are the same.

Studies by Datta et al. (1999) showed that NiR activity increased with increasing nitrate levels in maize, and promoter studies on birch and tobacco have both identified nitrate responsive elements (Dorbe et al., 1998, Warning et al., 2000), therefore in order to stimulate NiR expression half the rice plants were put on a high nitrate feed (Phostrogen).

As a control plasmid, firefly LUC (Promega) was cloned into pBNPCRVT binary vector to produce the binary plasmid pBNPLUC. This was also transformed into *A. tumefaciens* for plant transformation.

Tobacco Transformations with pBNPAtNiR and pBNPLUC

In order to generate transgenic populations, the *Nicotiana tabacum* var. K326 plants were transformed with pBNPAtNiR, and pBNPLUC.

Screening of Transgenic Tobacco Populations

Figure 5:
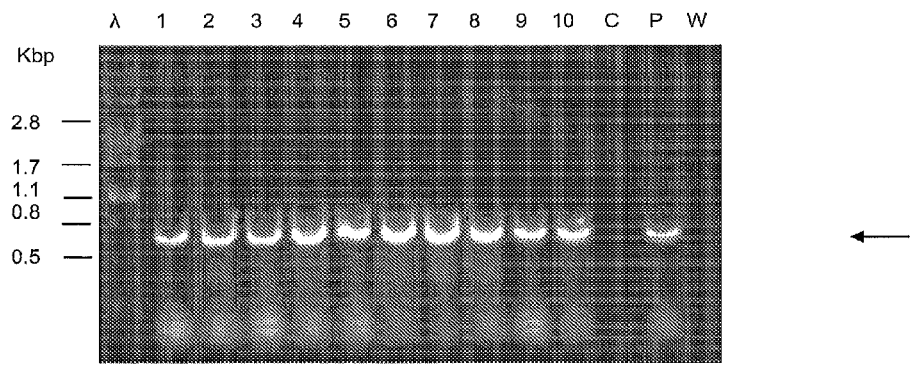
FIG. 5 shows a PCR of genomic tobacco DNA from pBNPAtNiR with primer pair ARA5R and CERV3F. PCR products were loaded onto a 1% (w/v) agarose/TBE gel. The predicted size of the product was 662 bp. λ=Pst1 DNA marker, 1-10=pBNPAtNiR lines 1-10, C=control wildtype DNA, P=plasmid DNA, W=water.
Figure 6:
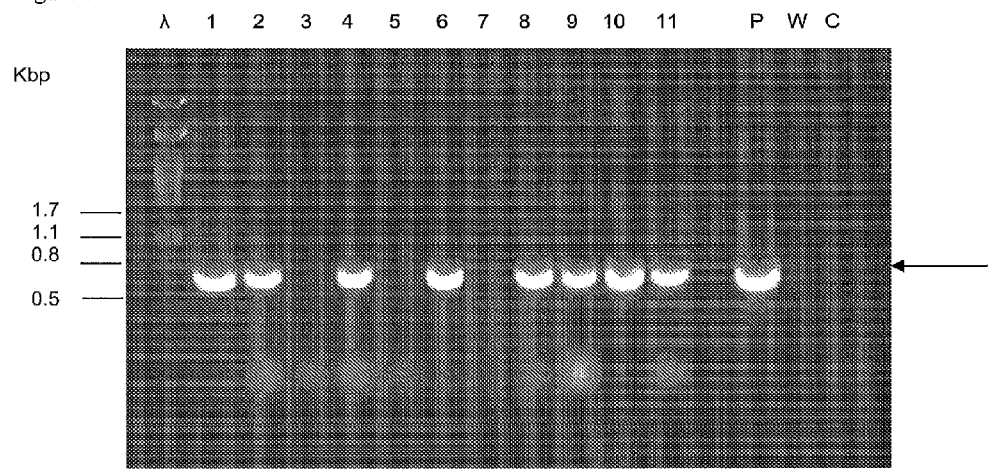
FIG. 6 shows a PCR of genomic tobacco DNA from pBNPLUC with primer pair PIVR1 and CERV3. The predicted size of the product was 703 bp. 1-11=pBNPRicNiR lines 1-11.

Primers were designed to verify the transgenic populations. The forward primer CERV3F hybridised to the 3' end of the promoter and reverse primers ARA5R and PIVR1 hybridised to the reverse strand of AtNiR and LUC sequences respectively. No amplicon was recovered from genomic DNA extracted from untransformed plants. PCR screens shown in FIGS. 5 and 6 involving the plant populations transformed with pBNPAtNiR and pBNPLUC allowed the amplification of a AtNiR 662 bp and LUC 703 bp product. Transformation efficiencies for both pBNPAtNiR and pBNPRicNiR were greater than 90%.

The plants were weaned from tissue culture and then grown in the greenhouse.

NiR Protein Expression in Transgenic Populations

Figure 7:
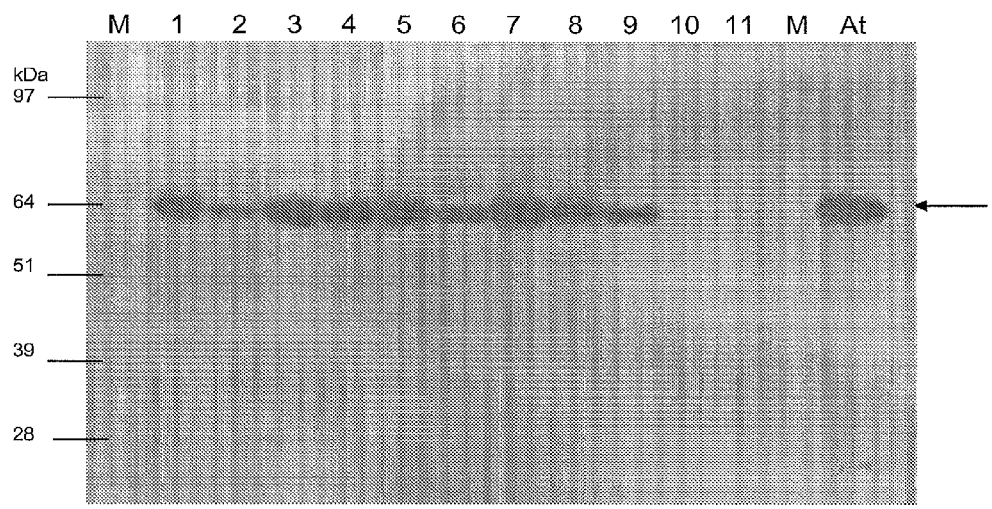
FIG. 7 shows a Western blot analysis of AtNiR plants probed with AbAtNiR. M=SeeBlue® marker, 1-11=AtNiR lines 1-11 respectively, At=*A. thaliana* leaf protein.
Figure 8:
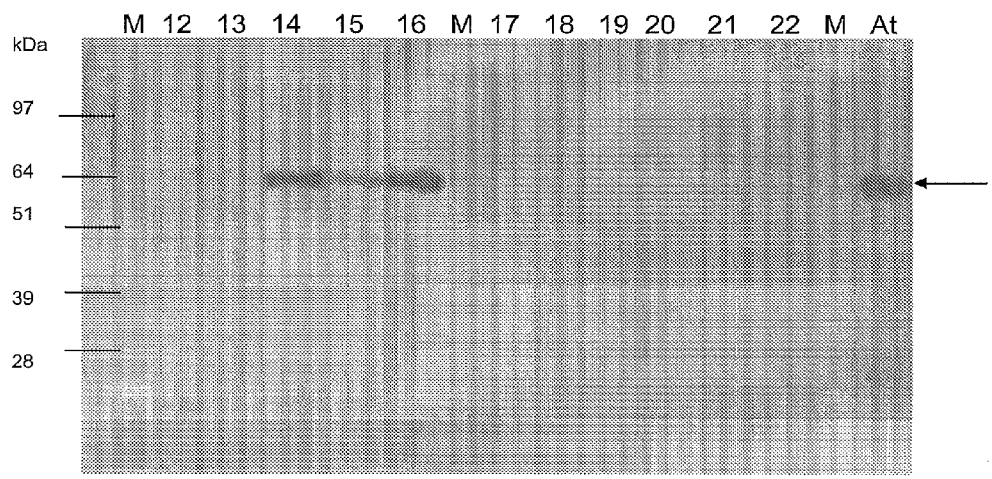
FIG. 8 shows a Western blot analysis of AtNiR plants probed with AbAtNiR. M=SeeBlue® marker, 12-22=AtNiR lines 12-12 respectively, At=*A. thaliana* leaf protein.

The transgenic plant populations of pBNPAtNiR and pBNPLUC were sampled by taking leaf 9 of plants at the pre-flowering stage (8 weeks old) which have high levels of NiR activity. The leaf material was prepared for western blot analysis, and quantified for total soluble protein using the Bradfords method, 10 μg of total leaf protein was used from each plant. The leaf protein extract from each population was probed with an antibody specific for AtNiR to determine the expression of the transgene. The western blot results clearly showed there were 12 expressing lines out of 22 pBNPAtNiR transgenic plants (see FIGS. 7 and 8). *A. thaliana* leaf protein was used as a control. The AtNiR $T_0$ lines that showed no expression were discarded. The AtNiR plants were analysed biochemically for NiR activity and were found to have increased NiR activity compared to that of the controls.

Copy Number in Primary pBNPAtNiR Transformants

The primary transformants were analysed for copy number. Primary transformants generated from calli are independent transgenic plants, but due to somaclonal variation, position and copy number effect of the transgene, they can demonstrate different phenotypes. Accordingly, it is preferably to produce homozygous $T_1$ transgenic plants for use in the present invention.

Copy number analysis was carried out using the Biorad I-cycler qPCR equipment (real-time PCR) and the absolute comparative DNA method as described above. Genomic DNA from each of the primary transgenic AtNiR lines was prepared and quantified. Primers were designed to the AtNiR gene and used in the qPCR reaction with SYBER Green as a fluorescent DNA marker. All reactions were carried out in triplicate.

The Ct (threshold cycle) value defines the cycle number at which the fluorescence, dependent on the amount of DNA present, passes a fixed threshold. The Ct values are used to calculate copy number.

Figure 9:
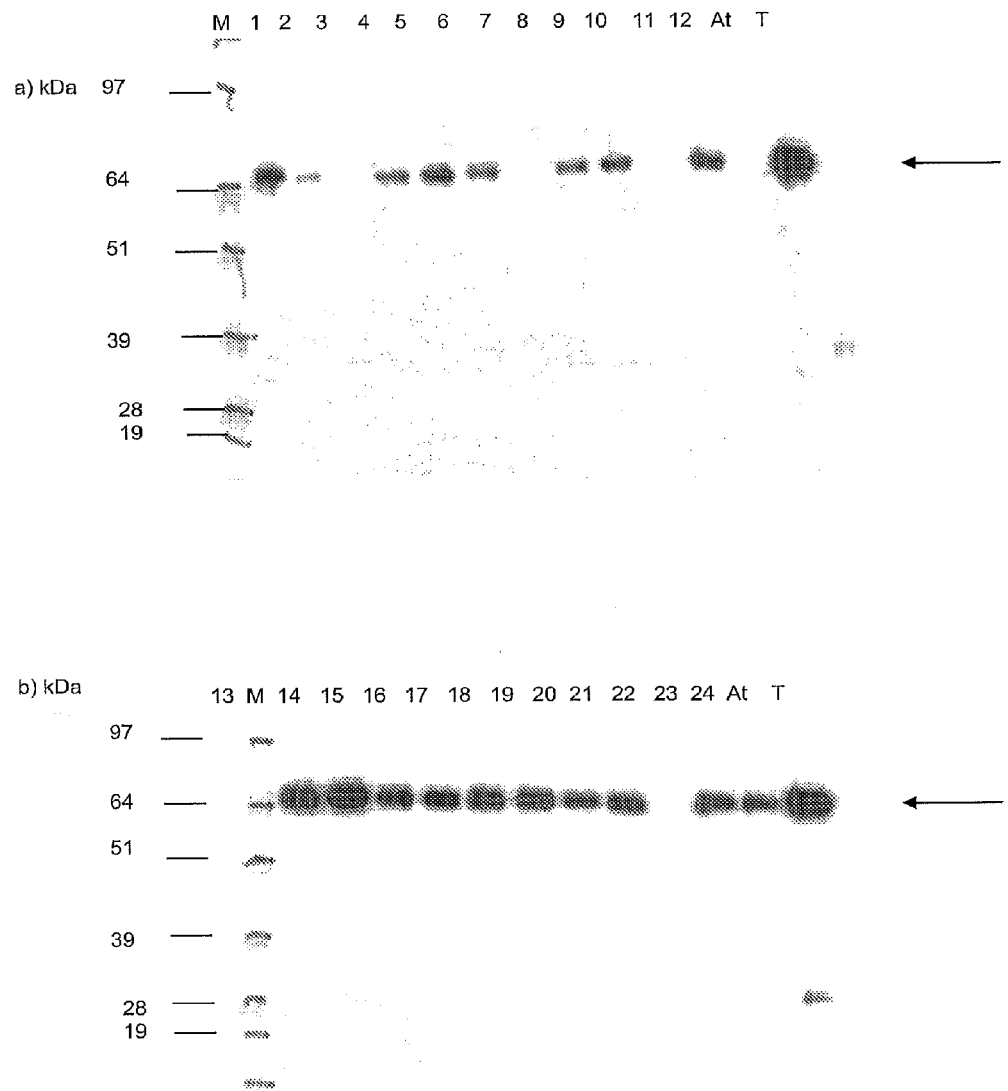
FIG. 9 shows a Western blot analysis of T1 plants from AtNiR line 9 (a) 1-12 (b) 13-24 probed with AbAtNiR.

To verify that the copy numbers calculated were correct, segregation analysis was performed on the $T_1$ populations of each line. A self fertilised single copy parent should produce a 1:2:1 ratio of homozygote, heterozygote and null offspring. This was determined by western blot analysis of the seedlings. Primary transgenic lines were self-pollinated and the seed collected, 24 seeds from each line were germinated in small modules of compost, not all lines showed 100% germination, but the majority did. The first true leaf was removed for western blot analysis after 2 weeks growth, and extracted for leaf protein. Proteins were western blotted and probed with AbAtNiR, as shown in FIG. 9. Lines showing a single copy of transgenic NiR were selected for generation of homozygous $T_1$ plants (see Example 2).

No discernable phenotype from the primary ($T_0$) transgenics was observed during the initial stages of growth and development. However, during the process of self-pollination and pod setting, a phenotype was recorded. The pBNPAtNiR lines did not appear to senesce as quickly as the control populations even though they appeared to be at the same developmental stage and were at the same chronological age (see FIG. 10).

Leaf material from the plants was sampled, leaf 5 was removed and analysed for total soluble protein and NiR activity as this leaf was clearly senescing due to the yellowing of the leaves in the control populations but not in the AtNiR lines. Results shown in FIG. 11 clearly demonstrate that NiR activity is still present in the AtNiR transgenic plants, but undetectable in the LUC population and only one plant showed activity in the WT population. There is little difference in the soluble protein between the AtNiR population and the control populations.

Example 2

Characterisation of Tobacco Plants Overexpressing *A. thaliana* Nitrite Reductase In this example, $T_1$ AtNiR transgenics and wild-type (WT) tobacco were grown on different nitrate concentrations for biochemical and molecular analysis. Older source leaves were analysed in comparison to younger sink leaves in order to assess the switch from primary N assimilation to N remobilisation and whether this transition had been altered in the transgenic lines.

Selection of Homozygous Lines

In order to generate homozygous lines for analysis, $T_1$ seed from selected AtNiR lines generated in Example 1 were planted into compost filled modules. To achieve the correct number of replicates (3 replicates in 3 blocks) for statistical analysis in a trial on 3 different levels of nitrogen, 27 homozygous plants were required from each AtNiR line. In order to obtain 27 homozygous plants per line, 160 seeds from each line were planted since only one quarter of the off-spring would be homozygous for AtNiR. Leaf tips were taken from each plant and placed in a 96-well plate and the DNA isolated using a rapid alkali treatment of plant material protocol (see above). Extracts from each plant were analysed by real-time PCR using a Bio-Rad iCycler™ to determine the copy number of the transgene. This was assessed using the comparative Ct value method.

One reaction was carried out per plant extract using the transgene primer pair At1440R and At1300F (designed to *A. thaliana* nitrite reductase) and the endogenous primer pair NRF and NRR (to *N. tabacum* nitrate reductase). On each plate a standard curve for each set of primers was produced using K326 WT tobacco and plasmid DNA. Groups of 48 plants were analysed together in one real-time PCR reaction. A relative Ct ratio of 1.5 or above was selected as a means of identifying homozygous plants, whilst any value below 1.5 was considered to be heterozygous.

Characterisation of $T_1$ NiR Treated with 3 Different Concentrations of Nitrate Following the screen for $T_1$ homozygous lines, the nitrate feeding regime required 27 homozygous individuals from each of the AtNiR lines (2, 9, 14 and 16), because there were 3 plants of each line, on each treatment (nitrate concentration), in 3 replicated blocks.

The feeding trial was set out using a randomised block design in order to assess any significant differences between the lines by statistical analysis of the results. Each block contained a complete set of treatments of 1, 5 and 10 mM nitrate, 9 homozygous individuals from the AtNiR lines and a WT control. Three plants were grown on each treatment to give a total of 45 plants in each block. This design was repeated in each block, with each block having the plants and treatments randomised within it (see FIG. 12 for schematic of design).

When the plants were sampled, the three replicates within each block were pooled, ultimately providing one set of data for each AtNiR line on each treatment from each block to compare. Analysis was performed using the ANOVA test.

Growth of Plants and Nitrate Application

The homozygous $T_1$ selected individuals were planted into 5 inch pots containing clay pebbles and stood in 7 inch saucers. Each treatment was labelled with a colour coded flag to denote which feeding regime the plant belonged to; yellow=10 mM, red=5 mM, blue=1 mM nitrate feed. The saucers were topped up each day to maintain a constant feed supply and allowed to grow for 8 weeks, until the first signs of flower buds had appeared. The differential nitrate levels on plant growth was not noticeable until week 4, when the 1 mM began to show signs of stunting due to the lack of N.

All the plants grew rapidly on 10 mM nitrate, a little slower on 5 mM and much more slowly on 1 mM nitrate.

Growth Habits of AtNiR Lines on Different Nitrate Levels

Plant growth was investigated in order to assess if increased NiR activity related to an increase in leaf biomass in the presence of varying levels of nitrate. Leaf length and plant height were measured for each of the AtNiR individuals and WT control plants. The lower source leaves (3 and 4) were sampled from each plant. For sink leaves, each plant had 2 leaves removed 10 leaves up from the first sampling position (positions 14 and 15). Measurements were taken and averaged for each set of three replicates from a block and the standard deviation calculated.

Plant height did not appear to vary significantly between the lines, the biggest variation was between the nitrate levels with 1 mM clearly causing severe stunting of the plants. This was also the case for leaf length with the difference most apparent from material grown on 1 mM nitrate. In these plants, leaf length was slightly reduced in the upper sink leaves and drastically reduced in the lower source leaves, compared to plants grown on 5 mM on 10 mM nitrate. However, no significant differences were observed between the AtNiR plants and the WT control.

Biochemical Analysis of AtNiR Lines Grown on Different Nitrate Levels

As described previously, nitrogen assimilation enzyme activities and metabolites were measured in order to determine any effect of the transgene on N metabolism when subjected to different N regimes.

The plants were sampled between 10 am and 4 pm. The same leaves were sampled as described previously, providing both sink and source leaves for analysis. Each leaf had 3 chlorophyll readings taken; one from the base, middle and tip of each leaf using a hand-held chlorophyll meter. The readings were averaged for each leaf.

Leaf samples from each set of three replicates from a block were pooled appropriately. Samples were ground in liquid nitrogen and extracted as described above for NiR, NR and GDH aminating activities, nitrite and nitrate content and total soluble protein content. As shown in FIG. 13, when total NiR and NR results were plotted against each other, AtNiR plants cluster differently compared to WT plants, indicating an effect from the AtNiR transgene.

NiR Activity and Nitrite Content

There was increased NiR activity in all the AtNiR lines compared to WT plants (see FIG. 14a), not only on the different nitrate concentrations but also in lower leaves compared to the upper leaves. This increase in activity had a P-value of <0.001, demonstrating that the introduced AtNiR gene had increased the NiR activity in the transformed lines.

The results showed a large difference in NiR activities on the 1 mM nitrate treatment compared to the other nitrogen regimes especially in the upper sink leaves. All the AtNiR transgenic lines showed a much higher NiR activity than the WT with a five-fold increase from the 5 mM and 10 mM nitrate treated plants. Nitrite content was reduced in some AtNiR transgenic lines relative to wild type plants (see FIG. 14b and Table 7), particularly at higher nitrate concentrations and in lower leaves.

NR Activity and Nitrate Content

In general the higher content of nitrate was seen in the leaves from plants treated with the higher nitrate supply (10 mM). Over all, there also appeared to be a higher nitrate content in the lower leaves than in the upper leaves. AtNiR transgenic plants tended to show a reduction in nitrate content compared to that of the WT plants (see FIG. 15 and Table 7).

Chlorophyll Content, Soluble Protein and GDH Activity

There was no change in soluble protein content between the AtNiR lines compared to the WT plants, the only difference was between nitrate supply with higher concentrations correlating with increased soluble protein. This was the same for the chlorophyll content, which did not show any statistically significant difference between the AtNiR plants and WT plants.

TABLE 7

| | Total mean values for lower leaf | | | | | Total mean values for upper leaf | | | | |
|---|---|---|---|---|---|---|---|---|---|---|
| LINE | AtNiR14 | AtNiR16 | AtNiR2 | AtNiR9 | WT | AtNiR14 | AtNiR16 | AtNiR2 | AtNiR9 | WT |
| Total soluble protein mg/g FW | 5.88 | 5.46 | 6.94 | 6.65 | 6.91 | 11.48 | 11.37 | 13.48 | 11.81 | 13.52 |
| NiR activity nmol/mg/min | 826 | 823 | 1481 | 892 | 308 | 1964 | 1631 | 1548 | 1852 | 439 |
| NR activity nmol/mg/min | 26.8 | 20.1 | 32.9 | 32.4 | 27.9 | 36.1 | 37 | 51.9 | 38.6 | 6.2 |
| Nitrite content nmol/g FW | 3.04 | 3.16 | 4.05 | 3.59 | 5.48 | 12.41 | 11.49 | 12.53 | 13.38 | 14.84 |
| Nitrate content μmol/g FW | 81.2 | 29.3 | 44.9 | 57.3 | 98.5 | 52.8 | 80.5 | 29.6 | 45.7 | 82.4 |
| GDHaminating activity nmol NADH/mg/min | 100.4 | 77.3 | 83.9 | 84.5 | 126.5 | 64.2 | 55.6 | 45.8 | 46.6 | 48.4 |
| Chlorophyll Index CCI | 7.5 | 6.69 | 9.32 | 7.78 | 6.18 | 21.94 | 21.09 | 20.76 | 22.81 | 17.96 |

Amino Acid Analysis

Free amino acids were measured in the leaf extracts used for the biochemical analysis above. Quantification of the amino acids glutamate (Glu), glutamine (Gln), aspartate (Asp), asparagine (Asn) and proline (Pro) was carried out. These five amino acids were analysed since Glu, Gln, Asp and Asn are the first 4 amino acids to be synthesised from the incorporation of ammonium ions formed from N assimilation. Pro is directly synthesised from Glu and Pro levels have been shown to be a marker of leaf age (Maslcaux et al., 2000), stress (Hare and Cress, 1999) and nitrogen status (Vaucheret et al., 1992). Therefore any differences in these amino acids between the AtNiR lines and WT plants may suggest a modification to the N assimilation pathway due to the introduction of AtNiR.

The EZ:Faast™ (Phenomenex®, Macclesfield, Cheshire, UK) method was used to derivatise the free amino acids in 20 μl of each leaf extract. Amino acids are isolated and purified from each sample and then quantification was carried out by liquid chromatography-mass spectrometry (LC/MS).

Determination of the amino acid content was performed by the Data Analysis portion of the software (Analyst® QS) controlling the LC/MS. The calculations and calibration were based on the internal standards which contained all amino acids at 200 nmoles/ml concentration. The results shown in Table 8 indicate that certain transgenic lines showed higher levels of particular amino acids. For example, lines 14 and 16 showed higher aspartate and asparagine levels than wild-type plants.

anesulfonate (EMS) causes G→A and C→T point mutations by alkylating Guanine (G). Using this method we can screen for mutations in the endogenous nitrite reductase polynucleotides.

Determination of the Optimal EMS Dosage for Seed Production

Different EMS dosages and the effect on seed set, germination and plant phenotype will be tested. This will be carried out to identify out the optimal EMS dose to find EMS induced nitrite reductase mutagenesis in Nicotiana. The optimum dose for EMS mutagenesis will be determined by treating seeds with 0, 50, 75, 100, 150, and 200 mM EMS. Briefly, seeds were imbibed for 2 hours at room temperature, treated with EMS for 4 hours at room temperature and washed 5 times for 15 minutes at room temperature. Seeds were dried overnight and sown immediately. The effects on germination, seedling lethality and plant fertility were recorded.

Production of EM-Mutagenized Plants and DNA Samples of M2 Populations to Screen for FucT Mutants In order to achieve an nominal number of mutated plants for evaluation, we will screen at least 10000 plants. Mutated seed will be sown and a DNA extraction on leaf samples of the plants will be performed, Single nucleotide polymorphisms (SNPs) within the nitrite reductase polynucleotides of the mutated plants will be evaluated, as compared to known wild-type control Nicotiana nitrite reductase polynucleotides.

Detecting EMS-Induced Point Mutations by Direct Sequencing and Single Nucleotide Polymorphism (SNP) Detection

TABLE 8

| | Total mean values for lower leaf | | | | | Total mean values for upper leaf | | | | |
|---|---|---|---|---|---|---|---|---|---|---|
| LINE | AtNiR14 | AtNiR16 | AtNiR2 | AtNiR9 | WT | AtNiR14 | AtNiR16 | AtNiR2 | AtNiR9 | WT |
| Glutamate content μmol/g FW | 1.82 | 1.84 | 1.72 | 1.85 | 1.97 | 2.79 | 2.11 | 3.09 | 2.15 | 3.24 |
| Glutamine content μmol/g FW | 2 | 2.42 | 1.73 | 1.36 | 2.56 | 5.99 | 6.89 | 8.52 | 7.48 | 10.46 |
| Aspartate content μmol/g FW | 3.1 | 1.54 | 1.21 | 1.63 | 1.52 | 6.08 | 7.19 | 2.94 | 2.9 | 2.91 |
| Asparagine content μmol/g FW | 1.37 | 1.4 | 0.6 | 1.41 | 0.9 | 8.94 | 9.46 | 8.11 | 3.81 | 4.95 |
| Proline content μmol/g FW | 1.89 | 3.29 | 2.84 | 2.77 | 6.01 | 5.97 | 9.82 | 10.51 | 9.36 | 15.1 |

All publications mentioned in this specification are incorporated herein by reference. Various modifications and variations of the described methods and products will be apparent to those skilled in the art without departing from the scope of the present invention. Although the present invention has been described in connection with specific preferred embodiments, it should be understood that the invention as claimed should not be unduly limited to such specific embodiments. Indeed, it will be apparent to those skilled in the art that various modifications of the described modes for carrying out the invention are within the scope of the following claims.

Example 3

Generation of Nicotiana tabacum Nitrite Reductase Ethyl Methanesulfonate (EMS) Mutants We will perform EMS ethyl methanesulfonate (EMS) mutagenesis to come to a selection of mutations for each endogenous nitrite reductase polynucleotide. Ethyl meth- For high throughput detection of the EMS-induced point mutations by direct sequence analysis, we will use the method described by Smits et al, (2006), Pharmacogenet. Genomics 16:159. Specific gene fragments will be amplified by PCR from DNA of leaf tissue of individual plants using gene specific primers. Each primer will carry an additional sequence at its 5' end that would allow the sequence of both strands of the resulting PCR fragment to be analyzed. The chromatograms of sequences will be analyzed for Single Nucleotide Polymorphisms (SNPs) by comparing them to wild-type Nicotiana nitrite reductase polynucleotides.

Selection of Plants

Plants that have been identified as comprising mutated nitrite reductase polynucleotide will be evaluated for total nitrite content, and plants having a reduced total nitrite content as compared to an unmutated control will be selected and more rigorously evaluated.

REFERENCES

Bendahmane A, Querci M, Kanyuka K, Baulcombe D C (2000) Agrobacterium transient expression system as a tool for the isolation of disease resistance genes: application to the Rx2 locus in potato. *The Plant Journal*, 21(1):73-81

Benfey, P. N., and Chua, N-H. (1989) Regulated genes in transgenic plants. Science 244 174-181.

Cataldo D A, Haroon M, Schrader L E, Young V L (1975) Rapid colorimetric determination of nitrate in plant tissue by nitration of salicylic acid. *Community Soil Science and Plant Analysis*, 6(1):71-80.

Cornejo M J, Luth D, Blankenship K M, Anderson O D, Blechl A E. (1993). Activity of a maize ubiquitin promoter in transgenic rice. Plant Molec. Biol. 23 567-81

Crawford N M (1995) Nitrate: nutrient and signal for plant growth. *The Plant Cell*, 7: 859-868

Crété P, Caboche M, Meyer C (1997) Nitrite reductase expression is regulated at the post transcriptional level by the nitrogen source in *Nicotiana plumbaginifolia* and *Arabidopsis thaliana*. *The Plant Journal*, 11(4):625-634

Crété P, Vaucheret H (1999) Expression and sequence requirement of nitrite reductase co-suppression. *Plant Molecular Biology*, 41:105-114

Datta R, Sharma R (1999) Temporal and spatial regulation of nitrate reductase and nitrite reductase in greening maize leaves. *Plant Science*, 144(2):77-83

Devereux J, Haeberli P, Smithies O. (1984). A comprehensive set of sequence analysis programs for the VAX. Nucleic Acids Res. 12 387-95

Djennane S, Quilleré I, Leydecker M-T, Meyer C, Chauvin J-E (2004) Expression of a deregulated tobacco nitrate reductase gene in potato increases biomass production and decreases nitrate concentration in all organs. *Planta*, 219: 884-893

Dorbe M F, Truong H N, Crete P, Vedele F D, (1998) Deletion analysis of the tobacco Nii1 promoter in *Arabidopsis thaliana*. *Plant Science*, 139:71-82

Edwards K, Johnstone C, Thompson C (1991) A simple and rapid method for the preparation of plant genomic DNA for PCR analysis. *Nucleic Acid Research*, 19(6):1349 van Engelen F A, Molthoff J W, Conner A J, Nap J-P, Pereira A, Stiekema W J (1995) pBINPLUS: an improved plant transformation vector based on pBIN19 *Transgenic Research* 4:288-290

Ellis G, Adatia I, Yazdanpanah M, Makela S K, (1998) Nitrite and Nitrate Analyses: A Clinical Biochemistry Perspective. *Clinical Biochemistry*, 31 (4):195-220

Gatz, C. (1995) Novel inducible/repressible gene expression systems. Methods in Cell Biol. 50 411-424

German M A, Kandel-Kfir M, Swarzberg D, Matsevitz T, Granot D (2003) A rapid method for the analysis of zygosity in transgenic plants. *Plant Science*, 164:183-187

Glevarec G, Bouton S, Jaspard E, Riou M-T, Cliquet J-B, Suzuki A, Limami A M (2004) Respective roles of the glutamine synthetase/glutamate synthase cycle and glutamate dehydrogenase in ammonium and amino acid metabolism during germination and post-germinative growth in the model legume *Medicaga truncatula*. *Planta*, 219:286-297

Greer F R, Shannon M (2005) Infant Methemoglobinemia: The role of dietary nitrate in food and water: A clinical report. *American Academy of Pediatrics*, 116(3):784-786

Han Y, Griffiths A, Li H, Grierson D (2004) The effect of endogenous mRNA levels on co-suppression in tomato. *FEBS Letters*, 563:123-128

Hansen G, Das A, Chilton M-D (1994) Constitutive expression of the virulence genes improves the efficiency of plant transformation by *Agrobacterium*. *Proceedings of the National Academy of Science, USA—Plant Biology* 91:7603-7607

Hansen G, Wright M (1999) Recent advances in the transformation of plants. *Trends in Plant Science*, 4:226-231

Hare P D, Cress W A, van Staden J (1999) Proline synthesis and degradation: a model system for elucidating stress-related signal transduction. *Journal of Experimental Botany*, 50(333):413-434

Hesse H, Nikiforova V, Gakière B, Hoefgen R (2004) Molecular analysis and control of cysteine biosynthesis: integration of nitrogen and sulphur metabolism. *Journal of Experimental Botany*, 55(401): 1283-1292

Hodges, M (2002) Enzyme redundancy and the importance of 2-oxoglutarate in plant ammonium assimilation. *Journal of Experimental Botany*, 53(370):905-916

Hoekema A, Hirsch P, Hooykaas P, Schilperoort R (1983) A binary plant vector strategy based on separation of vir and T-DNA region of the *Agrobacterium tumefaciens* Ti-plasmid. *Nature*, 303:179-180

Hull R, Sadler J, Longstaff M (1986) The sequence of carnation etched ring virus DNA: comparison with cauliflower mosaic virus and retroviruses. *EMBO Journal*, 5(2):3083-3090

Ioslovich I, Sdginer I (2002) Acceptable nitrate concentration of greenhouse lettuce: Tow optimal control policies. *Biosystems Engineering*, 83(2): 199-215

Isaacson C (2005) The change of the staple diet of black South Africans from sorghum to maize (corn) is the cause of the epidemic of squamous carcinoma of the esophagus. *Medical Hypotheses*, 64(3): 658-660

Kaiser W M, Huber S C (2001) Post translational regulation of nitrate reductase mechanism, physiological relevance and environmental triggers. *Journal of Experimental Botany*, 52(363):1981-1989

Kaiser W M, Weiner H, Kandlbinder A, Tsai C-B, Rockel P, Sonoda M, Planchet E (2002) Modulation of nitrate reductase: some new insights, an unusual case and a potentially important side reaction. *Journal of Experimental Botany*, 53(370):875-882

Kato C, Takahashi M, Sakamoto A, Morikawa H (2004) Differential expression of the nitrite reductase gene family in tobacco as revealed by quantitative competitive RT-PCR. *Journal of Experimental Botany*, 55 (403): 1761-1763

Klimyuk V, Carroll B, Thomas C, Jones J (1993) Alkali treatment for rapid preparation of plant material for reliable PCR analysis. *The plant Journal*, 3(3): 493-394

Kronenberger J, Lepingle A, Caboche M, Vaucheret H (1993) Cloning and expression of distinct nitrite reductases in tobacco leaves and roots. *Molecular and General Genetics*, 236:203-208

Kruse J, Hetzger I, Hänsch R, Mendel R, Walch-Lui P, Engels C, Rennenberg H (2002) Elevated pCO2 favours nitrate reduction in the roots of wild-type tobacco (*Nicotiana tabacum* cv.Gat) and significantly alters N-metabolism in transformants lacking functional nitrate reductase in the roots. *Journal of Experimental Botany*, 53(379): 2351-2367

Lea P J, Miflin B J (1974) Alternative route for nitrogen assimilation in higher plants. *Nature*, 251: 614-616

Lea P J, Miflin B J (2003) Glutamate synthase and the synthesis of glutamate in plants. *Plant Physiology and Biochemistry*, 41: 555-564

Lea U S, ten Hoopen F, Provan F, Kaiser W M, Meyer C, Lillo C (2004) Mutation of the regulatory phosphorylation site of tobacco nitrate reductase results in high nitrite excretion and NO emission from leaf and root tissue. *Planta*, 219:59-65

Lea U S, Leydecker M-T, QuiHere, Meyer C, Lillo C (2006) Posttranslational Regulation of Nitrate Reductase Strongly Affects the Levels of Free Amino Acids and Nitrate, whereas Transcriptional Regulation Has Only Minor Influence. *Plant Physiology,* 140: 1085-1094

Lee S, Munerol B, Pollard S, Youdim K, Pannala A, Kuhnle G, Dbnam E, Rice-Evans C, Spencer J (2006) The reaction of flavanols with nitrous acid protects against N-nitrosamine formation and leads to the formation of nitroso derivatives which inhibit cancer cell growth. *Free Radical Biology and Medicine,* 40: 323-334

Lillo C, Lea U S, Leydecker M-T, Meyer C (2003) Mutation of the regulatory phosphorylation site of tobacco nitrate reductase results in constitutive activation of the enzyme in vivo and nitrite accumulation. *The Plant Journal,* 35:566-573

Lillo C, Meyer C, Lea U, Provan F, Oltedal S (2004) Mechanisms and importance of post-translational regulation of nitrate reductase. *Journal of Experimental Botany,* 55(401):1275-1282

Martin A, Beastegui-Macadam X, Quilleré I, Floriot M, Valadier M-H, Pommel B, Andrieu B, Donnison I, Hirel B (2005) Nitrogen management and senescence in two maize hybrids differing in the persistence of leaf greenness: agronomic, physiological and molecular aspects. *New Phytologist,* 167:483-492

Masclaux C, Valadier M H, Brugiere N, Francois J, Hirel B (2000) Characterization of the sink/source transition in tobacco (*Nicotiana tabacum* L.) shoots in relation to nitrogen management and leaf senescence. *Planta,* 211: 510-518

Matt P, Geiger M, Walch-Liu P, Engels C, Krapp A, Stitt M (2001) The immediate cause of the diurnal changes of nitrogen metabolism in leaves of nitrate replete tobacco: a major imbalance between the rate of nitrate reduction and the rates of nitrate uptake and ammonium metabolism during the first part of the light period. *The Plant, Cell and Environment,* 24: 177-190

Miflin B, Habash D (2002) The role of glutamine synthetase and glutamate dehydrogenase in nitrogen assimilation and possibilities for improvement in the nitrogen utilization of crops. *Journal of Experimental Botany,* 53(370): 979-987

Mohr H, Schopfer P (1994) Plant Physiology. *Springer,* pp 181-184

Morikawa H, Takahashi M, Sakamoto A, Matsubara T, Arimura G, Kawamura Y, Fungag K, Gjita K, Sakurai N, Hirata T, Ide H, Nonyama N, Suzuki H (2004) Formation of unidentified nitrogen in plants: an implication for a novel nitrogen metabolism. *Planta,* 219: 14-22

Morot-Gaudry-Talarmain Y, Rockel P, Moreaux T, Quillere I, Leydecker M-T, Kaiser W M, Morot-Gaudry J F (2002) Nitrite accumulation and nitric oxide emission in relation to cellular signalling in nitrite reductase antisense tobacco. *Planta,* 215: 708-715

Needleman S B, Wunsch C D. (1970) A general method applicable to the search for similarities in the amino acid sequence of two proteins. J. Molec. Biol. 48 443-53

Odell J T, Nagy F, Chua N H. (1985). Identification of DNA sequences required for activity of the cauliflower mosaic virus 35S promoter. Nature. 313 810-2.

Ozawa K & Kawahigashi H (2005), Positional cloning of the nitrite reductase gene associated with good growth and regeneration ability of calli and establishment of a new selections system for *Agrobacterium*-mediated transformation in rice (*Oryza sativa* L.). *Plant Science* 170: 384-393.

Paine J, Shipton C, Chaggar S, Howells R, Kennedy M, Vernon G, Wright S, Hinchliffe E, Adams J, Silverstone A, Dracke R (2005) Improving the nutritional value of golden rice through increased pro-vitamin A content. *Nature Biotechnology,* 23:482-487

Rockel P, Strube F, Rockel A, Wildt J, Kaiser W M (2002) Regulation of nitric oxide (NO) production by plant nitrate reductase in vivo and in vitro. *Journal Of Experiment Botany,* 53(366): 103-110

Rothstein, S J, Sivansankar S (1998) Nitrate inducibility of gene expression using the nitrite reductase gene promoter. *Inducible Gene Expression in Plants CABI Publishing:* 83-97

Sambrook J, Frtisch E, Maniatis T (1989) Molecular Cloning: A laboratory manual. *Cold Spring Harbor Laboratory Press*

Solomonson Larry P, Barber M J (1990) Assimilatory nitrate reductase: functional properties and regulation. *Annual Review of Plant Physiology and Plant Molecular Biology,* 41: 225-253

Staaf M, Back S, Wiernik A, Wahlberg I, Long R, Young J-H (2005) Formation of tobacco-specific nitrosamines (TSNA) during air-curing: Condition and control. *Contributions to Tobacco Research,* 21(6): 321-330

Stitt M, Feil R (1999) Lateral root frequency decreases when nitrate accumulates in tobacco transformants with low nitrate reductase activity: consequences for the regulation of biomass partitioning between shoots and root. *Plant and Soil,* 215:143-153

Stöhr C (1999) Relationship of nitrate supply with growth rate, plasma membrane-bound and cytosolic nitrate reductase, and tissue nitrate content in tobacco plants. *Plant, Cell and Environment,* 22: 169-177

Stöhr C, Mäck G (2001) Diurnal changes in nitrogen assimilation of tobacco roots. *Journal of Experimental Botany,* 52 (359): 1283-1289

Swamy U, Wang M, Tripagy J N, Kim S-K, Hiraswa M, Knaff D B, Allen J P (2005) Structure of spinach nitrite reductase: Implications for multi-electron reactions by the iron-sulfur:siroheme cofactor. *Biochemistry,* 44: 16054-16063

Takahashi M, Sasaki Y, Ida S, Morikawa H (2001) Nitrite reductase gene enrichment improves assimilation of $NO_2$ in *Arabidopsis*. *Plant Physiology,* 126(2): 731-741

Tischner T (2000) Nitrate uptake review in higher and lower plants. *Plant, Cell and Environment,* 23: 1005-1024

Tobin A K, Bowsher C G (2005) Nitrogen and carbon metabolism in plastids: Evolution, integration, and coordination with reactions in the cytosol. *Advances in Botanical Research,* 42: 114-165

Turano F J, Dashner R, Upadhyaya A, Caldwell C R (1996) Purification of mitochondrial glutamate dehydrogenase from dark-grown soybean seedlings. *Plant Physiology,* 112: 1357-1364

Vaucheret H, Kronenberger J, Lepingle A, Vilaine F, Boutin J-P, Caboche M (1992) Inhibition of tobacco nitrite reductase activity by expression of antisense RNA. *The Plant Journal,* 2: 559-569

Vaucheret H, Palauqui J-C, Elmayan T, Moffatt B (1995) Molecular and genetic analysis of nitrite reductase co-suppression in transgenic tobacco plants. *Molecular and General Genetics,* 248: 311-317

Vaucheret H, Palauqui J-C, Mourrain P, Elmayan T (1997) Nitrate reductase and nitrite reductase as targets to study gene silencing phenomena in transgenic plants. *Euphytica*, 00:195-200

Vaucheret H, Béclin C, Elmayan T, Feuerback F, Godon C, Moret J-B, Mourrain P, Palauqui J-C, Vernhettes S (1998) Transgene-induced gene silencing in plants. *The Plant Journal*, 16(6): 651-659

Wang R, Okamato M, Xing X, Crawford N M (2003) Microarray analysis of the nitrate response in *Arabidopsis* roots and shoots reveals over 1000 rapidly responding genes and new linkages to glucose, trehalose-6-phosphate, iron and sulfate metabolism. *Plant Physiology*, 132: 556-567

Warner S A, Scott R, Draper J. (1993). Isolation of an asparagus intracellular PR gene (AoPR1) wound-responsive promoter by the inverse polymerase chain reaction and its characterization in transgenic tobacco. Plant J. 3 191-201.

Warning H O, Hachtel W (2000) Functional analysis of a Nitrite Reductase promoter from birch in transgenic tobacco. *Plant Science*, 1511: 41-151

Wendehenne D, Durner J, Klessig D (2004) Nitric oxide: a new player in plant signalling and defence responses. *Current Opinion in Plant Biology*, 7:449-455

Weng H, Pan A, Yang L, Zhang C, Liu Z, Zhang D (2004) Estimating number of transgene copies in transgeinc rapeseed by real-time PCR assay with HMG I/Y as an endogenous reference gene. *Plant Molecular Biology Reporter*, 22: 289-300

Wray J L, Kinghorn J R (1989) Molecular and genetic aspects of nitrate assimilation. *Oxford Science Publications*

Zhang W, McElroy D, Wu R. (1991). Analysis of rice Act1 5' region activity in transgenic rice plants. Plant Cell 3 1155-65.

The invention claimed is:

1. A transgenic *Nicotiana tabacum* plant comprising:
an exogenous gene encoding a nitrite reductase having at least 95% amino acid sequence identity to the polypeptide as defined in SEQ ID NO:3, wherein the gene encodes a protein having nitrite reductase activity and a plastid transit peptide, wherein nitrite content in the transgenic plant is reduced compared to an unmodified plant.

2. The transgenic plant according to claim 1, wherein the exogenous gene is from a plant of the genus *Arabidopsis*.

3. The transgenic *Nicotiana tabacum* plant according to claim 2, wherein the exogenous gene comprises the sequence as defined in SEQ ID NO:2.

4. The transgenic *Nicotiana tabacum* plant according to claim 1, wherein the exogenous gene encoding the nitrite reductase is associated with a promoter sequence capable of directing constitutive expression of the nitrite reductase in the transgenic plant.

5. The transgenic *Nicotiana tabacum* plant according to claim 4, wherein the promoter sequence is a constitutive promoter from Carnation Etched Ring Virus.

6. The transgenic *Nicotiana tabacum* plant according to claim 1, wherein the plant is a primary transgenic plant generated by introduction of the exogenous gene into a wild type *Nicotiana tabacum* plant.

7. The transgenic *Nicotiana tabacum* plant according to claim 6, wherein the primary transgenic plant contains a single copy of the exogenous gene.

8. The transgenic *Nicotiana tabacum* plant according to claim 1, wherein the plant is a secondary or subsequent generation transgenic plant derived from propagation of a primary transgenic plant, the primary transgenic plant being generated by introduction of the exogenous gene into a wild type plant.

9. The transgenic *Nicotiana tabacum* plant according to claim 8, wherein the second or subsequent generation transgenic plant is homozygous for the exogenous gene encoding the nitrite reductase.

10. The transgenic *Nicotiana tabacum* plant according to claim 1, wherein the nitrite reductase encoded by the exogenous gene is expressed in leaves of the transgenic plant.

11. The transgenic *Nicotiana tabacum* plant according to claim 1, wherein the nitrite content of the transgenic plant is at least 10% lower compared to a wild type *Nicotiana tabacum* plant.

* * * * *

SEQUENCE LISTING

```
<160> NUMBER OF SEQ ID NOS: 33

<210> SEQ ID NO 1
<211> LENGTH: 1761
<212> TYPE: DNA
<213> ORGANISM: Arabidopsis thaliana

<400> SEQUENCE: 1
atgacttctt tctctctcac tttcacatct cctctcctcc cttcctcctc caccaaaccc      60
aaaagatccg tccttgtcgc cgccgctcag accacagctc cggccgaatc caccgcctct     120
gttgacgcag atcgtctcga gccaagagtt gagttgaaag atggtttttt tattctcaag     180
gagaagtttc gaaaagggat caatcctcag gagaaggtta agatcgagag agagcccatg     240
aagttgttta tggagaatgg tattgaagag cttgctaaga aatctatgga agagcttgat     300
agtgaaaagt cttctaaaga tgatattgat gttagactca agtggcttgg tctctttcac     360
cgtagaaagc atcagtatgg gaagtttatg atgaggttga agttaccaaa tggtgtgact     420
acaagtgcac agactcggta tttagcgagt gtgattagga agtatggtga agatgggtgt     480
gctgatgtga ctactagaca gaattggcag atccgtggtg ttgtgttgcc tgatgtgcct     540
gagatcttga aaggtcttgc ttctgttggt ttaacgagtc ttcaaagtgg tatggataac     600
gtgaggaacc cggttgggaa tcctatagct gggattgatc cggaggagat tgttgacacg     660
aggccttaca cgaatctcct ttcgcagttt atcaccgcta attcacaagg aaaccccgat     720
ttcaccaact tgccaagaaa gtggaatgtg tgtgtggtgg ggactcatga tctctatgag     780
catccacata tcaatgattt ggcctacatg cctgctaata aagatggacg gtttggattc     840
aatttgcttg tgggaggatt ctttagtccc aaaagatgtg aagaagcgat tcctcttgat     900
gcttgggtcc ctgctgatga cgttcttcca ctctgcaaag ctgttctaga ggcttacaga     960
gatcttggaa ctcgaggaaa ccgacagaag acaagaatga tgtggcttat cgacgaactt    1020
ggtgttgaag gatttagaac tgaggtagag aagagaatgc caaatgggaa actcgagaga    1080
ggatcttcag aggatcttgt gaacaaacag tgggagagga gagactattt cggagtcaac    1140
cctcagaaac aagaaggtct tagcttcgtg gggcttcacg ttccggttgg taggctacaa    1200
gctgatgaca tggatgagct tgctcggtta gctgatacct acgggtcagg tgagctaaga    1260
ctcacagtag agcaaaacat catcatccca aatgtagaaa cctcgaaaac cgaagctttg    1320
cttcaagagc cgtttctcaa gaaccgtttc tcccctgaac catctatcct aatgaaaggc    1380
```

```
ttagttgctt gtaccggtag ccagttctgc ggacaagcga taatcgagac taagctaaga   1440
gctttaaaag tgacagaaga agtagagaga cttgtatctg tgccaagacc gataaggatg   1500
cattggacag gatgtcccaa cacttgcgga caagtccaag tagcagatat cggattcatg   1560
ggatgcttaa cacgaggcga ggaaggaaag ccagtcgagg gtgctgacgt gtacgtcggg   1620
ggacgaatag gaagtgactc gcatatcgga gagatctata agaaaggtgt tcgtgtcacg   1680
gagttggttc cattggtggc tgagattctg atcaaagaat ttggtgctgt gcctagagaa   1740
agagaagaga atgaagattg a                                            1761
```

<210> SEQ ID NO 2
<211> LENGTH: 4380
<212> TYPE: DNA
<213> ORGANISM: Arabidopsis thaliana

<400> SEQUENCE: 2

```
tctagaataa cgctaaagaa cacctatggc tctgataaca tattattaat atttacattt     60 attttatttta aagtagtcca ttcataattg cacacgacta aatgctacac aacttgtctt    120
agttgtttaa tcaagatatt tttaccttat gatattttgt gaaaaatgat acctataaaa    180
tccctaatga gcacatcaac ctttttttacc ttattatatt ttgtgaaaaa tgatatctat    240
aaaatcccta atgaccacat caaccttgaa tcttctctaa taaaccttttt ttccaaacac    300 gcactaaacc aaaaattaac atctcaagag gaaaccattt aaaaaaaaaa cagagttaga    360
ttaagatcaa caaatatagt tgaaaagaac atatgttaag caacattacc ataaattcat    420
aattagtagt gattaaaact taagaatact aaagtatgaa tatgaaaatt gttgtatttt    480
tttgtagtat gtaatatgcg gaaacttgga tgttatccta ttcattgaaa ttcatatatg    540
tatgtagtta tcatttttta aatatattaa aaaattaaaa agtaataata ctataaacat    600
tcaaattatg aaataaatat ctcatactaa tcactgctaa ttttttttcc aatgtttctc    660
tttagtattt ctctttagta tgggagtgac aaacttaata tgaaatctat ctccctacat    720
gcaaaaatcg aatctctttt attattaatg aagtgtatgg tcggtgtcaa taactaatat    780
gtcatatttt ttacagactg ttcagatatg ataaaaatag tttttttttcca accaaatggt    840 tggtcttctg agtgtatttg aaaacgacat tgaagaatta atatattttt ttttaatttt    900 agtttttttat agtacaaata ttaaaacaaa caatcctacc atatcataac atttgtaaat    960 aacatttttaa gttttgtttt gagttttaat taattttcta tgacaaaaaa atgaagtcaa   1020
tagactaagt gaatcatata gtataaataa acacaatttta aatagtttca aataaattta   1080
gaaagaataa aacaaataga aatcagaagg tgtctgtttc ctcctcgcaa catacgatca   1140
aagagaaaca acttgaccct ttacattgct caagagctca tctcttccct ctacaaaaat   1200
ggccgcacgt ctccaacctt ctcccaactc cttcttccgc catcatcatg acttctttct   1260
ctctcacttt cacatctcct ctcctccctt cctcctccac caaacccaaa agatccgtcc   1320
ttgtcgccgc cgctcagacc acagctccgg ccgaatccac cgcctctgtt gacgcagatc   1380
gtctcgagcc aagagttgag ttgaaagatg gttttttttat tctcaaggag aagtttcgaa   1440
aagggatcaa tcctcaggag aaggttaaga tcgagagaga gcccatgaag ttgtttatgg   1500
agaatggtat tgaagagctt gctaagaaat ctatggaaga gcttgatagt gaaaagtctt   1560
ctaaagatga tattgatgtt agactcaagt ggcttggtct ctttcaccgt agaaagcatc   1620
agtgtatgtt cctcctctct atcctcttcc attgacttgt gattgaactg tgtaaaggtt   1680
```

```
tcgtctttag tcttatgtgt gcttctttca atgacttgtg attaaattgg tgaccagatt    1740
gtgtaaaggt ttagtcttta ctctttatct ttagtacatt ttgatttatg agtgcttgtt    1800
gttgattttg ttgttgtaga tgggaagttt atgatgaggt tgaagttacc aaatggtgtg    1860
actacaagtg cacagactcg gtatttagcg agtgtgatta ggaagtatgg tgaagatggg    1920
tgtgctgatg tgactactag acagaattgg cagatccgtg gtgttgtgtt gcctgatgtg    1980
cctgagatct tgaaaggtct tgcttctgtt ggtttaacga gtcttcaaag tggtatggat    2040
aacgtgagga acccggttgg gaatcctata gctgggattg atccggagga gattgttgac    2100
acgaggcctt acacgaatct cctttcgcag tttatcaccg ctaattcaca aggaaacccc    2160
gatttcacca acttgtgagt tctcttttta gattgatgtt gtgtgttggt gagtgaatgg    2220
ttatgctaag atgggttttt gtttgtttgt tgtaggccaa gaaagtggaa tgtgtgtgtg    2280
gtggggactc atgatctcta tgagcatcca catatcaatg atttggccta catgcctgct    2340
aataaagatg gacggtttgg attcaatttg cttgtgggag gattctttag tcccaaaaga    2400
tgtgaagaag cgattcctct tgatgcttgg gtccctgctg atgacgttct tccactctgc    2460
aaagctgttc tagaggctta cagagatctt ggaactcgag gaaaccgaca gaagacaaga    2520
atgatgtggc ttatcgacga acttgtaagt acatgcttct tgcaatctta aattcggtat    2580
tgaagttctt ggttgttgat ttgtctgcat gaaatgtata gggtgttgaa ggatttagaa    2640
ctgaggtaga gaagagaatg ccaaatggga aactcgagag aggatcttca gaggatcttg    2700
tgaacaaaca gtgggagagg agagactatt tcggagtcaa ccctcagaaa caagaaggtc    2760
ttagcttcgt ggggcttcac gttccggttg gtaggctaca agctgatgac atggatgagc    2820
ttgctcggtt agctgatacc tacgggtcag gtgagctaag actcacagta gagcaaaaca    2880
tcatcatccc aaatgtagaa acctcgaaaa ccgaagcttt gcttcaagag ccgtttctca    2940
agaaccgttt ctcccctgaa ccatctatcc taatgaaagg cttagttgct tgtaccggta    3000
gccagttctg cggacaagcg ataatcgaga ctaagctaag agctttaaaa gtgacagaag    3060
aagtagagag acttgtatct gtgccaagac cgataaggat gcattggaca ggatgtccca    3120
acacttgcgg acaagtccaa gtagcagata tcggattcat gggatgctta acacgaggcg    3180
aggaaggaaa gccagtcgag ggtgctgacg tgtacgtcgg gggacgaata ggaagtgact    3240
cgcatatcgg agagatctat aagaaaggtg ttcgtgtcac ggagttggtt ccattggtgg    3300
ctgagattct gatcaaagaa tttggtgctg tgcctagaga aagagaagag aatgaagatt    3360
gattcaaaag ctattggatt cttaataagt caagagacct atgaatggtt ctctctctgg    3420
tttcagactt tgatacttga tacttgtatt tgtattgtgc ccataatttt gggttttgta    3480
gctctctcct ttgttgtaac ctgtaacttt gtccttggtt gttttgtaat atcttgtttt    3540
ttagtaatag tagtataatc tgatttttg tcatatattg tcttgatttc tctgtgatat    3600
ttataagaaa taaacatttg tttcttttta cctccaatat ttttgttttt gatatatcaa    3660
aagttaaggg aatagatttt aattaataaa atatattgat aatattctta aaagattatt    3720
aataaattaa attgtttttt ttttaacgtc aatttcatta atttttaaga aagagtacat    3780
ggtaaataaa gcccaacaac acaattataa agtccaacta caaacccaat agaaagatta    3840
caacttgaga ttaaactagg tttagaaggg acacgtgttt aattatctgt tcttgcgcat    3900
gttggatgag aaaagatgcc gatatgactc atcaccgcca tcttgagttg aaccgtcgat    3960
cgaaattacc tagtccgtcg ttgaaatttg aaccatcata attattaaac tctgaacac    4020
gcgacatagc aagagggcag atcagttgca aaacacactc tcctgaactg ttctacgccg    4080
```

```
gccaccaaag ctccactcaa cacaattcac gatcttaaag aggcaccttc atcgttacca    4140
gattatggtg ccaacatggg aatgaaggct ttattctttt cttactcaga attgagcaac    4200
gaatggtcta caagattctg aattagacac tcagcttcta agatttaaga tatgcaaaag    4260
gtggatcaaa actatacaaa ttaaaaaaaa aagccataaa ggctaacaga agctcgcact    4320
taggcgagaa acaaaaacc ggacaaagcc aaagacaaaa aatccggagg taaaagaaa      4380
```

<210> SEQ ID NO 3
<211> LENGTH: 586
<212> TYPE: PRT
<213> ORGANISM: Arabidopsis thaliana

<400> SEQUENCE: 3

```
Met Thr Ser Phe Ser Leu Thr Phe Thr Ser Pro Leu Leu Pro Ser Ser
1               5                   10                  15

Ser Thr Lys Pro Lys Arg Ser Val Leu Val Ala Ala Ala Gln Thr Thr
            20                  25                  30

Ala Pro Ala Glu Ser Thr Ala Ser Val Asp Ala Asp Arg Leu Glu Pro
        35                  40                  45

Arg Val Glu Leu Lys Asp Gly Phe Phe Ile Leu Lys Glu Lys Phe Arg
    50                  55                  60

Lys Gly Ile Asn Pro Gln Glu Lys Val Lys Ile Glu Arg Glu Pro Met
65                  70                  75                  80

Lys Leu Phe Met Glu Asn Gly Ile Glu Glu Leu Ala Lys Lys Ser Met
                85                  90                  95

Glu Glu Leu Asp Ser Glu Lys Ser Ser Lys Asp Asp Ile Asp Val Arg
            100                 105                 110

Leu Lys Trp Leu Gly Leu Phe His Arg Arg Lys His Gln Tyr Gly Lys
        115                 120                 125

Phe Met Met Arg Leu Lys Leu Pro Asn Gly Val Thr Thr Ser Ala Gln
    130                 135                 140

Thr Arg Tyr Leu Ala Ser Val Ile Arg Lys Tyr Gly Glu Asp Gly Cys
145                 150                 155                 160

Ala Asp Val Thr Thr Arg Gln Asn Trp Gln Ile Arg Gly Val Val Leu
                165                 170                 175

Pro Asp Val Pro Glu Ile Leu Lys Gly Leu Ala Ser Val Gly Leu Thr
            180                 185                 190

Ser Leu Gln Ser Gly Met Asp Asn Val Arg Asn Pro Val Gly Asn Pro
        195                 200                 205

Ile Ala Gly Ile Asp Pro Glu Glu Ile Val Asp Thr Arg Pro Tyr Thr
    210                 215                 220

Asn Leu Leu Ser Gln Phe Ile Thr Ala Asn Ser Gln Gly Asn Pro Asp
225                 230                 235                 240

Phe Thr Asn Leu Pro Arg Lys Trp Asn Val Cys Val Val Gly Thr His
                245                 250                 255

Asp Leu Tyr Glu His Pro His Ile Asn Asp Leu Ala Tyr Met Pro Ala
            260                 265                 270

Asn Lys Asp Gly Arg Phe Gly Phe Asn Leu Leu Val Gly Gly Phe Phe
        275                 280                 285

Ser Pro Lys Arg Cys Glu Glu Ala Ile Pro Leu Asp Ala Trp Val Pro
    290                 295                 300

Ala Asp Asp Val Leu Pro Leu Cys Lys Ala Val Leu Glu Ala Tyr Arg
305                 310                 315                 320
```

```
Asp Leu Gly Thr Arg Gly Asn Arg Gln Lys Thr Arg Met Met Trp Leu
            325                 330                 335
Ile Asp Glu Leu Gly Val Glu Gly Phe Arg Thr Glu Val Glu Lys Arg
        340                 345                 350
Met Pro Asn Gly Lys Leu Glu Arg Gly Ser Ser Glu Asp Leu Val Asn
    355                 360                 365
Lys Gln Trp Glu Arg Arg Asp Tyr Phe Gly Val Asn Pro Gln Lys Gln
370                 375                 380
Glu Gly Leu Ser Phe Val Gly Leu His Val Pro Val Gly Arg Leu Gln
385                 390                 395                 400
Ala Asp Asp Met Asp Glu Leu Ala Arg Leu Ala Asp Thr Tyr Gly Ser
                405                 410                 415
Gly Glu Leu Arg Leu Thr Val Glu Gln Asn Ile Ile Pro Asn Val
            420                 425                 430
Glu Thr Ser Lys Thr Glu Ala Leu Leu Gln Glu Pro Phe Leu Lys Asn
        435                 440                 445
Arg Phe Ser Pro Glu Pro Ser Ile Leu Met Lys Gly Leu Val Ala Cys
    450                 455                 460
Thr Gly Ser Gln Phe Cys Gly Gln Ala Ile Ile Glu Thr Lys Leu Arg
465                 470                 475                 480
Ala Leu Lys Val Thr Glu Glu Val Glu Arg Leu Val Ser Val Pro Arg
                485                 490                 495
Pro Ile Arg Met His Trp Thr Gly Cys Pro Asn Thr Cys Gly Gln Val
            500                 505                 510
Gln Val Ala Asp Ile Gly Phe Met Gly Cys Leu Thr Arg Gly Glu Glu
        515                 520                 525
Gly Lys Pro Val Glu Gly Ala Asp Val Tyr Val Gly Gly Arg Ile Gly
    530                 535                 540
Ser Asp Ser His Ile Gly Glu Ile Tyr Lys Lys Gly Val Arg Val Thr
545                 550                 555                 560
Glu Leu Val Pro Leu Val Ala Glu Ile Leu Ile Lys Glu Phe Gly Ala
                565                 570                 575
Val Pro Arg Glu Arg Glu Glu Asn Glu Asp
            580                 585

<210> SEQ ID NO 4
<211> LENGTH: 35
<212> TYPE: DNA
<213> ORGANISM: Arabidopsis thaliana

<400> SEQUENCE: 4
atcgagctcg gatccatgac ttctttctct ctcag                              35

<210> SEQ ID NO 5
<211> LENGTH: 34
<212> TYPE: DNA
<213> ORGANISM: Arabidopsis thaliana

<400> SEQUENCE: 5
gatgagctcg gatcctacct caatcttcat tctc                               34

<210> SEQ ID NO 6
<211> LENGTH: 18
<212> TYPE: DNA
<213> ORGANISM: Arabidopsis thaliana

<400> SEQUENCE: 6
```

-continued tttatcaccg ctaattca    18

<210> SEQ ID NO 7
<211> LENGTH: 17
<212> TYPE: DNA
<213> ORGANISM: Arabidopsis thaliana

<400> SEQUENCE: 7
ttaggataga tggttca    17

<210> SEQ ID NO 8
<211> LENGTH: 18
<212> TYPE: DNA
<213> ORGANISM: Arabidopsis thaliana

<400> SEQUENCE: 8
ctctttatct ttagtaca    18

<210> SEQ ID NO 9
<211> LENGTH: 18
<212> TYPE: DNA
<213> ORGANISM: Arabidopsis thaliana

<400> SEQUENCE: 9
agagaggagg aacagaca    18

<210> SEQ ID NO 10
<211> LENGTH: 18
<212> TYPE: DNA
<213> ORGANISM: Arabidopsis thaliana

<400> SEQUENCE: 10
tgttaaggca tcgaaaaa    18

<210> SEQ ID NO 11
<211> LENGTH: 16
<212> TYPE: DNA
<213> ORGANISM: Arabidopsis thaliana

<400> SEQUENCE: 11
ggattacgtc gccagt    16

<210> SEQ ID NO 12
<211> LENGTH: 16
<212> TYPE: DNA
<213> ORGANISM: Arabidopsis thaliana

<400> SEQUENCE: 12
tcttccagcg gataga    16

<210> SEQ ID NO 13
<211> LENGTH: 30
<212> TYPE: DNA
<213> ORGANISM: Arabidopsis thaliana

<400> SEQUENCE: 13
gatcagctgc acatcaacaa attttggtca    30

<210> SEQ ID NO 14
<211> LENGTH: 18
<212> TYPE: DNA
<213> ORGANISM: Arabidopsis thaliana

<400> SEQUENCE: 14
tgctgatgac gttcttcc                                                    18

<210> SEQ ID NO 15
<211> LENGTH: 16
<212> TYPE: DNA
<213> ORGANISM: Arabidopsis thaliana

<400> SEQUENCE: 15
tgcaagaagc atgtac                                                      16

<210> SEQ ID NO 16
<211> LENGTH: 21
<212> TYPE: DNA
<213> ORGANISM: Nicotiana tabacum

<400> SEQUENCE: 16
ggtctttcaa gcctcggtct g                                                21

<210> SEQ ID NO 17
<211> LENGTH: 21
<212> TYPE: DNA
<213> ORGANISM: Nicotiana tabacum

<400> SEQUENCE: 17
ggaagggaat tcgttaacca a                                                21

<210> SEQ ID NO 18
<211> LENGTH: 2277
<212> TYPE: DNA
<213> ORGANISM: Capsicum annuum

<400> SEQUENCE: 18
gaattcggct cgagcccacc tcaccccacc ttacgactac aaaaatgatc ttatttcgcc      60
attttaacca tgaccgccac gatcatcacc accctcaata atcaagaatc aactaaattc     120
ctcaattcca aatttggcga aatggcatct ttttctgtta aattttcagc aacttcttcg     180
ctgacaagtt ctaagagatt ttccaagctt catgccactc caccgcagac agtggcagta     240
cctccatctg gggcagtgga ggtagctgca gagagactag agcctagact ggaggaaaga     300
gatgggtatt gggtacttaa ggaaaagttc agaaaaggca taaatcctgc tgaaaaggcc     360
aagattgaaa aggaacctat gaaattgttc actgaaaatg gtattgaaga tattgctaag     420
atctcacttg aagagatcga aaaatctaag cttgctaagg atgatattga tgttaggctc     480
aagtggcttg gcctcttcca taggagaaag catcaatatg gacgattcat gatgcgactg     540
aagcttccaa atgggataac gacgagtgcc caaactcgat atttagcaag tgtgattagg     600
aaatatggga agatggatg tgcagatgtg actacaaggc aaaattggca gattcgtggg     660
gttgtgctac ctgatgtgcc tgagattcta aagggactgg atgaagttgg cttgaccagt     720
ctgcaaagtg gcatggacaa tgttagaaat cccgtgggga accctctggc ggggattgat     780
ccacaagaaa ttgtggacac aaggccttac gctaatttgc tatccaattt gctatcccaa     840
tatgtcactg ccaattttcg tggcaatctg tccgtgcata acttgccaag gaagtggaat     900
gtatgtgtaa tagggtcaca cgatcttttat gagcatcccc atatcaatga tcttgcctat     960
atgcctgcaa cgaaagatgg acgatttgga ttcaacctgc ttgtgggtgg attcttcagt    1020
ccgaagcgat gtgcagaggc aattcctctt gatgcatggg ttccagctga tgatgtagtc    1080
cctgtttgca aaacaatatt agaagcttat agagatcttg gtaccagagg gaacaggcag    1140

```
aaaacaagaa tgatgtggtt aattgacgaa ctgggtgttg aaggattcag ggcagaagtt    1200
gtgaagagaa tgcctcaaaa gaagctagag agagaatcca cagaggattt ggtgcagaaa    1260
caatgggaaa ggagagagta tcttggggtt aatccacaga acaggaagg ttacagcttt     1320 gttggtcttc acattccagt gggtcgtgtc caagcagatg acatggatga gcttgctcgt    1380
ttagcagaag agtatggttc aggagagctc cggctgactg ttgagcaaaa catcattatt    1440
ccgaacattg agaactcaaa gattgatgca ttgctcaatg aacctcttct gaaacagatt    1500
tcacccgatc cacctattct catgagaaat ttggtggctt gtactggtaa ccaattctgt    1560
gggcaagcca taatcgagac taaagcacgt tcaatgaaga taactgagga ggttcaacgg    1620
ctagtctctg tgactcagcc cgtgaggatg cactggactg gttgcccaaa ttcatgtgga    1680
caagttcaag ttgcagatat cggatttatg ggatgcctga caagaaagga aggaaagaca    1740
gtggaaggcg ctgatgtttt cttgggtggc agaatagga ctgactcaca cttgggagat     1800
atttataaga agtctgtccc ctgtgaagat ttggtaccaa taattgtgga cttactagtt    1860
aacaactttg gtgctgttcc aagagagaga gaagaagcag aagattaatc tcaacatttc    1920
agaatcagct cgtggctta ctcaacatag taaattggac gttgatggaa tgtgcttacc      1980
atattaagat atttccaagg tacagaactg gtggagctgt tgttggaagt tagtagaata    2040
atcagaacat gagctcttct tgacatgcta tgtgtgacat ccacgatgc aaatacttgt     2100 acttgtttca gaatattcac ccggtgtatt gttttggaaa agagctgatc caaactaaaa    2160 ggttttgaa ttgtgggatt cctaataata gatttttaa aaatgtaatt taataatcat       2220
acatttcaat ttttacctat tattatattc tttgttaaaa aaaaaaaaaa aaaaaaa        2277
```

<210> SEQ ID NO 19
<211> LENGTH: 588
<212> TYPE: PRT
<213> ORGANISM: Capsicum annuum

<400> SEQUENCE: 19

```
Met Ala Ser Phe Ser Val Lys Phe Ser Ala Thr Ser Ser Leu Thr Ser
1               5                   10                  15

Ser Lys Arg Phe Ser Lys Leu His Ala Thr Pro Pro Gln Thr Val Ala
            20                  25                  30

Val Pro Pro Ser Gly Ala Val Glu Val Ala Ala Glu Arg Leu Glu Pro
        35                  40                  45

Arg Leu Glu Glu Arg Asp Gly Tyr Trp Val Leu Lys Glu Lys Phe Arg
    50                  55                  60

Lys Gly Ile Asn Pro Ala Glu Lys Ala Lys Ile Glu Lys Glu Pro Met
65                  70                  75                  80

Lys Leu Phe Thr Glu Asn Gly Ile Glu Asp Ile Ala Lys Ile Ser Leu
                85                  90                  95

Glu Glu Ile Glu Lys Ser Lys Leu Ala Lys Asp Asp Ile Asp Val Arg
            100                 105                 110

Leu Lys Trp Leu Gly Leu Phe His Arg Arg Lys His Gln Tyr Gly Arg
        115                 120                 125

Phe Met Met Arg Leu Lys Leu Pro Asn Gly Ile Thr Thr Ser Ala Gln
    130                 135                 140

Thr Arg Tyr Leu Ala Ser Val Ile Arg Lys Tyr Gly Lys Asp Gly Cys
145                 150                 155                 160

Ala Asp Val Thr Thr Arg Gln Asn Trp Gln Ile Arg Gly Val Val Leu
                165                 170                 175
```

```
Pro Asp Val Pro Glu Ile Leu Lys Gly Leu Asp Glu Val Gly Leu Thr
            180                 185                 190

Ser Leu Gln Ser Gly Met Asp Asn Val Arg Asn Pro Val Gly Asn Pro
        195                 200                 205

Leu Ala Gly Ile Asp Pro Gln Glu Ile Val Asp Thr Arg Pro Tyr Ala
    210                 215                 220

Asn Leu Leu Ser Asn Leu Leu Ser Gln Tyr Val Thr Ala Asn Phe Arg
225                 230                 235                 240

Gly Asn Leu Ser Val His Asn Leu Pro Arg Lys Trp Asn Val Cys Val
                245                 250                 255

Ile Gly Ser His Asp Leu Tyr Glu His Pro His Ile Asn Asp Leu Ala
            260                 265                 270

Tyr Met Pro Ala Thr Lys Asp Gly Arg Phe Gly Phe Asn Leu Leu Val
        275                 280                 285

Gly Gly Phe Phe Ser Pro Lys Arg Cys Ala Glu Ala Ile Pro Leu Asp
    290                 295                 300

Ala Trp Val Pro Ala Asp Asp Val Val Pro Val Cys Lys Thr Ile Leu
305                 310                 315                 320

Glu Ala Tyr Arg Asp Leu Gly Thr Arg Gly Asn Arg Gln Lys Thr Arg
                325                 330                 335

Met Met Trp Leu Ile Asp Glu Leu Gly Val Glu Gly Phe Arg Ala Glu
            340                 345                 350

Val Val Lys Arg Met Pro Gln Lys Leu Glu Arg Glu Ser Thr Glu
        355                 360                 365

Asp Leu Val Gln Lys Gln Trp Glu Arg Arg Glu Tyr Leu Gly Val Asn
    370                 375                 380

Pro Gln Lys Gln Glu Gly Tyr Ser Phe Val Gly Leu His Ile Pro Val
385                 390                 395                 400

Gly Arg Val Gln Ala Asp Asp Met Asp Glu Leu Ala Arg Leu Ala Glu
                405                 410                 415

Glu Tyr Gly Ser Gly Glu Leu Arg Leu Thr Val Glu Gln Asn Ile Ile
            420                 425                 430

Ile Pro Asn Ile Glu Asn Ser Lys Ile Asp Ala Leu Leu Asn Glu Pro
        435                 440                 445

Leu Leu Lys Gln Ile Ser Pro Asp Pro Ile Leu Met Arg Asn Leu
    450                 455                 460

Val Ala Cys Thr Gly Asn Gln Phe Cys Gly Gln Ala Ile Ile Glu Thr
465                 470                 475                 480

Lys Ala Arg Ser Met Lys Ile Thr Glu Glu Val Gln Arg Leu Val Ser
                485                 490                 495

Val Thr Gln Pro Val Arg Met His Trp Thr Gly Cys Pro Asn Ser Cys
            500                 505                 510

Gly Gln Val Gln Val Ala Asp Ile Gly Phe Met Gly Cys Leu Thr Arg
        515                 520                 525

Lys Glu Gly Lys Thr Val Glu Gly Ala Asp Val Phe Leu Gly Gly Arg
    530                 535                 540

Ile Gly Thr Asp Ser His Leu Gly Asp Ile Tyr Lys Lys Ser Val Pro
545                 550                 555                 560

Cys Glu Asp Leu Val Pro Ile Ile Val Asp Leu Leu Val Asn Asn Phe
                565                 570                 575

Gly Ala Val Pro Arg Glu Arg Glu Glu Ala Glu Asp
            580                 585
```

```
<210> SEQ ID NO 20
<211> LENGTH: 2410
<212> TYPE: DNA
<213> ORGANISM: Oryza sativa

<400> SEQUENCE: 20
caccaccacc accaccacca ccaccaccac caccgtctcc agccatggcc tcctccgcct      60
ccctgcagcg cttcctcccc ccgtacccc acgcggcagc atcccgctgc cgccctcccg     120
gcgtccgcgc ccgccccgtg cagtcgtcga cggtgtccgc accgtcctcc tcgactccgg     180
cggcggacga ggccgtgtcg gcggagcggc tggagccgcg ggtggagcag cgggagggcc     240
ggtactgggt gctcaaggag aagtaccgga cggggctgaa cccgcaggag aaggtgaagc     300
tggggaagga gcccatgtca ttgttcatgg agggcggcat caaggagctc gccaagatgc     360
ccatggagga gatcgaggcc gacaagctct ccaaggagga catcgacgtg cggctcaagt     420
ggctcggcct cttccaccgc cgcaagcatc agtatgggcg gttcatgatg cggctgaagc     480
tgccaaacgg tgtgacgacg agcgagcaga cgaggtacct ggcgagcgtg atcgaggcgt     540
acggcaagga gggctgcgcc gacgtgacaa cccgccagaa ctggcagatc cgcggcgtca     600
cgctccccga cgtgccggcc atcctcgacg ggctcaacgc cgtcgcctc accagcctcc     660
agagcggcat ggacaacgtc cgcaaccccg tcggcaaccc gctcgccggc atcgaccccg     720
acgagatcgt cgacacgcga tcctacacca acctcctctc ctcctacatc accagcaact     780
tccagggcaa ccccaccatc accaacctgc cgaggaagtg gaacgtgtgc gtgatcgggt     840
cgcacgatct gtacgagcac ccacacatca cgacctcgc gtacatgccg gcggtgaagg     900
gcggcaagtt cgggttcaac ctcctcgtcg gcgggttcat aagccccaag aggtgggagg     960
aggcgctgcc gctcgacgcc tgggtccccg gcgacgacat catcccggtg tgcaaggccg    1020
ttctcgaggc gtaccgcgac ctcggcacca ggggcaaccg ccagaagacc cgcatgatgt    1080
ggctcatcga cgaacttgga atggaggctt ttcggtcgga ggtggagaag aggatgccga    1140
acggcgtgct ggagcgcgcg gcgccggagg acctcatcga caagaaatgg cagaggaggg    1200
actacctcgg cgtgcacccg cagaagcagg aagggatgtc ctacgtcggc ctgcacgtgc    1260
ccgtcggccg ggtgcaggcg gcggacatgt tcgagctcgc acgcctcgcc gacgagtacg    1320
gctccggcga gctccgcctc accgtggagc agaacatcgt gatcccgaac gtcaagaacg    1380
agaaggtgga ggcgctgctc tccgagccgc tgcttcagaa gttctccccg cagccgtcgc    1440
tgctgctcaa gggcctcgtc gcgtgcaccg gcaaccagtt ctgcggccag gccatcatcg    1500
agacgaagca gcgggcgctg ctggtgacgt cgcaggtgga gaagctcgtg tcggtgccc    1560
gggcggtgcg gatgcactgg accggctgcc ccaacagctg cggccaggtg caggtcgccg    1620
acatcggctt catgggctgc ctcaccaagg acagcgccgg caagatcgtt gaggcggccg    1680
acatcttcgt cggcggccgc gtcggcagcg actcgcacct cgccggcgcg tacaagaagt    1740
ccgtgccgtg cgacgagctg gcgccgatcg tcgccgacat cctggtcgag cggttcgggg    1800
ccgtgcggag ggagagggag gaggacgagg agtaggaaca cagactgggg tgttttgctt    1860
gctccggtga tctctcgccg tccttgtaaa gtagacgaca atatgccttc gcccatggca    1920
cgcttgtact gtcacgtttt ggtttgatct tgtagcccaa aagttgtgtt cattctcgtt    1980
acagtcttac agaggatgat tgattgataa ataaagaaga aacagattct gtcaagtttg    2040
gcaccgatgc gaagtacatt gccgtaggtt ctatggatcg taacctacgg atatttgggc    2100
atccgggaga agatgatcaa atggacgacg caaagccatc ggaagagtga tgaaaccaat    2160
```

-continued

```
tgtacttcat ttggcctgcg taaattgctc cctgtttgtg tgttttgacg gtggatgagc    2220
tggctgagat tggaggcaca taacaacggg agacgagaag ttccttgcag gagcaatttg    2280
gtgggctttg gtcgatgtaa acaaatttga cattgttatt gtatttgtag gccttactac    2340
ctaatgagga tacggtttgt tttggagatg aatacaatgc tgaagtgctc gacttgcgga    2400
catgccaaaa                                                           2410

<210> SEQ ID NO 21
<211> LENGTH: 596
<212> TYPE: PRT
<213> ORGANISM: Oryza sativa

<400> SEQUENCE: 21

Met Ala Ser Ser Ala Ser Leu Gln Arg Phe Leu Pro Pro Tyr Pro His
1               5                   10                  15

Ala Ala Ala Ser Arg Cys Arg Pro Pro Gly Val Arg Ala Arg Pro Val
            20                  25                  30

Gln Ser Ser Thr Val Ser Ala Pro Ser Ser Thr Pro Ala Ala Asp
        35                  40                  45

Glu Ala Val Ser Ala Glu Arg Leu Glu Pro Arg Val Glu Gln Arg Glu
    50                  55                  60

Gly Arg Tyr Trp Val Leu Lys Glu Lys Tyr Arg Thr Gly Leu Asn Pro
65                  70                  75                  80

Gln Glu Lys Val Lys Leu Gly Lys Glu Pro Met Ser Leu Phe Met Glu
                85                  90                  95

Gly Gly Ile Lys Glu Leu Ala Lys Met Pro Met Glu Glu Ile Glu Ala
            100                 105                 110

Asp Lys Leu Ser Lys Glu Asp Ile Asp Val Arg Leu Lys Trp Leu Gly
        115                 120                 125

Leu Phe His Arg Arg Lys His Gln Tyr Gly Arg Phe Met Met Arg Leu
    130                 135                 140

Lys Leu Pro Asn Gly Val Thr Thr Ser Glu Gln Thr Arg Tyr Leu Ala
145                 150                 155                 160

Ser Val Ile Glu Ala Tyr Gly Lys Glu Gly Cys Ala Asp Val Thr Thr
                165                 170                 175

Arg Gln Asn Trp Gln Ile Arg Gly Val Thr Leu Pro Asp Val Pro Ala
            180                 185                 190

Ile Leu Asp Gly Leu Asn Ala Val Gly Leu Thr Ser Leu Gln Ser Gly
        195                 200                 205

Met Asp Asn Val Arg Asn Pro Val Gly Asn Pro Leu Ala Gly Ile Asp
    210                 215                 220

Pro Asp Glu Ile Val Asp Thr Arg Ser Tyr Thr Asn Leu Leu Ser Ser
225                 230                 235                 240

Tyr Ile Thr Ser Asn Phe Gln Gly Asn Pro Thr Ile Thr Asn Leu Pro
                245                 250                 255

Arg Lys Trp Asn Val Cys Val Ile Gly Ser His Asp Leu Tyr Glu His
            260                 265                 270

Pro His Ile Asn Asp Leu Ala Tyr Met Pro Ala Val Lys Gly Gly Lys
        275                 280                 285

Phe Gly Phe Asn Leu Leu Val Gly Gly Phe Ile Ser Pro Lys Arg Trp
    290                 295                 300

Glu Glu Ala Leu Pro Leu Asp Ala Trp Val Pro Gly Asp Asp Ile Ile
305                 310                 315                 320

Pro Val Cys Lys Ala Val Leu Glu Ala Tyr Arg Asp Leu Gly Thr Arg
```

```
            325                 330                 335
Gly Asn Arg Gln Lys Thr Arg Met Met Trp Leu Ile Asp Glu Leu Gly
            340                 345                 350
Met Glu Ala Phe Arg Ser Glu Val Glu Lys Arg Met Pro Asn Gly Val
            355                 360                 365
Leu Glu Arg Ala Ala Pro Glu Asp Leu Ile Asp Lys Lys Trp Gln Arg
        370                 375                 380
Arg Asp Tyr Leu Gly Val His Pro Gln Lys Gln Glu Gly Met Ser Tyr
385                 390                 395                 400
Val Gly Leu His Val Pro Val Gly Arg Val Gln Ala Ala Asp Met Phe
                405                 410                 415
Glu Leu Ala Arg Leu Ala Asp Glu Tyr Gly Ser Gly Glu Leu Arg Leu
            420                 425                 430
Thr Val Glu Gln Asn Ile Val Ile Pro Asn Val Lys Asn Glu Lys Val
            435                 440                 445
Glu Ala Leu Leu Ser Glu Pro Leu Leu Gln Lys Phe Ser Pro Gln Pro
        450                 455                 460
Ser Leu Leu Leu Lys Gly Leu Val Ala Cys Thr Gly Asn Gln Phe Cys
465                 470                 475                 480
Gly Gln Ala Ile Ile Glu Thr Lys Gln Arg Ala Leu Leu Val Thr Ser
                485                 490                 495
Gln Val Glu Lys Leu Val Ser Val Pro Arg Ala Val Arg Met His Trp
            500                 505                 510
Thr Gly Cys Pro Asn Ser Cys Gly Gln Val Gln Val Ala Asp Ile Gly
            515                 520                 525
Phe Met Gly Cys Leu Thr Lys Asp Ser Ala Gly Lys Ile Val Glu Ala
        530                 535                 540
Ala Asp Ile Phe Val Gly Gly Arg Val Gly Ser Asp Ser His Leu Ala
545                 550                 555                 560
Gly Ala Tyr Lys Lys Ser Val Pro Cys Asp Glu Leu Ala Pro Ile Val
                565                 570                 575
Ala Asp Ile Leu Val Glu Arg Phe Gly Ala Val Arg Arg Glu Arg Glu
            580                 585                 590
Glu Asp Glu Glu
        595

<210> SEQ ID NO 22
<211> LENGTH: 2062
<212> TYPE: DNA
<213> ORGANISM: Spinacia oleracea

<400> SEQUENCE: 22
catcatcttc atcttcatct tcatcattca tagttgcaag aaacagagca accaaaaaaa      60
atggcatcac ttccagtcaa caagatcata ccatcatcaa cgacattact gtcatcgtcg     120
aacaacaaca gaagaagaaa taactcatca attcgatgcc agaaggcggt tcacccgcg     180 gcagaaacgg ctgcagtgtc gccgtctgtg acgcggcga ggctggagcc gagagtggag     240
gagagagatg ggttttgggt attgaaggag gaatttagga gtgggattaa cccagctgag     300
aaagttaaga ttgagaaaga cccaatgaag ttgtttattg aggatgggat tagtgatctt     360
gctactttgt caatggagga agttgataaa tctaagcata taaggatga tattgatgtt     420 agactcaagt ggcttggact tttccatcgc cgtaaacatc actatgggag attcatgatg     480
aggttgaagc tgccgaatgg ggtaacaacg agtgagcaga cacggtacct agcaagcgtg     540
```

```
atcaagaagt acggaaaaga tggatgtgcg gatgtaacaa caaggcaaaa ctggcaaatt      600
agaggagttg ttctgcctga tgtgccagag atcatcaaag ggctggaatc cgttggtctt      660
accagcttac agagtgggat ggacaatgta aggaaccctg taggtaaccc tcttgcaggg      720
attgaccctc atgaaattgt tgacacccga ccttttacca acctaatttc ccaatttgtc      780
actgccaatt cgcgtggaaa cctttctatt accaatctgc caaggaagtg gaatccatgt      840
gttattgggt cccatgatct ttatgagcat ccacacatca atgaccttgc ttacatgcct      900
gctacaaaga tgggaaatt cgggtttaat ttgttggttg aggattctt tagcatcaaa        960 agatgtgaag aggcaatccc actagacgct gggtctcag cagaagatgt ggttcctgta       1020
tgcaaagcta tgcttgaagc tttcagggac cttggcttta gaggaaacag gcagaagtgc      1080
agaatgatgt ggcttattga tgagcttggt atggaagcat tcaggggaga ggttgagaag      1140
agaatgcctg agcaagttct agaaagagca tcctcagaag agctggttca gaaggactgg      1200
gagagaagag aatacttagg agttcaccct cagaaacaac aaggacttag ctttgtgggt      1260
ctccacattc ctgtgggccg tctgcaagct gatgagatgg aagagttagc ccgtatagct      1320
gatgtgtatg atcagggga gctccgtctg acagtagagc agaacataat catcccaaat      1380
gttgaaaact caaagataga ttcactacta acgagcctc tgttaaaaga gcgttactcc       1440
cctgaaccac ccatcttgat gaaggggctt gtggcctgta cggggagcca attttgtgga      1500
caagccatta tcgagaccaa ggctagggca ctcaaggtga cagaagaggt acaacgacta      1560
gtgtctgtaa cacggcctgt taggatgcat tggaccgggt gtcctaatag ttgtggtcaa      1620
gtacaagtgg ctgatattgg gttcatgggt tgcatgacta gggatgagaa cggtaagcct      1680
tgtgaaggag ctgatgtgtt tgtaggagga cgtataggaa gtgactcgca tctaggagac      1740
atttacaaga aggcagtccc atgtaaagat ttggtgcctg ttgttgctga tattgatc        1800 aaccaattcg gtgctgttcc tagggagagg gaagaggcag agtagtagct agactgtttt      1860
gggtgcctgt tcttgttaac tgttatcggt attcggtaat tacttgtaat atttgcattt      1920
tttttcaagc atataattaa attgcataaa gatcccttgt atgtctgcat aacaagatac      1980
tcagttatgt aatgtcaata gcaggtttac tttgtttatt caataggcac tgtgaagggg      2040
aaagttcatt attcatttct ca                                               2062
```

<210> SEQ ID NO 23
<211> LENGTH: 594
<212> TYPE: PRT
<213> ORGANISM: Spinacia oleracea

<400> SEQUENCE: 23

```
Met Ala Ser Leu Pro Val Asn Lys Ile Ile Pro Ser Ser Thr Thr Leu
1               5                   10                  15

Leu Ser Ser Ser Asn Asn Asn Arg Arg Arg Asn Asn Ser Ser Ile Arg
            20                  25                  30

Cys Gln Lys Ala Val Ser Pro Ala Ala Glu Thr Ala Ala Val Ser Pro
        35                  40                  45

Ser Val Asp Ala Ala Arg Leu Glu Pro Arg Val Glu Glu Arg Asp Gly
    50                  55                  60

Phe Trp Val Leu Lys Glu Glu Phe Arg Ser Gly Ile Asn Pro Ala Glu
65                  70                  75                  80

Lys Val Lys Ile Glu Lys Asp Pro Met Lys Leu Phe Ile Glu Asp Gly
                85                  90                  95

Ile Ser Asp Leu Ala Thr Leu Ser Met Glu Glu Val Asp Lys Ser Lys
```

```
                100              105              110
His Asn Lys Asp Asp Ile Asp Val Arg Leu Lys Trp Leu Gly Leu Phe
            115              120              125
His Arg Arg Lys His His Tyr Gly Arg Phe Met Met Arg Leu Lys Leu
        130              135              140
Pro Asn Gly Val Thr Thr Ser Glu Gln Thr Arg Tyr Leu Ala Ser Val
145              150              155              160
Ile Lys Lys Tyr Gly Lys Asp Gly Cys Ala Asp Val Thr Thr Arg Gln
                165              170              175
Asn Trp Gln Ile Arg Gly Val Val Leu Pro Asp Val Pro Glu Ile Ile
            180              185              190
Lys Gly Leu Glu Ser Val Gly Leu Thr Ser Leu Gln Ser Gly Met Asp
        195              200              205
Asn Val Arg Asn Pro Val Gly Asn Pro Leu Ala Gly Ile Asp Pro His
    210              215              220
Glu Ile Val Asp Thr Arg Pro Phe Thr Asn Leu Ile Ser Gln Phe Val
225              230              235              240
Thr Ala Asn Ser Arg Gly Asn Leu Ser Ile Thr Asn Leu Pro Arg Lys
                245              250              255
Trp Asn Pro Cys Val Ile Gly Ser His Asp Leu Tyr Glu His Pro His
            260              265              270
Ile Asn Asp Leu Ala Tyr Met Pro Ala Thr Lys Asn Gly Lys Phe Gly
        275              280              285
Phe Asn Leu Leu Val Gly Gly Phe Phe Ser Ile Lys Arg Cys Glu Glu
    290              295              300
Ala Ile Pro Leu Asp Ala Trp Val Ser Ala Glu Asp Val Val Pro Val
305              310              315              320
Cys Lys Ala Met Leu Glu Ala Phe Arg Asp Leu Gly Phe Arg Gly Asn
                325              330              335
Arg Gln Lys Cys Arg Met Met Trp Leu Ile Asp Glu Leu Gly Met Glu
            340              345              350
Ala Phe Arg Gly Glu Val Glu Lys Arg Met Pro Glu Gln Val Leu Glu
        355              360              365
Arg Ala Ser Glu Glu Leu Val Gln Lys Asp Trp Glu Arg Arg Glu
    370              375              380
Tyr Leu Gly Val His Pro Gln Lys Gln Gly Leu Ser Phe Val Gly
385              390              395              400
Leu His Ile Pro Val Gly Arg Leu Gln Ala Asp Glu Met Glu Glu Leu
            405              410              415
Ala Arg Ile Ala Asp Val Tyr Gly Ser Gly Glu Leu Arg Leu Thr Val
        420              425              430
Glu Gln Asn Ile Ile Pro Asn Val Glu Asn Ser Lys Ile Asp Ser
    435              440              445
Leu Leu Asn Glu Pro Leu Leu Lys Glu Arg Tyr Ser Pro Glu Pro Pro
    450              455              460
Ile Leu Met Lys Gly Leu Val Ala Cys Thr Gly Ser Gln Phe Cys Gly
465              470              475              480
Gln Ala Ile Ile Glu Thr Lys Ala Arg Ala Leu Lys Val Thr Glu Glu
                485              490              495
Val Gln Arg Leu Val Ser Val Thr Arg Pro Val Arg Met His Trp Thr
            500              505              510
Gly Cys Pro Asn Ser Cys Gly Gln Val Gln Val Ala Asp Ile Gly Phe
        515              520              525
```

```
Met Gly Cys Met Thr Arg Asp Glu Asn Gly Lys Pro Cys Glu Gly Ala
        530                 535                 540

Asp Val Phe Val Gly Gly Arg Ile Gly Ser Asp Ser His Leu Gly Asp
545                 550                 555                 560

Ile Tyr Lys Lys Ala Val Pro Cys Lys Asp Leu Val Pro Val Ala
                565                 570                 575

Glu Ile Leu Ile Asn Gln Phe Gly Ala Val Pro Arg Glu Arg Glu Glu
            580                 585                 590

Ala Glu

<210> SEQ ID NO 24
<211> LENGTH: 1839
<212> TYPE: DNA
<213> ORGANISM: Nicotiana tabacum

<400> SEQUENCE: 24
tttctattaa atttctggca ccttcattgc caaatccagc tagattttcc aagaatgctg      60
tcaagctcca cgcaactccg ccgtctgtgg cagcgccgcc agctggtgct ccagaggttg     120
ctgctgagag gctagaaccc agagttgagg aaaaagatgg ttattggata ctcaaggagc     180
agtttagaaa aggcataaat cctcaagaaa aggtcaagat tgagaagcaa cctatgaagt     240
tgttcatgga aaatggtatt gaagagcttg ctaagatacc cattgaagag atagatcagt     300
ccaagcttac taaggatgat attgatgtta ggcttaagtg gcttggcctc ttccatagga     360
gaaagaacca atatgggcgg ttcatgatga gattgaagct tccaaatgga gtaacaacga     420
gtgcacagac tcgatacttg gcgagtgtga taggaaaata cgggaagaa ggatgtgctg     480 atattacaac gaggcaaaat tggcagattc gtggagttgt actgcctgat gtgcccgaga     540
tactaaaggg actagcagaa gttgggttga ccagtttgca gagtggcatg acaatgtca     600 ggaatccagt aggaaatcct cttgctggaa ttgatccaga agaaatagta gacacagggc     660
cttacactaa tttgctctcc caatttatca ctggcaattc acgaggcaat cccgcagttt     720
ctaacttgcc aaggaagtgg aatccgtgcg tagtaggctc tcatgatctt tatgaacatc     780
cccatatcaa cgatctcgcg tacatgcctg ccacgaaaga tggacgattt ggattcaacc     840
tgcttgtggg tgggttcttc agcgcaaaaa gatgtgatga ggcaattcct cttgatgcat     900
gggttccagc tgatgatgtt gttccggttt gcaaagcaat actggaagct ttagagatc     960 ttggtttcag agggaacaga cagaaatgta gaatgatgtg ttaatcgat gaactgggtg    1020 tagaaggatt cagggcagag gtcgagaaga gaatgccaca gcaagagcta gagagagcat    1080
ctccagagga cttggttcag aaacaatggg aagaagaga ttatcttggt gtacatccac    1140
aaaaacaaga aggctacagc tttattggtc ttcacattcc agtgggtcgt gttcaagcag    1200
acgatatgga tgagctagct cgtttagctg atgagtatgg ttcaggagag atccggctta    1260
ctgtggaaca aaacattatt attcccaaca ttgagaactc aaagattgag gcactgctca    1320
aagagcctgt tctgagcaca ttttcacctg atccacctat tctcatgaaa ggtttagtgg    1380
cttgtactgg taaccagttt tgtggacaag ccataatcga gactaaagct cgttccctga    1440
tgataactga agaggttcaa cggcaagttt ctttgacacg gccagtgagg atgcactgga    1500
caggctgccc gaatacgtgt gcacaagttc aagttgcgga cattggattc atgggatgcc    1560
tgactagaga taagaatgga aagactgtgg aaggcgccga tgttttctta ggaggcagaa    1620
tagggagtga ttcacatttg ggagaagtat ataagaaggc tgttccttgt gatgatttgg    1680
```

```
taccacttgt tgtggactta ctagttaaca actttggtgc agttccacga gaaagagaag    1740
aaacagaaga ctaataaaat ttagaatagt tggtgatttt gctgtgttca taacatgtaa    1800
tgtatgataa atcaatgcaa acatttctac ctacgtgag                           1839
```

<210> SEQ ID NO 25
<211> LENGTH: 583
<212> TYPE: PRT
<213> ORGANISM: Nicotiana tabacum

<400> SEQUENCE: 25

| Ser | Ile | Lys | Phe | Leu | Ala | Pro | Ser | Leu | Pro | Asn | Pro | Ala | Arg | Phe | Ser |
|---|---|---|---|---|---|---|---|---|---|---|---|---|---|---|---|
| 1 | | | | 5 | | | | | 10 | | | | | 15 | |

| Lys | Asn | Ala | Val | Lys | Leu | His | Ala | Thr | Pro | Pro | Ser | Val | Ala | Ala | Pro |
|---|---|---|---|---|---|---|---|---|---|---|---|---|---|---|---|
| | | | 20 | | | | | 25 | | | | | 30 | | |

| Pro | Ala | Gly | Ala | Pro | Glu | Val | Ala | Ala | Glu | Arg | Leu | Glu | Pro | Arg | Val |
|---|---|---|---|---|---|---|---|---|---|---|---|---|---|---|---|
| | | 35 | | | | | 40 | | | | | 45 | | | |

| Glu | Glu | Lys | Asp | Gly | Tyr | Trp | Ile | Leu | Lys | Glu | Gln | Phe | Arg | Lys | Gly |
|---|---|---|---|---|---|---|---|---|---|---|---|---|---|---|---|
| | 50 | | | | | 55 | | | | | 60 | | | | |

| Ile | Asn | Pro | Gln | Glu | Lys | Val | Lys | Ile | Glu | Lys | Gln | Pro | Met | Lys | Leu |
|---|---|---|---|---|---|---|---|---|---|---|---|---|---|---|---|
| 65 | | | | | 70 | | | | | 75 | | | | | 80 |

| Phe | Met | Glu | Asn | Gly | Ile | Glu | Glu | Leu | Ala | Lys | Ile | Pro | Ile | Glu | Glu |
|---|---|---|---|---|---|---|---|---|---|---|---|---|---|---|---|
| | | | | 85 | | | | | 90 | | | | | 95 | |

| Ile | Asp | Gln | Ser | Lys | Leu | Thr | Lys | Asp | Asp | Ile | Asp | Val | Arg | Leu | Lys |
|---|---|---|---|---|---|---|---|---|---|---|---|---|---|---|---|
| | | | 100 | | | | | 105 | | | | | 110 | | |

| Trp | Leu | Gly | Leu | Phe | His | Arg | Arg | Lys | Asn | Gln | Tyr | Gly | Arg | Phe | Met |
|---|---|---|---|---|---|---|---|---|---|---|---|---|---|---|---|
| | | 115 | | | | | 120 | | | | | 125 | | | |

| Met | Arg | Leu | Lys | Leu | Pro | Asn | Gly | Val | Thr | Thr | Ser | Ala | Gln | Thr | Arg |
|---|---|---|---|---|---|---|---|---|---|---|---|---|---|---|---|
| | 130 | | | | | 135 | | | | | 140 | | | | |

| Tyr | Leu | Ala | Ser | Val | Ile | Arg | Lys | Tyr | Gly | Lys | Glu | Gly | Cys | Ala | Asp |
|---|---|---|---|---|---|---|---|---|---|---|---|---|---|---|---|
| 145 | | | | | 150 | | | | | 155 | | | | | 160 |

| Ile | Thr | Thr | Arg | Gln | Asn | Trp | Gln | Ile | Arg | Gly | Val | Val | Leu | Pro | Asp |
|---|---|---|---|---|---|---|---|---|---|---|---|---|---|---|---|
| | | | | 165 | | | | | 170 | | | | | 175 | |

| Val | Pro | Glu | Ile | Leu | Lys | Gly | Leu | Ala | Glu | Val | Gly | Leu | Thr | Ser | Leu |
|---|---|---|---|---|---|---|---|---|---|---|---|---|---|---|---|
| | | | 180 | | | | | 185 | | | | | 190 | | |

| Gln | Ser | Gly | Met | Asp | Asn | Val | Arg | Asn | Pro | Val | Gly | Asn | Pro | Leu | Ala |
|---|---|---|---|---|---|---|---|---|---|---|---|---|---|---|---|
| | | 195 | | | | | 200 | | | | | 205 | | | |

| Gly | Ile | Asp | Pro | Glu | Glu | Ile | Val | Asp | Thr | Gly | Pro | Tyr | Thr | Asn | Leu |
|---|---|---|---|---|---|---|---|---|---|---|---|---|---|---|---|
| | 210 | | | | | 215 | | | | | 220 | | | | |

| Leu | Ser | Gln | Phe | Ile | Thr | Gly | Asn | Ser | Arg | Gly | Asn | Pro | Ala | Val | Ser |
|---|---|---|---|---|---|---|---|---|---|---|---|---|---|---|---|
| 225 | | | | | 230 | | | | | 235 | | | | | 240 |

| Asn | Leu | Pro | Arg | Lys | Trp | Asn | Pro | Cys | Val | Val | Gly | Ser | His | Asp | Leu |
|---|---|---|---|---|---|---|---|---|---|---|---|---|---|---|---|
| | | | | 245 | | | | | 250 | | | | | 255 | |

| Tyr | Glu | His | Pro | His | Ile | Asn | Asp | Leu | Ala | Tyr | Met | Pro | Ala | Thr | Lys |
|---|---|---|---|---|---|---|---|---|---|---|---|---|---|---|---|
| | | | 260 | | | | | 265 | | | | | 270 | | |

| Asp | Gly | Arg | Phe | Gly | Phe | Asn | Leu | Leu | Val | Gly | Gly | Phe | Phe | Ser | Ala |
|---|---|---|---|---|---|---|---|---|---|---|---|---|---|---|---|
| | | 275 | | | | | 280 | | | | | 285 | | | |

| Lys | Arg | Cys | Asp | Glu | Ala | Ile | Pro | Leu | Asp | Ala | Trp | Val | Pro | Ala | Asp |
|---|---|---|---|---|---|---|---|---|---|---|---|---|---|---|---|
| | 290 | | | | | 295 | | | | | 300 | | | | |

| Asp | Val | Val | Pro | Val | Cys | Lys | Ala | Ile | Leu | Glu | Ala | Phe | Arg | Asp | Leu |
|---|---|---|---|---|---|---|---|---|---|---|---|---|---|---|---|
| 305 | | | | | 310 | | | | | 315 | | | | | 320 |

| Gly | Phe | Arg | Gly | Asn | Arg | Gln | Lys | Cys | Arg | Met | Met | Trp | Leu | Ile | Asp |
|---|---|---|---|---|---|---|---|---|---|---|---|---|---|---|---|
| | | | | 325 | | | | | 330 | | | | | 335 | |

| Glu | Leu | Gly | Val | Glu | Gly | Phe | Arg | Ala | Glu | Val | Glu | Lys | Arg | Met | Pro |
|---|---|---|---|---|---|---|---|---|---|---|---|---|---|---|---|
| | | | 340 | | | | | 345 | | | | | 350 | | |

```
Gln Gln Glu Leu Glu Arg Ala Ser Pro Glu Asp Leu Val Gln Lys Gln
        355                 360                 365

Trp Glu Arg Arg Asp Tyr Leu Gly Val His Pro Gln Lys Gln Glu Gly
370                 375                 380

Tyr Ser Phe Ile Gly Leu His Ile Pro Val Gly Arg Val Gln Ala Asp
385                 390                 395                 400

Asp Met Asp Glu Leu Ala Arg Leu Ala Asp Glu Tyr Gly Ser Gly Glu
                405                 410                 415

Ile Arg Leu Thr Val Glu Gln Asn Ile Ile Pro Asn Ile Glu Asn
                420                 425                 430

Ser Lys Ile Glu Ala Leu Leu Lys Glu Pro Val Leu Ser Thr Phe Ser
            435                 440                 445

Pro Asp Pro Pro Ile Leu Met Lys Gly Leu Val Ala Cys Thr Gly Asn
        450                 455                 460

Gln Phe Cys Gly Gln Ala Ile Ile Glu Thr Lys Ala Arg Ser Leu Met
465                 470                 475                 480

Ile Thr Glu Glu Val Gln Arg Gln Val Ser Leu Thr Arg Pro Val Arg
                485                 490                 495

Met His Trp Thr Gly Cys Pro Asn Thr Cys Ala Gln Val Gln Val Ala
                500                 505                 510

Asp Ile Gly Phe Met Gly Cys Leu Thr Arg Asp Lys Asn Gly Lys Thr
            515                 520                 525

Val Glu Gly Ala Asp Val Phe Leu Gly Gly Arg Ile Gly Ser Asp Ser
        530                 535                 540

His Leu Gly Glu Val Tyr Lys Lys Ala Val Pro Cys Asp Asp Leu Val
545                 550                 555                 560

Pro Leu Val Val Asp Leu Leu Val Asn Asn Phe Gly Ala Val Pro Arg
                565                 570                 575

Glu Arg Glu Glu Thr Glu Asp
            580

<210> SEQ ID NO 26
<211> LENGTH: 1764
<212> TYPE: DNA
<213> ORGANISM: Nicotiana tabacum

<400> SEQUENCE: 26
atggcatctt tttctgttaa attctcagca acttcattgc caaatcctaa cagattttcc      60
aggactgcta agcttcatgc aacaccgccg cagacggtgg cagtaccacc atctggggag     120
gcggagatag cttccgagag gctagagcct agagtagagg aaaaagatgg gtattgggta     180
ctcaaggaaa aattcagaca agggataaat ccagctgaaa aggccaagat tgagaaagaa     240
ccaatgaaat tatttatgga aaatggtatt gaagatcttg ctaagatctc acttgaagag     300
atcgaagggt ctaagcttac taaagatgat attgatgtta ggctcaagtg gcttggcctt     360
ttccatagga gaaagcatca ttatggccga ttcatgatgc gattgaagct tccaaatggg     420
gtaacaacga gtgcccaaac tcgatactta gccagtgtga taggaaaata tggaaaagat     480
ggatgtggtg atgtgactac aaggcaaaat tggcagattc gcggggttgt actacctgat     540
gtacccgaga ttctaaaggg actggatgaa gttggcttga ccagtctgca aagtggcatg     600
gacaacgttc gaaatccggt gggaaatcct ctggcgggga ttgatccaca tgaaattgta     660
gacacaaggc cttacactaa tttgctctcc caatatgtta ctgccaattt cgtggcaat      720 ccggctgtta ctaacttgcc aaggaagtgg aatgtatgtg taatagggtc acatgatctt     780
```

```
tatgagcatc cccatatcaa tgatcttgcc tatatgccgg catcaaaaga tggacgattt    840
ggattcaacc tgcttgtggg tggattcttc agtccgaagc gatgtgcaga ggcagttcct    900
ctagatgcat gggttccagc tgatgacgtg gtccctgttt gcaaagcaat attagaagct    960
tatagagatc ttggtaccag agggaacagg caaaaaacaa gaatgatgtg gttagttgat   1020
gaactgggcg ttgaaggatt cagggcagag gtcgtaaaga gaatgcctca acaaaagcta   1080
gatagagaat caacagagga cttggttcaa aacaatggg aaaggagaga ataccttggc   1140
gtgcatccgc agaaacaaga aggatacagc tttgttggcc ttcacattcc ggtaggtcgt   1200
gtccaagcag atgacatgga cgagctagct cgtttagcgg ataactatgg ttcaggagag   1260
ctccggttga ctgttgaaca gaacatcatt attcccaacg ttgagaactc aaagatcgag   1320
tcattgctca atgagcctct cttaaagaac agattttcga ccaatccacc tattctcatg   1380
aaaaatctgg tggcttgtac tggtaaccaa ttttgcgggc aagccataat tgagactaaa   1440
gcgcgttcca tgaagataac tgaggaggta caacgactag tttctgtgac aaagccggtg   1500
aggatgcatt ggactggttg cccgaattca tgtggacaag ttcaagtcgc ggatattgga   1560
tttatgggat gcttgacaag aaaagaaggg aaaactgtag aaggtgctga tgtttatttg   1620
ggaggcagaa tagggagtga ctcacatttg ggagatgttt ataagaaatc agtaccttgt   1680
gaggatttgg tgccaataat tgtggactta ctagttaaca actttggtgc tgttccaaga   1740
gaaagagaag aagcagaaga ttaa                                          1764

<210> SEQ ID NO 27
<211> LENGTH: 587
<212> TYPE: PRT
<213> ORGANISM: Nicotiana tabacum

<400> SEQUENCE: 27

Met Ala Ser Phe Ser Val Lys Phe Ser Ala Thr Ser Leu Pro Asn Pro
1               5                   10                  15

Asn Arg Phe Ser Arg Thr Ala Lys Leu His Ala Thr Pro Pro Gln Thr
            20                  25                  30

Val Ala Val Pro Pro Ser Gly Glu Ala Glu Ile Ala Ser Glu Arg Leu
        35                  40                  45

Glu Pro Arg Val Glu Glu Lys Asp Gly Tyr Trp Val Leu Lys Glu Lys
    50                  55                  60

Phe Arg Gln Gly Ile Asn Pro Ala Glu Lys Ala Lys Ile Lys Glu
65                  70                  75                  80

Pro Met Lys Leu Phe Met Glu Asn Gly Ile Glu Asp Leu Ala Lys Ile
                85                  90                  95

Ser Leu Glu Glu Ile Glu Gly Ser Lys Leu Thr Lys Asp Asp Ile Asp
            100                 105                 110

Val Arg Leu Lys Trp Leu Gly Leu Phe His Arg Lys His His Tyr
        115                 120                 125

Gly Arg Phe Met Met Arg Leu Lys Leu Pro Asn Gly Val Thr Thr Ser
    130                 135                 140

Ala Gln Thr Arg Tyr Leu Ala Ser Val Ile Arg Lys Tyr Gly Lys Asp
145                 150                 155                 160

Gly Cys Gly Asp Val Thr Thr Arg Gln Asn Trp Gln Ile Arg Gly Val
                165                 170                 175

Val Leu Pro Asp Val Pro Glu Ile Leu Lys Gly Leu Asp Glu Val Gly
            180                 185                 190
```

Leu Thr Ser Leu Gln Ser Gly Met Asp Asn Val Arg Asn Pro Val Gly
            195                 200                 205

Asn Pro Leu Ala Gly Ile Asp Pro His Glu Ile Val Asp Thr Arg Pro
        210                 215                 220

Tyr Thr Asn Leu Leu Ser Gln Tyr Val Thr Ala Asn Phe Arg Gly Asn
225                 230                 235                 240

Pro Ala Val Thr Asn Leu Pro Arg Lys Trp Asn Val Cys Val Ile Gly
            245                 250                 255

Ser His Asp Leu Tyr Glu His Pro His Ile Asn Asp Leu Ala Tyr Met
            260                 265                 270

Pro Ala Ser Lys Asp Gly Arg Phe Gly Phe Asn Leu Leu Val Gly Gly
            275                 280                 285

Phe Phe Ser Pro Lys Arg Cys Ala Glu Ala Val Pro Leu Asp Ala Trp
290                 295                 300

Val Pro Ala Asp Asp Val Pro Val Cys Lys Ala Ile Leu Glu Ala
305                 310                 315                 320

Tyr Arg Asp Leu Gly Thr Arg Gly Asn Arg Gln Lys Thr Arg Met Met
                325                 330                 335

Trp Leu Val Asp Glu Leu Gly Val Glu Gly Phe Arg Ala Glu Val Val
            340                 345                 350

Lys Arg Met Pro Gln Gln Lys Leu Asp Arg Glu Ser Thr Glu Asp Leu
            355                 360                 365

Val Gln Lys Gln Trp Glu Arg Arg Glu Tyr Leu Gly Val His Pro Gln
    370                 375                 380

Lys Gln Glu Gly Tyr Ser Phe Val Gly Leu His Ile Pro Val Gly Arg
385                 390                 395                 400

Val Gln Ala Asp Asp Met Asp Glu Leu Ala Arg Leu Ala Asp Asn Tyr
                405                 410                 415

Gly Ser Gly Glu Leu Arg Leu Thr Val Glu Gln Asn Ile Ile Ile Pro
            420                 425                 430

Asn Val Glu Asn Ser Lys Ile Glu Ser Leu Leu Asn Glu Pro Leu Leu
            435                 440                 445

Lys Asn Arg Phe Ser Thr Asn Pro Pro Ile Leu Met Lys Asn Leu Val
450                 455                 460

Ala Cys Thr Gly Asn Gln Phe Cys Gly Gln Ala Ile Ile Glu Thr Lys
465                 470                 475                 480

Ala Arg Ser Met Lys Ile Thr Glu Glu Val Gln Arg Leu Val Ser Val
                485                 490                 495

Thr Lys Pro Val Arg Met His Trp Thr Gly Cys Pro Asn Ser Cys Gly
            500                 505                 510

Gln Val Gln Val Ala Asp Ile Gly Phe Met Gly Cys Leu Thr Arg Lys
    515                 520                 525

Glu Gly Lys Thr Val Glu Gly Ala Asp Val Tyr Leu Gly Gly Arg Ile
530                 535                 540

Gly Ser Asp Ser His Leu Gly Asp Val Tyr Lys Ser Val Pro Cys
545                 550                 555                 560

Glu Asp Leu Val Pro Ile Ile Val Asp Leu Leu Val Asn Asn Phe Gly
                565                 570                 575

Ala Val Pro Arg Glu Arg Glu Ala Glu Asp
            580                 585

<210> SEQ ID NO 28
<211> LENGTH: 1764
<212> TYPE: DNA

<213> ORGANISM: Nicotiana tabacum

<400> SEQUENCE: 28

```
atggcatctt tttctattaa atttctggca ccttcattgc caaatccagc tagattttcc      60
aagaatgctg tcaagctcca tgcaacaccg ccgtctgtgg cagcgccgcc aactggtgct     120
ccagaggttg ctgctgagag gctagaaccc agagttgagg aaaaagatgg ttattggata     180
ctgaaagagc agtttagaaa aggcataaat cctcaagaaa aggtcaagat tgagaaggaa     240
cctatgaagt tgttcatgga aatggtatt gaagagcttg ctaagatacc cattgaagag      300
atagatcagt ccaagcttac taaggatgat attgatgtta ggcttaagtg gcttggcctc     360
ttccatagga gaaagaatca atatgggcgg ttcatgatga gattgaagct tccaaatgga     420
gtaacaacga gtgcacagac tcgatactta gcgagtgtga taggaaaata cgggaaggaa     480
ggatgtgctg atattacgac aaggcaaaat tggcagattc gtggagttgt actgcctgat     540
gtgccggaga tactaagggg actagcagaa gttgggttga ccagtttgca gagtggcatg     600
gacaatgtca ggaatccagt aggaaatcct ctggctggaa ttgatccaga agaaatagta     660
gacacaaggc cttacactaa tttgctctcc caatttatca ctggcaattc acgaggcaat     720
cccgcagttt ctaacttgcc aaggaagtgg aatccgtgtg tagtaggctc tcatgatctt     780
tatgagcatc cccatatcaa cgatctcgcg tacatgcctg ccacgaaaga cgggcgattt     840
ggattcaacc tgcttgtggg agggttcttc agtgcaaaaa gatgtgatga ggcaattcct     900
cttgatgcat gggttccagc cgatgatgtt gttccggttt gcaaagcaat actggaagct     960
tttagagatc ttggtttcag agggaacaga cagaaatgta aatgatgtg gttaatcgat     1020
gaactgggtg tagaaggatt cagggcagag gtcgagaaga aatgccaca gcaacaacta    1080
gagagagcat ctccagaaga cttggttcag aaacaatggg aaagaagaga ttatcttggt    1140
gtacatccac aaaaacaaga aggctacagc tttatcggcc ttcacattcc agtgggtcgt    1200
gttcaagcag acgatatgga tgagctagct cgtttagctg atgaatatgg ttcaggagag    1260
atccggctta ctgtggaaca aaacattatt attcccaata ttgagacctc aaaaattgag    1320
gcactgctca aagagcctgt tctgagcaca ttttcacctg atccacctat tctcatgaaa    1380
ggtttagtgg cttgtactgg taaccagttt tgtggacaag ccataatcga gactaaagct    1440
cgttccttga agataactga agaggttcaa cggcaagttt ctttgacaaa accagtaagg    1500
atgcactgga caggctgccc gaatacgtgt gcacaagttc aagttgcgga cattggattc    1560
atgggatgcc tgactagaga taagaacggg aagactgtgg aaggcgccga tgttttttta    1620
ggaggaagaa tagggagtga ttcacatttg ggagaagtat ataagaaggc tgttccttgt    1680
gatgatttgg taccacttgt tgtggacttg ctagttaaca actttggtgc agttccacga    1740
gaaagagaag aaacagaaga ttaa                                           1764
```

<210> SEQ ID NO 29
<211> LENGTH: 587
<212> TYPE: PRT
<213> ORGANISM: Nicotiana tabacum

<400> SEQUENCE: 29

```
Met Ala Ser Phe Ser Ile Lys Phe Leu Ala Pro Ser Leu Pro Asn Pro
1               5                   10                  15

Ala Arg Phe Ser Lys Asn Ala Val Lys Leu His Ala Thr Pro Pro Ser
            20                  25                  30

Val Ala Ala Pro Pro Thr Gly Ala Pro Glu Val Ala Ala Glu Arg Leu
```

-continued

```
                35                  40                  45
Glu Pro Arg Val Glu Glu Lys Asp Gly Tyr Trp Ile Leu Lys Glu Gln
 50                  55                  60

Phe Arg Lys Gly Ile Asn Pro Gln Glu Lys Val Lys Ile Glu Lys Glu
65                  70                  75                  80

Pro Met Lys Leu Phe Met Glu Asn Gly Ile Glu Leu Ala Lys Ile
                85                  90                  95

Pro Ile Glu Glu Ile Asp Gln Ser Lys Leu Thr Lys Asp Asp Ile Asp
                100                 105                 110

Val Arg Leu Lys Trp Leu Gly Leu Phe His Arg Lys Asn Gln Tyr
            115                 120                 125

Gly Arg Phe Met Met Arg Leu Lys Leu Pro Asn Gly Val Thr Thr Ser
        130                 135                 140

Ala Gln Thr Arg Tyr Leu Ala Ser Val Ile Arg Lys Tyr Gly Lys Glu
145                 150                 155                 160

Gly Cys Ala Asp Ile Thr Thr Arg Gln Asn Trp Gln Ile Arg Gly Val
                165                 170                 175

Val Leu Pro Asp Val Pro Glu Ile Leu Lys Gly Leu Ala Glu Val Gly
            180                 185                 190

Leu Thr Ser Leu Gln Ser Gly Met Asp Asn Val Arg Asn Pro Val Gly
        195                 200                 205

Asn Pro Leu Ala Gly Ile Asp Pro Glu Glu Ile Val Asp Thr Arg Pro
    210                 215                 220

Tyr Thr Asn Leu Leu Ser Gln Phe Ile Thr Gly Asn Ser Arg Gly Asn
225                 230                 235                 240

Pro Ala Val Ser Asn Leu Pro Arg Lys Trp Asn Pro Cys Val Val Gly
                245                 250                 255

Ser His Asp Leu Tyr Glu His Pro His Ile Asn Asp Leu Ala Tyr Met
            260                 265                 270

Pro Ala Thr Lys Asp Gly Arg Phe Gly Phe Asn Leu Leu Val Gly Gly
        275                 280                 285

Phe Phe Ser Ala Lys Arg Cys Asp Glu Ala Ile Pro Leu Asp Ala Trp
    290                 295                 300

Val Pro Ala Asp Asp Val Val Pro Val Cys Lys Ala Ile Leu Glu Ala
305                 310                 315                 320

Phe Arg Asp Leu Gly Phe Arg Gly Asn Arg Gln Lys Cys Arg Met Met
                325                 330                 335

Trp Leu Ile Asp Glu Leu Gly Val Glu Gly Phe Arg Ala Glu Val Glu
            340                 345                 350

Lys Arg Met Pro Gln Gln Gln Leu Glu Arg Ala Ser Pro Glu Asp Leu
        355                 360                 365

Val Gln Lys Gln Trp Glu Arg Arg Asp Tyr Leu Gly Val His Pro Gln
    370                 375                 380

Lys Gln Glu Gly Tyr Ser Phe Ile Gly Leu His Ile Pro Val Gly Arg
385                 390                 395                 400

Val Gln Ala Asp Asp Met Asp Glu Leu Ala Arg Leu Ala Asp Glu Tyr
                405                 410                 415

Gly Ser Gly Glu Ile Arg Leu Thr Val Glu Gln Asn Ile Ile Ile Pro
            420                 425                 430

Asn Ile Glu Thr Ser Lys Ile Glu Ala Leu Leu Lys Glu Pro Val Leu
        435                 440                 445

Ser Thr Phe Ser Pro Asp Pro Pro Ile Leu Met Lys Gly Leu Val Ala
450                 455                 460
```

```
Cys Thr Gly Asn Gln Phe Cys Gly Gln Ala Ile Ile Glu Thr Lys Ala
465                 470                 475                 480

Arg Ser Leu Lys Ile Thr Glu Glu Val Gln Arg Gln Val Ser Leu Thr
            485                 490                 495

Lys Pro Val Arg Met His Trp Thr Gly Cys Pro Asn Thr Cys Ala Gln
                500                 505                 510

Val Gln Val Ala Asp Ile Gly Phe Met Gly Cys Leu Thr Arg Asp Lys
        515                 520                 525

Asn Gly Lys Thr Val Glu Gly Ala Asp Val Phe Leu Gly Gly Arg Ile
    530                 535                 540

Gly Ser Asp Ser His Leu Gly Glu Val Tyr Lys Lys Ala Val Pro Cys
545                 550                 555                 560

Asp Asp Leu Val Pro Leu Val Val Asp Leu Leu Val Asn Asn Phe Gly
                565                 570                 575

Ala Val Pro Arg Glu Arg Glu Thr Glu Asp
                580                 585
```

<210> SEQ ID NO 30
<211> LENGTH: 1755
<212> TYPE: DNA
<213> ORGANISM: Nicotiana tabacum

<400> SEQUENCE: 30

```
atggcatctt tttctgttaa attctcagct acttcattac caaatcataa aagattttca      60
aagctacatg caacaccgcc gcagacggtg gctgtagccc catctggggc ggcggagata     120
gcatcggaga ggttagagcc tagagtagaa gaaaaagatg ggtattgggt acttaaggaa     180
aaattcagac aagggataaa tccagctgaa aaagctaaga ttgagaagga accaatgaaa     240
ttgtttatgg aaaatggtat tgaagatcta gctaagatct cacttgaaga gatcgaaggg     300
tctaagctta ctaaagatga tattgatgtt aggctcaagt ggcttggcct tttcccatagg    360 agaaagcatc actatggccg attcatgatg agattgaagc ttccaaatgg ggtaacaacg     420
agttcccaaa ctcgatactt agccagtgtg ataaggaaat atgggaaaga tggatgtgct     480
gatgtgacga caaggcaaaa ttggcagatt cgtggggttg tactacctga tgtacccgag     540
attctaaagg gactggatga agttggctta accagtctgc agagtggcat ggacaatgtt     600
agaaatccgg tgggaaatcc tctggcgggg attgatccac atgaaattgt agacacaagg    660
ccttacacta atttgctctc ccaatatgtt actgccaatt ttcgtggcaa tccggctgtg    720
actaacttgc aaggaagtg gaatgtatgt gtaatagggt cacacgatct ttatgagcat      780
ccccagatca cgatcttgc ctatatgccg gcaacaaaag atggacgatt tggattcaac     840
ctgcttgtgg gtggattctt cagtccgaag cgatgtgcag aggcagttcc tcttgatgca    900
tgggttccag ctgatgacgt agtccctgtt tgcaaagcaa tattagaagc ttatagagat    960
cttggcacca gagggaacag gcagaaaaca agaatgatgt ggttagttga tgaactgggc   1020
gttgaaggat tcagggcaga ggttgtaaag agaatgcctc aacaaaagct agatagagaa   1080
tcaacagagg acttggttca aaaacaatgg gaaggagag aatacttgg cgtgcatcca     1140 cagaaacaag aagggtacag ctttgttggt cttcacattc cagtgggtcg tgtccaagca   1200
gatgacatgg acgagctagc tcgtttggcc gatgagtatg gttccggaga gctccggctg   1260
actgttgaac aaaacatcat tattcccaat gttaagaact caaagatcga ggcattgctc   1320
aatgaacctc tcttaaagaa cagattttca accgatccac ctattctcat gaaaaatttg   1380
```

```
gtcgcttgta ctggtaacca attttgcggg aaagccataa ttgagactaa ggcacgatcc  1440
atgaaaataa ctgaggaggt tcaactacta gtttctataa cgcagcctgt gaggatgcat  1500
tggactggtt gcccgaattc atgtgcacaa gttcaggtcg cggatattgg atttatggga  1560
tgcttgacaa gaaagaagg aaaaactgta gaaggtgctg atgtttattt gggaggcaga  1620 ataggagtg actcacattt gggagatgtt tataagaaat cagtaccctg tgaggatttg  1680
gtgccaataa ttgtggactt actagttgac aactttggtg ctgttccaag agaaagagaa  1740
gaagcagaag attaa                                                    1755

<210> SEQ ID NO 31
<211> LENGTH: 584
<212> TYPE: PRT
<213> ORGANISM: Nicotiana tabacum

<400> SEQUENCE: 31
```

Met Ala Ser Phe Ser Val Lys Phe Ser Ala Thr Ser Leu Pro Asn His
1               5                   10                  15

Lys Arg Phe Ser Lys Leu His Ala Thr Pro Pro Gln Thr Val Ala Val
            20                  25                  30

Ala Pro Ser Gly Ala Ala Glu Ile Ala Ser Glu Arg Leu Glu Pro Arg
        35                  40                  45

Val Glu Glu Lys Asp Gly Tyr Trp Val Leu Lys Glu Lys Phe Arg Gln
    50                  55                  60

Gly Ile Asn Pro Ala Glu Lys Ala Lys Ile Glu Lys Glu Pro Met Lys
65                  70                  75                  80

Leu Phe Met Glu Asn Gly Ile Glu Asp Leu Ala Lys Ile Ser Leu Glu
                85                  90                  95

Glu Ile Glu Gly Ser Lys Leu Thr Lys Asp Asp Ile Asp Val Arg Leu
            100                 105                 110

Lys Trp Leu Gly Leu Phe His Arg Arg Lys His His Tyr Gly Arg Phe
        115                 120                 125

Met Met Arg Leu Lys Leu Pro Asn Gly Val Thr Thr Ser Ser Gln Thr
    130                 135                 140

Arg Tyr Leu Ala Ser Val Ile Arg Lys Tyr Gly Lys Asp Gly Cys Ala
145                 150                 155                 160

Asp Val Thr Thr Arg Gln Asn Trp Gln Ile Arg Gly Val Val Leu Pro
                165                 170                 175

Asp Val Pro Glu Ile Leu Lys Gly Leu Asp Glu Val Gly Leu Thr Ser
            180                 185                 190

Leu Gln Ser Gly Met Asp Asn Val Arg Asn Pro Val Gly Asn Pro Leu
        195                 200                 205

Ala Gly Ile Asp Pro His Glu Ile Val Asp Thr Arg Pro Tyr Thr Asn
    210                 215                 220

Leu Leu Ser Gln Tyr Val Thr Ala Asn Phe Arg Gly Asn Pro Ala Val
225                 230                 235                 240

Thr Asn Leu Pro Arg Lys Trp Asn Val Cys Val Ile Gly Ser His Asp
                245                 250                 255

Leu Tyr Glu His Pro Gln Ile Asn Asp Leu Ala Tyr Met Pro Ala Thr
            260                 265                 270

Lys Asp Gly Arg Phe Gly Phe Asn Leu Leu Val Gly Gly Phe Phe Ser
        275                 280                 285

Pro Lys Arg Cys Ala Glu Ala Val Pro Leu Asp Ala Trp Val Pro Ala
    290                 295                 300

```
Asp Asp Val Val Pro Val Cys Lys Ala Ile Leu Glu Ala Tyr Arg Asp
305                 310                 315                 320

Leu Gly Thr Arg Gly Asn Arg Gln Lys Thr Arg Met Met Trp Leu Val
            325                 330                 335

Asp Glu Leu Gly Val Glu Gly Phe Arg Ala Glu Val Val Lys Arg Met
            340                 345                 350

Pro Gln Gln Lys Leu Asp Arg Glu Ser Thr Glu Asp Leu Val Gln Lys
            355                 360                 365

Gln Trp Glu Arg Arg Glu Tyr Leu Gly Val His Pro Gln Lys Gln Glu
    370                 375                 380

Gly Tyr Ser Phe Val Gly Leu His Ile Pro Val Gly Arg Val Gln Ala
385                 390                 395                 400

Asp Asp Met Asp Glu Leu Ala Arg Leu Ala Asp Glu Tyr Gly Ser Gly
            405                 410                 415

Glu Leu Arg Leu Thr Val Glu Gln Asn Ile Ile Pro Asn Val Lys
            420                 425                 430

Asn Ser Lys Ile Glu Ala Leu Leu Asn Glu Pro Leu Leu Lys Asn Arg
            435                 440                 445

Phe Ser Thr Asp Pro Pro Ile Leu Met Lys Asn Leu Val Ala Cys Thr
450                 455                 460

Gly Asn Gln Phe Cys Gly Lys Ala Ile Ile Glu Thr Lys Ala Arg Ser
465                 470                 475                 480

Met Lys Ile Thr Glu Glu Val Gln Leu Leu Val Ser Ile Thr Gln Pro
            485                 490                 495

Val Arg Met His Trp Thr Gly Cys Pro Asn Ser Cys Ala Gln Val Gln
            500                 505                 510

Val Ala Asp Ile Gly Phe Met Gly Cys Leu Thr Arg Lys Glu Gly Lys
            515                 520                 525

Thr Val Glu Gly Ala Asp Val Tyr Leu Gly Gly Arg Ile Gly Ser Asp
530                 535                 540

Ser His Leu Gly Asp Val Tyr Lys Ser Val Pro Cys Glu Asp Leu
545                 550                 555                 560

Val Pro Ile Ile Val Asp Leu Leu Val Asp Asn Phe Gly Ala Val Pro
            565                 570                 575

Arg Glu Arg Glu Glu Ala Glu Asp
            580

<210> SEQ ID NO 32
<211> LENGTH: 1813
<212> TYPE: DNA
<213> ORGANISM: Zea mays

<400> SEQUENCE: 32
ggccgcacag ggcgcgcccg cgcggccgtc tccgtgccgc cgccggcggg ggagcaggtc      60
ccgacggagc ggctggagcc gagggtcgag gagcgggcgg gcgggtactg ggtcctcaag     120
gagaagtacc gggcggggct gaacccgcag gagaaggtga agctggagaa ggagcccatg     180
gcgctgttca tggagggcgg catccaggac ctggccaggg tccccatgga gcagatcgac     240
gccgccaagc tcaccaagga cgacgtcgac gtccgcctca gtggctcgg cctcttccac      300 cgccgcaagc accagtacgg gcggttcatg atgcggctga agctgcccaa cggcgtgacg     360
acgagcgagc agacgcggta cctggcgagc gtcatcgagg cgtacggcgc cgacgggtgc     420
gcggacgtga ccacccggca gaactggcag atccgcgggg tgacgctccc ggacgtcccg     480
gccatcctgg acggcctccg cgccgtcggc ctcaccagcc tgcagagcgg catggacaac     540
```

```
gtgcgcaacc ccgtcggcaa cccgctcgcc ggcgtcgacc cccacgagat cgtcgacacg    600 cgccccctaca ccaaccttct ctcctcctac gtcaccaaca actcccaggg gaaccccaca    660
atcaccaacc tgccgaggaa atggaacgtc tgcgtcatcg gctcgcatga cctgtacgag    720
cacccgcaca tcaacgacct cgcgtacatg ccggccgtca aggacggcga gttcggcttc    780
aaccttctgg tgggcgggtt catcagcccc aagaggtggg ccgaggcgtt gccgctcgac    840
gcctgggtcg ccggggacga cgtcgtcccc gtgtgcaagg ccatcctcga ggcgtaccgg    900
gacctcggct ccaggggcaa ccggcagaag acgcgcatga tgtggctcat cgacgagctc    960
gggatggagg tgttccggtc ggaggtggag aagaggatgc cgaacggggt gctggagcgc   1020
gccgcgccgg aggacctcgt cgacaagcgc tgggagcggc gggactacct cggcgtgcac   1080
ccgcagaagc aggaaggcct gtcgtacgtg ggcctccacg tgccggtggg ccggctgcag   1140
gccgcggaca tgttcgagct ggcgcggctc gccgacgagt acggcaccgg cgagctccgg   1200
ctcacggtgg agcagaacat cgtgctcccc aacgtcagca acgagaggct cgacgcgctg   1260
ctggcggagc cgctgctgca ggagcagcgg ctctcgccgc ggccgtcgat gctgctcagg   1320
gggctggtgg cgtgcacggg caaccagttc tgcgggcagg ccatcatcga gaccaaggcg   1380
cgggcgctgc aggtggcgcg ggaggtggag aagcgcgtgg ccgtgccgcg gccggtccgc   1440
atgcactgga ccggatgccc caacagctgc ggccaggtgc aggtggcgga catcggcttc   1500
atgggctgcc tcaccaagga cagcgacggc aagatcgtcg aggccgcgga catcttcgtg   1560 ggcgccgcg tcggcagcga ctcgcacctg gccgacgtct accggaagtc cgtgccgtgc   1620
aaggacctgg tgcccatcgt ggccgacctc ttggtggagc ggttcggggc cgtgccgagg   1680
gagagggagg aggatgagga gtaggacctt cgtcaagcgc cggctgggac tgtcctgacc   1740
tattttatga ggtcttgatt ggatgtatat atatattcat cttaatctat atggatttct   1800
gaagtttgat cta                                                       1813
```

<210> SEQ ID NO 33
<211> LENGTH: 567
<212> TYPE: PRT
<213> ORGANISM: Zea mays

<400> SEQUENCE: 33

Gly Arg Thr Gly Arg Ala Arg Ala Ala Val Ser Val Pro Pro Ala
1               5                   10                  15

Gly Glu Gln Val Pro Thr Glu Arg Leu Glu Pro Arg Val Glu Glu Arg
            20                  25                  30

Ala Gly Gly Tyr Trp Val Leu Lys Glu Lys Tyr Arg Ala Gly Leu Asn
        35                  40                  45

Pro Gln Glu Lys Val Lys Leu Glu Lys Glu Pro Met Ala Leu Phe Met
    50                  55                  60

Glu Gly Gly Ile Gln Asp Leu Ala Arg Val Pro Met Glu Gln Ile Asp
65                  70                  75                  80

Ala Ala Lys Leu Thr Lys Asp Asp Val Asp Val Arg Leu Lys Trp Leu
                85                  90                  95

Gly Leu Phe His Arg Arg Lys His Gln Tyr Gly Arg Phe Met Met Arg
            100                 105                 110

Leu Lys Leu Pro Asn Gly Val Thr Thr Ser Glu Gln Thr Arg Tyr Leu
        115                 120                 125

Ala Ser Val Ile Glu Ala Tyr Gly Ala Asp Gly Cys Ala Asp Val Thr
    130                 135                 140

```
Thr Arg Gln Asn Trp Gln Ile Arg Gly Val Thr Leu Pro Asp Val Pro
145                 150                 155                 160

Ala Ile Leu Asp Gly Leu Arg Ala Val Gly Leu Thr Ser Leu Gln Ser
            165                 170                 175

Gly Met Asp Asn Val Arg Asn Pro Val Gly Asn Pro Leu Ala Gly Val
        180                 185                 190

Asp Pro His Glu Ile Val Asp Thr Arg Pro Tyr Thr Asn Leu Leu Ser
    195                 200                 205

Ser Tyr Val Thr Asn Asn Ser Gln Gly Asn Pro Thr Ile Thr Asn Leu
210                 215                 220

Pro Arg Lys Trp Asn Val Cys Val Ile Gly Ser His Asp Leu Tyr Glu
225                 230                 235                 240

His Pro His Ile Asn Asp Leu Ala Tyr Met Pro Ala Val Lys Asp Gly
            245                 250                 255

Glu Phe Gly Phe Asn Leu Leu Val Gly Gly Phe Ile Ser Pro Lys Arg
        260                 265                 270

Trp Ala Glu Ala Leu Pro Leu Asp Ala Trp Val Ala Gly Asp Asp Val
    275                 280                 285

Val Pro Val Cys Lys Ala Ile Leu Glu Ala Tyr Arg Asp Leu Gly Ser
290                 295                 300

Arg Gly Asn Arg Gln Lys Thr Arg Met Met Trp Leu Ile Asp Glu Leu
305                 310                 315                 320

Gly Met Glu Val Phe Arg Ser Glu Val Glu Lys Arg Met Pro Asn Gly
            325                 330                 335

Val Leu Glu Arg Ala Ala Pro Glu Asp Leu Val Asp Lys Arg Trp Glu
        340                 345                 350

Arg Arg Asp Tyr Leu Gly Val His Pro Gln Lys Gln Glu Gly Leu Ser
    355                 360                 365

Tyr Val Gly Leu His Val Pro Val Gly Arg Leu Gln Ala Ala Asp Met
370                 375                 380

Phe Glu Leu Ala Arg Leu Ala Asp Glu Tyr Gly Thr Gly Glu Leu Arg
385                 390                 395                 400

Leu Thr Val Glu Gln Asn Ile Val Leu Pro Asn Val Ser Asn Glu Arg
            405                 410                 415

Leu Asp Ala Leu Leu Ala Glu Pro Leu Leu Gln Glu Gln Arg Leu Ser
        420                 425                 430

Pro Arg Pro Ser Met Leu Leu Arg Gly Leu Val Ala Cys Thr Gly Asn
    435                 440                 445

Gln Phe Cys Gly Gln Ala Ile Ile Glu Thr Lys Ala Arg Ala Leu Gln
450                 455                 460

Val Ala Arg Glu Val Glu Lys Arg Val Ala Val Pro Arg Pro Val Arg
465                 470                 475                 480

Met His Trp Thr Gly Cys Pro Asn Ser Cys Gly Gln Val Gln Val Ala
            485                 490                 495

Asp Ile Gly Phe Met Gly Cys Leu Thr Lys Asp Ser Asp Gly Lys Ile
        500                 505                 510

Val Glu Ala Ala Asp Ile Phe Val Gly Gly Arg Val Gly Ser Asp Ser
    515                 520                 525

His Leu Ala Asp Val Tyr Arg Lys Ser Val Pro Cys Lys Asp Leu Val
530                 535                 540

Pro Ile Val Ala Asp Leu Leu Val Glu Arg Phe Gly Ala Val Pro Arg
545                 550                 555                 560
```

Glu Arg Glu Glu Asp Glu Glu
565